(12) United States Patent
Kim et al.

(10) Patent No.: US 9,296,817 B2
(45) Date of Patent: Mar. 29, 2016

(54) ANTIBODIES CROSS-REACTIVE TO HUMAN AND MOUSE C-MET AND USES THEREOF

(71) Applicant: SAMSUNG LIFE PUBLIC WELFARE FOUNDATION, Seoul (KR)

(72) Inventors: Seok-Hyung Kim, Seoul (KR); Do-Hyun Nam, Seoul (KR); Hyun-Kyu Park, Seoul (KR); Kyeung Min Joo, Seoul (KR); Nam Kyung Lee, Jeollabuk-do (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days.

(21) Appl. No.: 14/184,960

(22) Filed: Feb. 20, 2014

(65) Prior Publication Data

US 2014/0370022 A1    Dec. 18, 2014

(30) Foreign Application Priority Data

Jun. 18, 2013 (KR) .................. 10-2013-0069666

(51) Int. Cl.
  *C07K 16/00* (2006.01)
  *C07K 16/28* (2006.01)
  *A61K 39/00* (2006.01)

(52) U.S. Cl.
  CPC ....... *C07K 16/2836* (2013.01); *A61K 2039/505* (2013.01); *C07K 2317/33* (2013.01); *C07K 2317/34* (2013.01); *C07K 2317/76* (2013.01); *C07K 2317/92* (2013.01)

(58) Field of Classification Search
  None
  See application file for complete search history.

(56) References Cited

PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Strome et al., The Oncologist, 2007; 12:1084-95.*
Brand et al., Anticancer Res. 2006; 26:463-.*
Paolo M. Comoglio, Silvia Giordano and Livio Trusolino, "Drug development of MET inhibitors: targeting oncogene addiction and expedience," Nature Reviews, vol. 7, Jun. 2008, pp. 504-516.
Tobias Martens et al., "A Novel One-Armed Anti-c-Met Antibody Inhibits Glioblastoma Growth In vivo", Clin Cancer Res 2006;12(20) Oct. 15, 2006.

\* cited by examiner

*Primary Examiner* — Sheela J Huff
(74) *Attorney, Agent, or Firm* — Harness, Dickey & Pierce, P.L.C.

(57) ABSTRACT

The antibody of the invention has high specificity to human c-Met and is cross-reactive to mouse c-Met. The antibody or its antigen-binding fragment of the invention is capable of specifically binding to human c-Met as well as mouse c-Met, more accurate preclinical results can be confirmed in the efficacy evaluation using mouse tumor models. The antibody of the invention inhibits the growth of cancer cells derived from various cancers by a considerable binding affinity to c-Met and the suppression of c-Met function therefrom, inhibits the phosphorylation of c-Met and downstream signaling molecules to suppress c-Met signaling, and inhibits neovascularization, thereby being very efficient in the prevention and treatment of cancers.

4 Claims, 26 Drawing Sheets

2A01 scFv concentration (ng/ml)

HepG2

H441

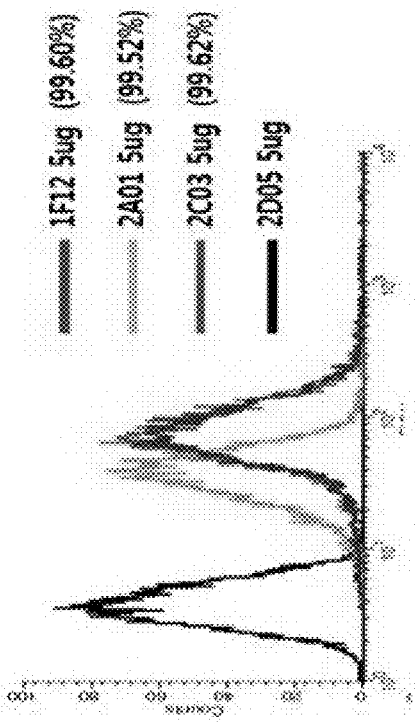
FIG. 7E U-87MG
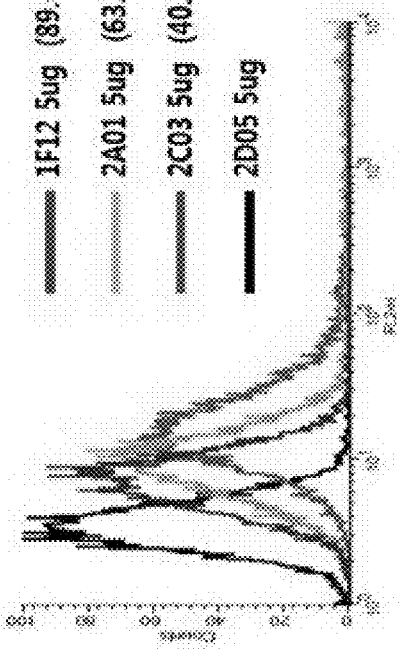
FIG. 7F
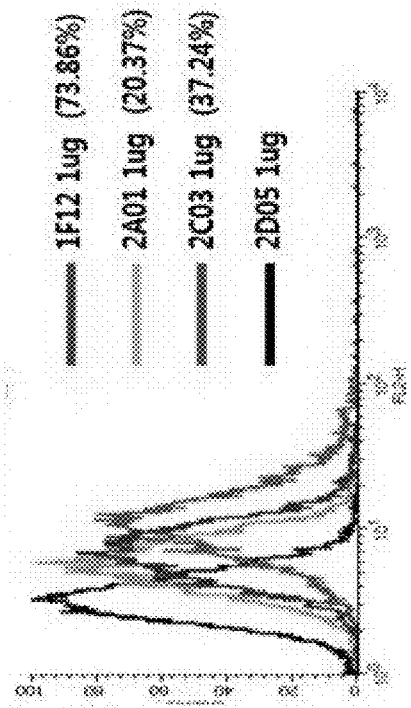
FIG. 7G MKN45
FIG. 7H

Caki-1

U-87 MG

HepG2

U-87 MG

HepG2

FIG. 9E
FIG. 9F
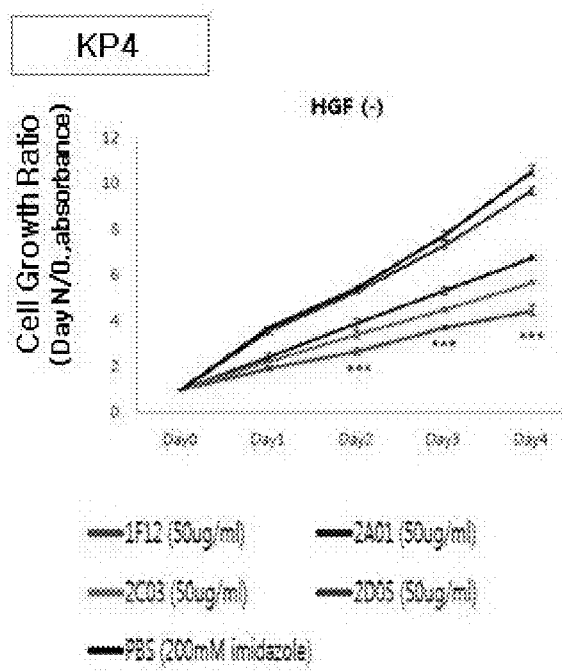
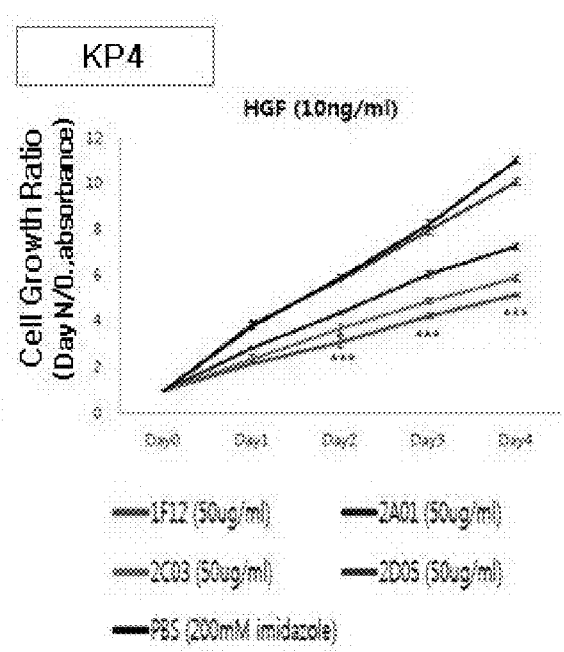

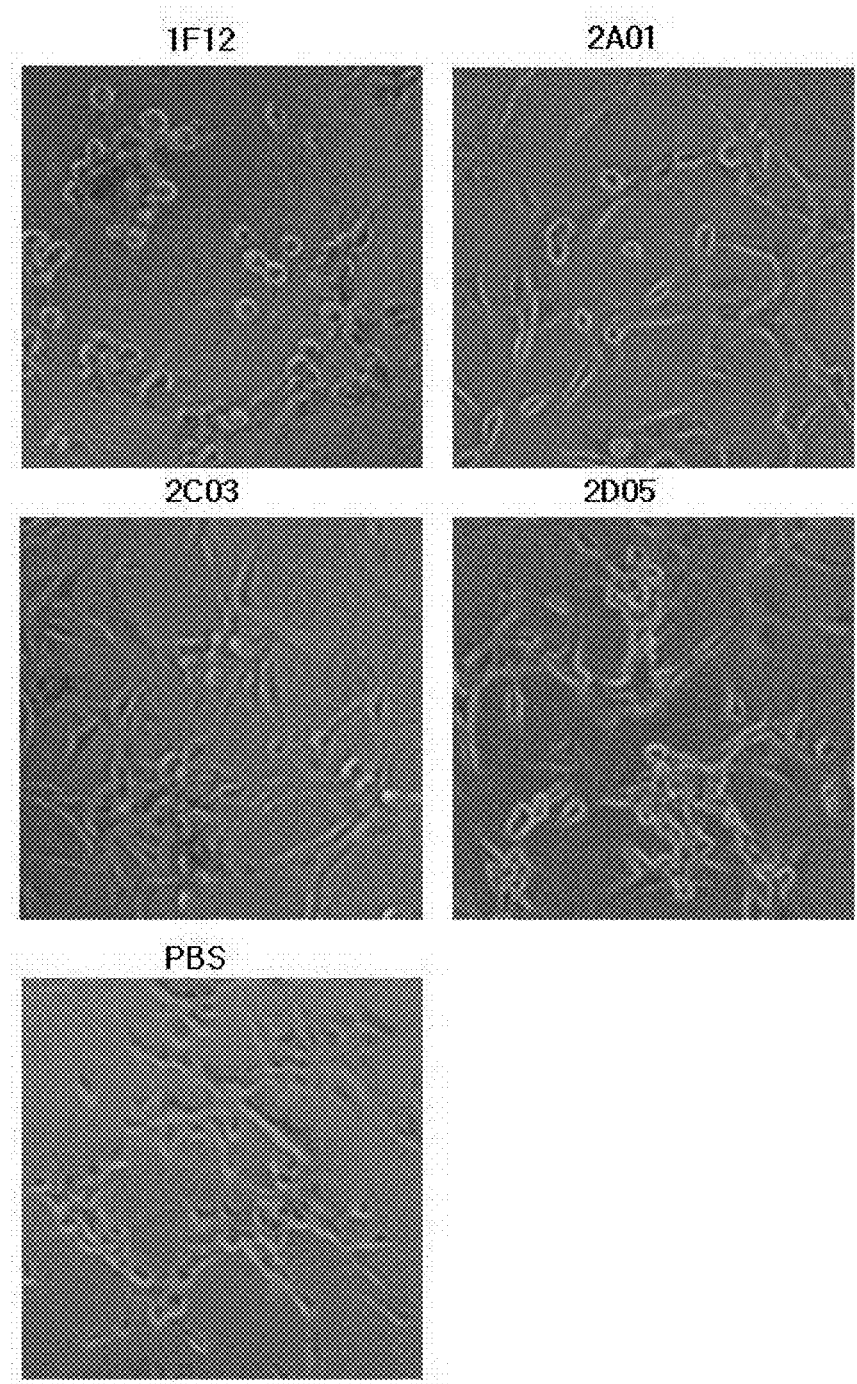

FIG. 13A

001 KEALAKSEMNVNMKY (SEQ ID NO: 33)
002 AKSEMNVNMKYQLPN (SEQ ID NO: 34)
003 MNVNMKYQLPNFTAE (SEQ ID NO: 35)
004 MKYQLPNFTAETPIQ (SEQ ID NO: 36)
005 LPNFTAETPIQNVIL (SEQ ID NO: 37)
006 TAETPIQNVILHEHH (SEQ ID NO: 38)
007 PIQNVILHEHHIFLG (SEQ ID NO: 39)
008 VILHEHHIFLGATNY (SEQ ID NO: 40)
009 EHHIFLGATNYIYVL (SEQ ID NO: 41)
010 FLGATNYiYVLNEED (SEQ ID NO: 42)
011 TNYIYVLNEEDLQKV (SEQ ID NO: 43)
012 YVLNEEDLQKVAEYK (SEQ ID NO: 44)
013 EEDLQKVAEYKTGPV (SEQ ID NO: 45)
014 QKVAEYKTGPVLEHP (SEQ ID NO: 46)
015 EYKTGPVLEHPDCFP (SEQ ID NO: 47)
016 GPVLEHPDCFPCQDC (SEQ ID NO: 48)
017 EHPDCFPCQDCSSKA (SEQ ID NO: 49)
018 CFPCQDCSSKANLSG (SEQ ID NO: 50)
019 QDCSSKANLSGGVWK (SEQ ID NO: 51)
020 SKANLSGGVWKDNIN (SEQ ID NO: 52)
021 LSGGVWKDNINMALV (SEQ ID NO: 53)
022 VWKDNINMALVVDTY (SEQ ID NO: 54)
023 N1NMALVVDTYYDDQ (SEQ ID NO: 55)
024 ALVVDTYYDDQLISC (SEQ ID NO: 56)
025 DTYYDDQLISCGSVN (SEQ ID NO: 57)
026 DDQLISCGSVNRGTC (SEQ ID NO: 58)
027 ISCGSVNRGTCQRHV (SEQ ID NO: 59)
028 SVNRGTCQRHVFPHN (SEQ ID NO: 60)
029 GTCQRHVFPHNHTAD (SEQ ID NO: 61)
030 RHVFPHNHTADIQSE (SEQ ID NO: 62)
031 PHNHTADIQSEVHCI (SEQ ID NO: 63)
032 TADIQSEVHCIFSPQ (SEQ ID NO: 64)
033 QSEVHCIFSPQIEEP (SEQ ID NO: 65)
034 HCIFSPQIEEPSQCP (SEQ ID NO: 66)
035 SPQIEEPSQCPDCVV (SEQ ID NO: 67)
036 EEPSQCPDCVVSALG (SEQ ID NO: 68)
037 QCPDCVVSALGAKVL (SEQ ID NO: 69)
038 CVVSALGAKVLSSVK (SEQ ID NO: 70)
039 ALGAKVLSSVKDRFI (SEQ ID NO: 71)

040 KVLSSVKDRFINFFV (SEQ ID NO: 72)
041 SVKDRFINFFVGNTI (SEQ ID NO: 73)
042 RFINFFVGNTINSSY (SEQ ID NO: 74)
043 FFVGNTINS5YFPDH (SEQ ID NO: 75)
044 NTINSSYFPDHPLHS (SEQ ID NO: 76)
045 SSYFPDHPLHSISVR (SEQ ID NO: 77)
046 PDHPLHSISVRRLKE (SEQ ID NO: 78)
047 LHSISVRRLKETKDG (SEQ ID NO: 79)
048 SvRRLKETKDGFMFL (SEQ ID NO: 80)
049 LKETKDGFMFLTDQS (SEQ ID NO: 81)
050 KDGFMFLTDQSYtDV (SEQ ID NO: 82)
051 MFLTDQSYIDVLPEF (SEQ ID NO: 83)
052 DQSYIDVLPEFRDSY (SEQ ID NO: 84)
053 IDVLPEFRDSYPIKY (SEQ ID NO: 85)
054 PEFRDSYPIKYVHAF (SEQ ID NO: 86)
055 *DSYPIKYVHAFESNN* (SEQ ID NO: 87)
056 IKYVHAFESNNFiYF (SEQ ID NO: 88)
057 HAFESNNFiYFLTVQ (SEQ ID NO: 89)
058 SNNFIYFLTVQRETL (SEQ ID NO: 90)
059 IYFLTVQRETLDAQT (SEQ ID NO: 91)
060 TVQRETLDAQTFHTR (SEQ ID NO: 92)
061 ETLDAQTFHTRIIRF (SEQ ID NO: 93)
062 AQTFHTRIIRFCSIN (SEQ ID NO: 94)
063 HTRIIRFCSINSGLH (SEQ ID NO: 95)
064 IRFCSINSGLHSYME (SEQ ID NO: 96)
065 SINSGLHSYMEMPLE (SEQ ID NO: 97)
066 GLHSYMEMPLECILT (SEQ ID NO: 98)
067 YMEMPLECILTEKRK (SEQ ID NO: 99)
068 PLECILTEKRKKRST (SEQ ID NO: 100)
069 ILTEKRKKRSTKKEV (SEQ ID NO: 101)
070 KRKKRSTKKEVFNIL (SEQ ID NO: 102)
071 RSTKKEVFNILQAAY (SEQ ID NO: 103)
072 KEVFNILQAAYVSKP (SEQ ID NO: 104)
073 NILQAAYVSKPGAQL (SEQ ID NO: 105)
074 AAYVSKPGAQLAAQI (SEQ ID NO: 106)
075 SKPGAQLARQIGASL (SEQ ID NO: 107)
076 AQLARQIGASLNDDI (SEQ ID NO: 108)
077 RQIGASLNDDILFGV (SEQ ID NO: 109)
078 ASLNDDILFGVFAQS (SEQ ID NO: 110)

FIG. 13B

```
079 DDILFGVFAQSKPDS (SEQ ID NO: 111)      118 TLNQNGYTLVITGKK (SEQ ID NO: 150)
080 FGVFAQSKPDSAEPM (SEQ ID NO: 112)      119 NGYTLVITGKKITKI (SEQ ID NO: 151)
081 AQSKPDSAEPMDRSA (SEQ ID NO: 113)      120 LVITGKKITKIPLNG (SEQ ID NO: 152)
082 PDSAEPMDRSAMCAF (SEQ ID NO: 114)      121 GKKITKIPLNGLGCR (SEQ ID NO: 153)
083 EPMDRSAMCAFPIKY (SEQ ID NO: 115)      122 TKIPLNGLGCRHFQS (SEQ ID NO: 154)
084 RSAMCAFPIKYVNDF (SEQ ID NO: 116)      123 LNGLGCRHFQSCSQC (SEQ ID NO: 155)
085 CAFPIKYVNDFFNKI (SEQ ID NO: 117)      124 GCRHFQSCSQCLSAP (SEQ ID NO: 156)
086 IKYVNDFFNKIVNKN (SEQ ID NO: 118)      125 FQSCSQCLSAPPFVQ (SEQ ID NO: 157)
087 NDFFNKIVNKNNVRC (SEQ ID NO: 119)      126 SQCLSAPPFVQCGWC (SEQ ID NO: 158)
088 EHCFNRTLLRNSSGC (SEQ ID NO: 120)      127 SAPPFVQCGWCHDKC (SEQ ID NO: 159)
088 NKIVNKNNVRCLQHF (SEQ ID NO: 121)      128 FVQCGWCHDKCVRSE (SEQ ID NO: 160)
089 NKNNVRCLQHFYGPN (SEQ ID NO: 122)      129 GWCHDKCVRSEECLS (SEQ ID NO: 161)
090 VRCLQHFYGPNHEHC (SEQ ID NO: 123)      130 DKCVRSEECLSGTWT (SEQ ID NO: 162)
091 QHFYGPNHEHCFNRT (SEQ ID NO: 124)      131 RSEECLSGTWTQQIC (SEQ ID NO: 163)
092 GPNHEHCFNRTLLRN (SEQ ID NO: 125)      132 CLSGTWTQQICLPAI (SEQ ID NO: 164)
094 NRTLLRNSSGCEARR (SEQ ID NO: 126)      133 TWTQQICLPAIYKVF (SEQ ID NO: 165)
095 LRNSSGCEARRDEYR (SEQ ID NO: 127)      134 QICLPAIYKVFPNSA (SEQ ID NO: 166)
096 SGCEARRDEYRTEFT (SEQ ID NO: 128)      135 PAIYKVFPNSAPLEG (SEQ ID NO: 167)
097 ARRDEYRTEFTTALQ (SEQ ID NO: 129)      136 KVFPNSAPLEGGTRL (SEQ ID NO: 168)
098 EYRTEFTTALQRVDL (SEQ ID NO: 130)      137 NSAPLEGGTRLTICG (SEQ ID NO: 169)
099 EFTTALQRVDLFMGQ (SEQ ID NO: 131)      138 LEGGTRLTICGWDFG (SEQ ID NO: 170)
100 ALQRVDLFMGQFSEV (SEQ ID NO: 132)      139 TRLTICGWDFGRRN  (SEQ ID NO: 171)
101 VDLFMGQFSEVLLTS (SEQ ID NO: 133)      140 ICGwDFGRRNNKFD  (SEQ ID NO: 172)
102 MGQFSEVLLTSISTF (SEQ ID NO: 134)      141 DFGFRRNNKFDLKKT (SEQ ID NO: 173)
103 SEVLLTSISTFIKGD (SEQ ID NO: 135)      142 RRNNKFDLKKTRVLL (SEQ ID NO: 174)
104 LTSISTFIKGDLTIA (SEQ ID NO: 136)      143 KFDLKKTRVLLGNES (SEQ ID NO: 175)
105 STFIKGDLTIANLGT (SEQ ID NO: 137)      144 KKTRvLLGNESCTLT (SEQ ID NO: 176)
106 KGDLTIANLGTSEGR (SEQ ID NO: 138)      145 VLLGNESCTlTLSES (SEQ ID NO: 177)
107 TIANLGTSEGRFMQV (SEQ ID NO: 139)      146 NESCTLTLSESTMNT (SEQ ID NO: 178)
108 LGTSEGRFMQVVVSR (SEQ ID NO: 140)      147 TLTLSESTMNTLKCT (SEQ ID NO: 179)
109 EGRFMQVVVSRSGPS (SEQ ID NO: 141)      148 SESTMNTLKCTVGPA (SEQ ID NO: 180)
110 MQVVVSRSGPSTPHV (SEQ ID NO: 142)      149 MNTLKCTVGPAMNKH (SEQ ID NO: 181)
111 VSRSGPSTPHVNFLL (SEQ ID NO: 143)      150 KCTVGPAMNKHFNMS (SEQ ID NO: 182)
112 GPSTPHVNFLLDSHP (SEQ ID NO: 144)      151 GPAMNKHFNMSIIIS (SEQ ID NO: 183)
113 PHVNFLLDSHPVSPE (SEQ ID NO: 145)      152 NKHFNMSIIISNGHG (SEQ ID NO: 184)
114 FLLDSHPVSPEVIVE (SEQ ID NO: 146)      153 NMSIIISNGHGTTQY (SEQ ID NO: 185)
115 SHPVSPEVIVEHTLN (SEQ ID NO: 147)      154 IISNGHGTTQYSTFS (SEQ ID NO: 186)
116 SPEVIVEHTLNQNGY (SEQ ID NO: 148)      155 GHGTTQYSTFSYVDP (SEQ ID NO: 187)
117 IVEHTLNQNGYTLVI (SEQ ID NO: 149)      156 TQYSTFSYVDPVITS (SEQ ID NO: 188)
```

FIG. 13C

157 TFSYVDPVITSISPK (SEQ ID NO: 189)
158 VDPVITSISPKYGPM (SEQ ID NO: 190)
159 ITSISPKYGPMAGGT (SEQ ID NO: 191)
159 LKSVSNSILECYTPA (SEQ ID NO: 192)
160 SPKYGPMAGGTLLTL (SEQ ID NO: 193)
161 GPMAGGTLLTLTGNY (SEQ ID NO: 194)
162 GGTLLTLTGNYLNSG (SEQ ID NO: 195)
163 LTLTGNYLNSGNSRH (SEQ ID NO: 196)
164 GNYLNSGNSRHISIG (SEQ ID NO: 197)
165 NSGNSRHISIGGKTC (SEQ ID NO: 198)
166 SRHISIGGKTCTLKS (SEQ ID NO: 199)
167 SIGGKTCTLKSVSNS (SEQ ID NO: 200)
168 KTCTLKSVSNSILEC (SEQ ID NO: 201)
170 SNSILECYTPAQTIS (SEQ ID NO: 202)
171 LECYTPAQTISTEFA (SEQ ID NO: 203)
172 TPAQTISTEFAVKLK (SEQ ID NO: 204)
173 TISTEFAVKLKIDLA (SEQ ID NO: 205)
174 EFAVKLKIDLANRET (SEQ ID NO: 206)
175 KLKIDLANRETSIFS (SEQ ID NO: 207)
176 DLANRETSIFSYRED (SEQ ID NO: 208)
177 RETSIFSYREDPIVY (SEQ ID NO: 209)
178 IFSYREDPIVYEIHP (SEQ ID NO: 210)
179 REDPIVYEIHPTKSF (SEQ ID NO: 211)
180 IVYEIHPTKSFISGG (SEQ ID NO: 212)
181 IHPTKSFISGGSTIT (SEQ ID NO: 213)
182 KSFISGGSTITGVGK (SEQ ID NO: 214)
183 SGGSTITGVGKNLNS (SEQ ID NO: 215)
184 TITGVGKNLNSVSVP (SEQ ID NO: 216)
185 VGKNLNSVSVPRMVI (SEQ ID NO: 217)
186 LNSVSVPRMVINVHE (SEQ ID NO: 218)
187 SVPRMVINVHEAGRN (SEQ ID NO: 219)
188 MVINVHEAGRNFTVA (SEQ ID NO: 220)
189 VHEAGRNFTVACQHR (SEQ ID NO: 221)
190 GRNFTVACQHRSNSE (SEQ ID NO: 222)
191 TVACQHRSNSEIICC (SEQ ID NO: 223)
192 QHRSNSEIICCTTPS (SEQ ID NO: 224)
193 NSEIICCTTPSLQQL (SEQ ID NO: 225)
194 ICCTTPSLQQLNLQL (SEQ ID NO: 226)
195 TPSLQQLNLQLPLKT (SEQ ID NO: 227)

196 QQLNLQLPLKTKAFF (SEQ ID NO: 228)
197 LQLPLKTKAFFMLDG (SEQ ID NO: 229)
198 LKTKAFFMLDGILSK (SEQ ID NO: 230)
199 AFFMLDGILSKYFDL (SEQ ID NO: 231)
200 LDGILSKYFDLIYVH (SEQ ID NO: 232)
201 LSKYFDLIYVHNPVF (SEQ ID NO: 233)
202 FDLIYVHNPVFKPFE (SEQ ID NO: 234)
203 YVHNPVFKPFEKPVM (SEQ ID NO: 235)
204 PVFKPFEKPVMISMG (SEQ ID NO: 236)
205 PFEKPVMISMGNENV (SEQ ID NO: 237)
205 PVMISMGNENVLEIK (SEQ ID NO: 238)
207 SMGNENVLEIKGNDI (SEQ ID NO: 239)
208 ENVLEIKGNDIDPEA (SEQ ID NO: 240)
209 EIKGNDIDPEAVKGE (SEQ ID NO: 241)
210 NDIDPEAVKGEVLKV (SEQ ID NO: 242)
211 PEAVKGEVLKVGNKS (SEQ ID NO: 243)
212 KGEVLKVGNKSCENI (SEQ ID NO: 244)
213 LKVGNKSCENIHLHS (SEQ ID NO: 245)
214 NKSCENIHLHSEAVL (SEQ ID NO: 246)
215 ENIHLHSEAVLCTVP (SEQ ID NO: 247)
216 LHSEAVLCTVPNDLL (SEQ ID NO: 248)
217 AVLCTVPNDLLKLNS (SEQ ID NO: 249)
218 TVPNDLLKLNSELNI (SEQ ID NO: 250)
219 DLLKLNSELNIEWKQ (SEQ ID NO: 251)
220 LNSELNIEWKQAISS (SEQ ID NO: 252)
221 LNIEWKQAISSTVLG (SEQ ID NO: 253)
222 WKQAISSTVLGKVIV (SEQ ID NO: 254)
223 ISSTVLGKVIVQPDQ (SEQ ID NO: 255)
224 VLGKVIVQPDQNFT (SEQ ID NO: 256)

FIG. 14C 10  63  FLGATNYVLNEED  77  (SEQ ID NO: 262)
11  TNYVVLNEEDLGKV  81  (SEQ ID NO: 263)
30  143  RHVFPHNTAOIQSE  157  (SEQ ID NO: 264)
31  PHNTAOIQSEVHCI  161  (SEQ ID NO: 265)
50  223  KOGMELTQSYIDV  237  (SEQ ID NO: 266)
51  MFLTQSYIDVLPEP  241  (SEQ ID NO: 267)

ANTIBODIES CROSS-REACTIVE TO HUMAN AND MOUSE C-MET AND USES THEREOF

CROSS-REFERENCE TO RELATED APPLICATION AND CLAIM OF PRIORITY

This application claims the benefit of Korean Patent Application No. 10-2013-0069666, filed on Jun. 18, 2013, at the Korean Intellectual Property Office, the disclosures of which are incorporated herein in their entirety by reference.

BACKGROUND

1. Technical Field

The present invention relates to antibodies cross-reactive to human and mouse c-Met and uses thereof.

2. Description of the Related Art

Various grow factors, such as a hepatocyte growth factor (HGF), an epidermal growth factor (EGF), a vascular endothelial growth factor (VEGF), and a fibroblast growth factor (FGF), cross react with receptor tyrosine kinases (RTKs) on cellular surfaces to induce critical cell physiological regulation, such as, cell growth, differentiation, neovascularization, and tissue repair, as well as development. These growth factors and receptors, when deregulated in a physiological aspect, such as mutation, overexpression, and promotion of self activation, cause abnormal cell growth or differentiation, thereby initiating and promoting the development of cancers Lemmon M A & Schlessinger J, Cell. 141:1117-1134, 2010).

The met proto-oncogene (MET; c-Met) has been known as a proto-oncogene expressing hepatocyte growth factor (HGF)/scatter factor (SF) receptors (Dean M et al., Nature. 318:385-388, 1985, Gherardi et al., Nat. Rev. Cancer. 12:89-103, 2012), and cross-reacts with HGF, which is the only known ligand thereof, to induce mesenchymal-epithelial transition (MET) and promote cancer cell growth, invasion, and metastasis. Since c-Met is involved in mechanisms of development, metastasis, invasion, neovascularization, and the like, regardless of the ligand HGF, in the development procedure of several tumors, c-Met has been considered as an effective anti-cancer target. Based on this background, research on c-Met inhibitors, such as chemical drugs and monoclonal antibodies are being actively conducted (Comoglio P M et al., Nat. Rev. Drug. Discov. 7:504-516, 2008).

The development of antagonistic antibodies against the anticancer target c-Met is a representative strategy for anti-cancer therapy by c-Met inhibition. Anti-c-Met antibodies have been reported to inhibit the interaction between the ligand HGF and c-Met or decompose and inactivate c-Met. For example, the one-armed antagonistic antibody 'OA-5D5' developed as an anti-c-Met antibody is an agonist, and was developed as an antibody that is modified not to have an adverse effect, such as inducing c-Met dimerization (Martens T et al., Clin. Cancer Res. 15:6144-6152, 2006), and 'DN30' was developed to induce the inhibition of tumor formation by inducing the inactivation of c-Met itself to lose the function thereof (Petrelli A et al., PNAS. 103:5090-5095, 2006). However, the one-armed antagonistic antibody showed a slightly tumor suppressing effect when used alone, but a significant therapy effect when used together with chemotherapy, and the c-Met inactivating antibody was verified to be low competitive with ligand and show partial effects as an agonist. Therefore, the development of therapeutic antibodies that suppress functions of human c-Met has been continuously required.

In the development of antibodies against the anticancer target, in vitro efficacy evaluation as well as in vivo preclinical efficacy evaluation using mouse tumor models is needed. In particular, at the time of the evaluation of efficacy using mouse tumor models, therapeutic efficacies of corresponding antibodies are primarily determined through preclinical experiment results, such as the ability to reduce the confirmable tumor size and an increase in the survival period. Here, the used mouse tumor model is prepared by the injection of human-derived cancer cells overexpressing the anticancer target. In fact, it is highly possible that the correlation between preclinical and clinical results is low due to the interference of human tumor cells as well as mouse-derived cells mixed with the human tumor cells in the tumor microenvironment in the mouse at the time of the verification of antibody therapeutic effects (Talmadge J E et al., Am. J. Pathol. 170:793-804, 2007). Therefore, the combinatorial treatment of not only antibodies inhibiting only the human-derived anticancer target but also antibodies inhibiting the mouse-derived anticancer target or its ligand, or antibodies specific to human/mouse heterogeneous anticancer target can show more accurate preclinical therapy results. For example, it has been reported that, as for anti-Dll4 (delta like ligand 4) antibodies inhibiting intra-tumoral angiogenesis, when the mouse tumor model was treated with the combinatorial treatment of not only antibody against human Dll4 but also antibody against mouse Dll4, the tumor sizes were significantly reduced (Hoey T et al., Cell Stem Cell. 5:168-177, 2009). Also, as for antibodies targeting vascular endothelial growth factor receptor 2 (VEGFR-2) or vascular endothelial growth factor (VEGF), antibodies cross-reactive to human/mouse heterogeneous anticancer target exhibited high tumor inhibitory effect in the mouse tumor model, which demonstrated the necessity of the development of cross-reactive antibodies (Huang J et al., Cytotechnology. 62:61-71, 2010; Liang W-C et al., J. Biol. Chem. 281:951-961, 2006).

As described above, anti-c-Met antibodies suppressing only the function of c-Met do not have mouse c-Met receptor inhibitory action with regard to autocrine/paracrine action of human- or mouse-derived hepatocyte growth factor, and thus effects thereof are difficult to evaluate at the time of preclinical efficacy evaluation in the mouse tumor model. Since human c-Met (P08581, UniProtKB/Swiss-Prot) consists of 1,390 amino acids and mouse c-Met (P16056, UniProtKB/Swiss-Prot) consists of 1,379 amino acids, they have high amino acid sequence similarity of at least 89% therebetween (Chan A M L et al., Oncogene. 2:593-599, 1988). Also, as for the ligand hepatocyte growth factor (HGF), human HGF and mouse HGF have very high sequence similarity of at least 90% (Tashiro K et al., PNAS. 87:3200-3204, 1990). In addition, the representative sites of action of the ligand and the receptor are also the sema domain. Therefore, the possibility of development and applicability of cross-reactive antibodies is high. Therefore, it is necessary to develop antibodies cross-reactive to human/mouse c-Met, which suppress the cancer-specific ligand-receptor action in the tumoral microenvironment with regard to human/mouse c-Met, thereby confirming effective preclinical research results in the mouse tumor model.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

SUMMARY

The present inventors have endeavored to develop antibodies that can bind to human c-Met and prevent and treat cancers. As a result, the present inventors have developed novel antibodies that are cross-reactive to human c-Met and mouse c-Met and exhibit ability to inhibit cancer cell growth and neovascularization, thereby having excellent effects in preventing and treating cancers.

Accordingly, it is an object of this invention to provide an antibody or its binding fragment against human c-Met.

It is another object of this invention to provide a nucleic acid molecule encoding a heavy chain variable region of an antibody against the human c-Met.

It is another object of this invention to provide a nucleic acid molecule encoding a light chain variable region of an antibody against the human c-Met.

It is still another object of this invention to provide a recombinant vector, comprising the above-mentioned nucleic acid molecule.

It is further object of this invention to provide a host cell transformed with the recombinant vector.

It is still further object of this invention to provide a pharmaceutical composition for preventing or treating cancer.

Other objects and advantages of the present invention will become apparent from the following detailed description together with the appended claims and drawings.

In accordance with an aspect of the present invention, there is provided an antibody to human c-Met or its antigen-binding fragment, including: (a) a heavy chain variable region having the following heavy chain complementarity determining region (CDR) amino acid sequences: CDRH1 including the amino acid sequence of SEQ ID NO: 1, CDRH2 including the amino acid sequence of SEQ ID NO: 2, and CDRH3 including the amino acid sequence of SEQ ID NO: 3; and (b) a light chain variable region having the following light chain CDR amino acid sequences: CDRL1 including the amino acid sequence of SEQ ID NO: 4, CDRL2 including the amino acid sequence of SEQ ID NO:5, and CDRL3 including the amino acid sequence of SEQ ID NO: 6.

In accordance with another aspect of the present invention, there is provided an antibody to human c-Met or its antigen-binding fragment, including: (a) a heavy chain variable region having the following heavy chain complementarity determining region (CDR) amino acid sequences: CDRH1 including the amino acid sequence of SEQ ID NO: 7, CDRH2 including the amino acid sequence of SEQ ID NO: 8, and CDRH3 including the amino acid sequence of SEQ ID NO: 9; and (b) a light chain variable region having the following light chain CDR amino acid sequences: CDRL1 including the amino acid sequence of SEQ ID NO: 10, CDRL2 including the amino acid sequence of SEQ ID NO:11, and CDRL3 including the amino acid sequence of SEQ ID NO: 12.

In accordance with still another aspect of the present invention, there is provided an antibody to human c-Met or its antigen-binding fragment, including: (a) a heavy chain variable region having the following heavy chain complementarity determining region (CDR) amino acid sequences: CDRH1 including the amino acid sequence of SEQ ID NO: 13, CDRH2 including the amino acid sequence of SEQ ID NO: 14, and CDRH3 including the amino acid sequence of SEQ ID NO: 15; and (b) a light chain variable region having the following light chain CDR amino acid sequences: CDRL1 including the amino acid sequence of SEQ ID NO: 16, CDRL2 including the amino acid sequence of SEQ ID NO:17, and CDRL3 including the amino acid sequence of SEQ ID NO: 18.

BRIEF DESCRIPTION OF THE DRAWINGS

FIGS. 7A through 7J show FACS analysis results on binding affinities between c-Met overexpressing cell lines and scFv antibody fragments.

FIGS. 9A through 9G show results confirming growth inhibition aspects of respective cell lines due to the treatment with scFv antibody fragments in three c-Met expressing cell lines.

FIGS. 13A through 13C show sequences of 15-mer peptides (SEQ ID NOS: 33 to 256) derived from c-Met, used in epitope mapping.

FIGS. 14A through 14C show results confirming binding sites of respective scFv antibody fragments (SEQ ID NOS: 257 to 267) on c-Met through epitope mapping.

DETAILED DESCRIPTION

Figure 1:
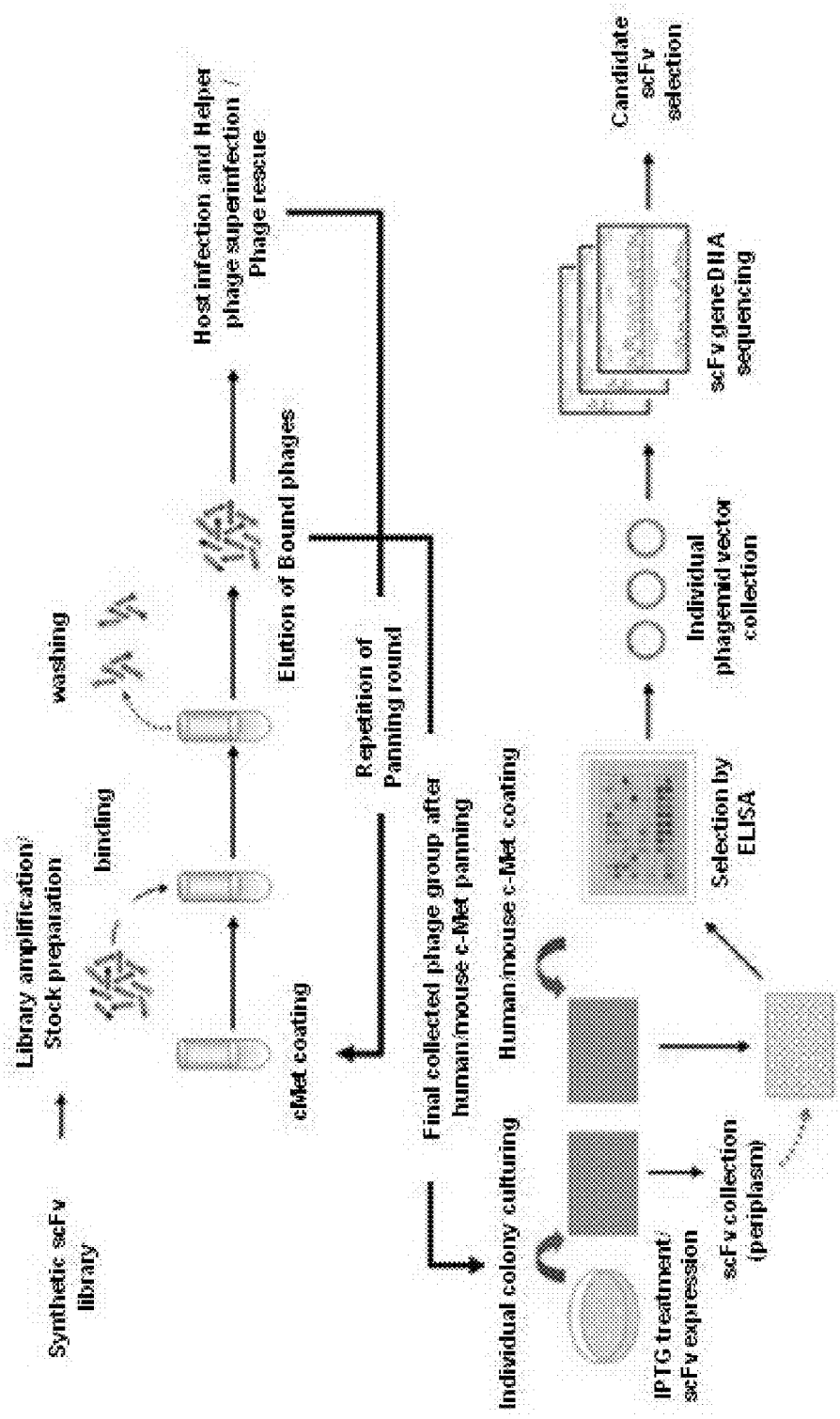
FIG. 1 shows a schematic scheme for selecting scFv antibody fragments cross-reactive to human/mouse c-Met through phage display.

The present inventors have endeavored to develop antibodies that can bind to human c-Met and prevent and treat cancers. As a result, the present inventors have developed novel antibodies that are cross-reactive to human c-Met and mouse c-Met and exhibit ability to inhibit cancer cell growth and neovascularization, thereby having excellent effects in preventing and treating cancers.

The antibodies of the present invention have a specific binding affinity to human c-Met. Particularly, the antibodies of the present invention are cross-reactive to human c-Met and mouse c-Met.

By "antibody" referred in this specification is meant an antibody which is capable of specifically binding human c-Met. Antibody is meant to include the entire antibody as well as any antibody fragments.

The entire antibody includes two full-length light chains and two full-length heavy chains, and each light chain is linked to the heavy chain by disulfide bond. The heavy chain constant region includes five different isotypes (γ, μ, α, δ and ε) of which the subclass is classified into γ1, γ2, γ3, γ4, α1 and α2. The light chain constant region includes two different isotypes (κ and λ) (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4, pp. 45-65, sinauer Associates, Inc., Sunderland, Mass. (1984)).

Antigen binding fragment refers to any antibody fragment capable of binding antigen including Fab, F(ab'), F(ab')$_2$, Fv and so on. Fab has one antigen binding site which is composed of one variable domain from each heavy and light chain of the antibody, one constant region of light chain and the first constant region ($C_{H1}$) of heavy chain. Fab' is different to Fab in the senses that there is a hinge region containing one or more cysteine residues at C-terminal of $C_{H1}$ domain of heavy chain. F(ab')2 antibody is produced by forming a disulfide bond between cysteine residues of hinge region of Fab'. Fv is a minimal antibody fragment including one variable region from each heavy and light chain and recombinant technique to prepare a Fv fragment is disclosed in PCT WO 88/10649, PCT WO 88/106630, PCT WO 88/07085, PCT WO 88/07086 and PCT WO 88/09344.

Two-chain Fv is linked by non-covalent bond between one variable region of each heavy and light chain, and single-chain Fv is generally linked by covalent bond via a peptide linker between one variable region of each heavy and light chain or is directly linked to each other at C-terminal, forming a dimer such as two-chain Fv. Such antibody fragments may be obtained using a proteolytic enzymes (e.g., a whole antibody is digested with papain to produce Fab fragments, and pepsin treatment results in the production of F(ab')2 fragments), and may be preferably prepared by genetic recombination techniques.

Preferably, the antibody in this invention is a form of scFv or entire antibody. In addition, the heavy chain constant region is selected from the isotypes consisting of γ, μ, α, δ or ε.

The term "heavy chain" refers to both a full-length heavy chain and its part, which includes variable domain ($V_H$) containing the amino acid sequence with a variable region sequence for specifically binding to antigen and three constant domains ($C_{H1}$, $C_{H2}$ and $C_{H3}$). The term "light chain" refers to both a full-length light chain and its part, which includes variable domain (VL) containing the amino acid sequence with a variable region sequence for specifically binding to antigen and constant domain ($C_L$).

The "CDR (complementarity determining region)" means an amino acid sequence of hypervariable region of immunoglobulin heavy and light chain (Kabat et al., *Sequences of Proteins of Immunological Interest*, 4th Ed., U.S. Department of Health and Human Services, National Institutes of Health (1987)). Three CDRs are involved in heavy chain ($C_{H1}$, $C_{H2}$ and $C_{H3}$) and light chain ($CDR_{L1}$, $CDR_{L2}$ and $CDR_{L3}$), respectively. CDR provides a main contacting residue to combine antibody with antigen or epitope.

Human c-Met antibody or its antigen-binding fragment may include analogs of amino acid sequences set forth in the appended Sequence Listing, which are capable of specifically recognizing human c-Met. For example, amino acid sequence of antibody may be altered to improve binding affinity and/or other biological characteristics of antibody, for example including the alterations prepared by deletion, insertion and/or substitution of amino acid residues of antibody.

Such amino acid variations may be provided on the basis of a relative similarity of amino acid side chains, e.g., hydrophobicity, hydrophilicity, charge and size. By the analysis for size, shape and type of the amino acid side chains, it could be clear that all of arginine, lysine and histidine residues are those having positive charge; alanine, glycine and serine have a similar size; phenylalanine, tryptophan and tylosin have a similar shape. Accordingly, based on these considerable factors, arginine, lysine and histidine; alanine, glycine and serine; and phenylalanine, tryptophane and tylosin may be considered to be biologically functional equivalents.

For introducing mutation, a hydropathic index of amino acids may be considered. Based on the hydrophobicity and the charge, the hydropathic index is given to each amino acid: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophane (−0.9); tylosin (−1.3); proline (−1.6); histidine (−3.2); glutamate (−3.5); glutamine (−3.5); aspartate (−3.5); asparagin (−3.5); lysine (−3.9); and arginine (−4.5).

For providing an interactive biological function of proteins, the hydropathic index of the amino acid is very important. It is well known to one of skill in the art that variations can possess a similar biological activity only where proteins are replaced with amino acids having similar hydropathic index. Where variations are intended to introduce based on the hydropathic index, the substitution is preferably performed between amino acid residues having no more than ±2 difference in hydropathic index values more preferably within ±1, much more preferably within ±0.5.

It would be also obvious to those of skill in the art that substitutions of amino acids with other amino acids having similar hydrophilicity values may result in the generation of variants having biologically equivalent activities. As disclosed in U.S. Pat. No. 4,554,101, each amino acid residue is assigned the following hydrophilicity values: arginine (+3.0); lysine (+3.0); aspartate (+3.0); glutamate (+3.0); serine (+0.3); asparagin (+0.2); glutamine (+0.2); glycine (0); threonine (−0.4); proline (−0.5); alanine (−0.5); histidine (−0.5); cysteine (−1.0); methionine (−1.3); valine (−1.5); leucine (−1.8); isoleucine (−1.8); tylosin (−2.3); phenylalanine (−2.5); tryptophane (−3.4).

Where variations are intended to introduce based on the hydrophilicity values, the substitution is preferably performed between amino acid residues having no more than ±2 difference in hydropathic index values more preferably within ±1, much more preferably within ±0.5.

The alteration of amino acid residues not to substantially impair protein activity is well known to one skilled in the art (H. Neurath, R. L. Hill, The Proteins, Academic Press, New York, 1979). Such amino acid alteration includes Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, but not limited to.

Considering the afore-mentioned variations having biologically equivalent activities, it could be understood that either antibody of this invention or the nucleic acid encoding the same includes substantially identical sequences to the sequences set forth in the appended Sequence Listing. The substantially identical sequences refers to those showing preferably at least 61%, more preferably at least 70%, still more preferably at least 80%, most preferably at least 90% nucleotide similarity to the sequences of the appended Sequence Listing, as measured using one of the sequence comparison algorithms. Methods of alignment of sequences for comparison are well-known in the art. Various programs and alignment algorithms are described in: Smith and Waterman, *Adv. Appl. Math.* 2:482 (1981); Needleman and Wunsch, *J. Mol. Bio*. 48:443 (1970); Pearson and Lipman, *Methods in Mol. Biol*. 24: 307-31 (1988); Higgins and Sharp, *Gene* 73:237-44 (1988); Higgins and Sharp, *CABIOS* 5:151-3 (1989); Corpet et al., *Nuc. Acids Res*. 16:10881-90 (1988); Huang et al., *Comp. Appl. BioSci*. 8:155-65 (1992); and Pearson et al., *Meth. Mol. Biol*. 24:307-31 (1994). The NCBI Basic Local Alignment Search Tool (BLAST) (Altschul et al., *J. Mol. Biol*. 215: 403-10 (1990)) is available from several sources, including the National Center for Biological Information (NBCI, Bethesda, Md.) and on the Internet, for use in connection with the sequence analysis programs blastp, blasm, blastx, tblastn and tblastx.

In addition, sequencing of framework region (FR) and CDRs in antibody variable regions may be indicated based on the sequences of IMGT generally accessible in the art.

According to an embodiment, the heavy chain variable region of 1F12 antibody includes the amino acid sequence of SEQ ID NO:19.

According to an embodiment, the light chain variable region of 1F12 antibody includes the amino acid sequence of SEQ ID NO:20.

According to an embodiment, the heavy chain variable region of 2A01 antibody includes the amino acid sequence of SEQ ID NO:21.

According to an embodiment, the light chain variable region of 2A01 antibody includes the amino acid sequence of SEQ ID NO:22.

According to an embodiment, the heavy chain variable region of 2C03 antibody includes the amino acid sequence of SEQ ID NO:23.

According to an embodiment, the light chain variable region of 2C03 antibody includes the amino acid sequence of SEQ ID NO:24.

The antibody of this invention includes, but not limited to, monoclonal antibody, polyclonal antibody, human antibody, humanized antibody, chimeric antibody, single-chain Fvs (scFV), single-chain antibody, Fab fragment, F(ab') fragment, disulfide-linked Fvs (sdFV) and anti-idiotype (anti-Id) antibody, and epitope-binding fragment thereof.

The antibody of the present invention is basically composed of "heavy chain variable region (VH)-linker—light chain variable region (VL)". In the scFv antibody of the present invention, the linker refers to an amino acid sequence having a predetermined length which artificially links the heavy chain and light chain variable regions.

The scFv antibody of the present invention may be expressed by VH (SEQ ID NO: 19)—linker (SEQ ID NO: 25)—VL (SEQ ID NO: 20); VH (SEQ ID NO: 21)—linker (SEQ ID NO: 25)—VL (SEQ ID NO: 22); and VH (SEQ ID NO: 23)—linker (SEQ ID NO: 25)—VL (SEQ ID NO: 24).

The antibody or its antigen-binding fragment of the present invention is specifically cross-reactive to human c-Met and mouse c-Met. Since the antibody or its antigen-binding fragment of the present invention is capable of specifically binding to human c-Met as well as mouse c-Met, more accurate preclinical results can be confirmed in the efficacy evaluation using mouse tumor models.

In another aspect of this invention, there is provided a nucleic acid molecule encoding a heavy chain variable region of an antibody against the human and mouse c-Met comprising the amino acid sequence of SEQ ID NO:19, SEQ ID NO:21 or SEQ ID NO:23.

In still another aspect of this invention, there is provided a nucleic acid molecule encoding a light chain variable region of an antibody against the human and mouse c-Met comprising the amino acid sequence of SEQ ID NO:20, SEQ ID NO:22 or SEQ ID NO:24.

The term "nucleic acid molecule" comprehensively refers to a deoxyribonucleotide (gDNA and cDNA) or ribonucleotide polymer, and the basic nucleotides of nucleic acid molecule also include analogues with modified sugar or base as well as natural nucleotides (Scheit, *Nucleotide Analogs*, John Wiley, New York (1980); Uhlman and Peyman, *Chemical Reviews*, 90:543-584 (1990)). The sequence of the present nucleic acid molecule encoding the variable region of heavy and light chain could be modified. Such modification includes addition, deletion or non-conservative or conservative substitution of nucleotide.

According to an embodiment, the nucleic acid molecule encoding the variable region of heavy chain includes the nucleotide sequence of SEQ ID NO:26, SEQ ID NO:28 or SEQ ID NO:30.

According to an embodiment, the nucleic acid molecule encoding the variable region of light chain includes the nucleotide sequence of SEQ ID NO:27, SEQ ID NO:29 or SEQ ID NO:31.

The nucleic acid molecule of this invention encoding an human c-Met antibody also includes a nucleotide sequence sharing substantial homology with the above nucleotide sequence. The substantial homology means the nucleotide sequence sharing homology of at least 80%, more preferably 90% and most preferable 95% by sequence alignment analysis using maximal alignment between the nucleotide sequence of this invention and other random sequences and algorithm ordinarily known to those skilled in the art.

In still further aspect of this invention, there is provided a recombinant vector comprising the above-described nucleic acid molecules.

The term "vector" is a tool for expressing a target gene in a host cell, including a plasmid vector; a cosmid vector; and a virus vector such as a bacteriophage vector, an adenovirus vector, a retrovirus vector and an adeno-associated virus vector, and preferably a plasmid vector.

According to a preferable embodiment, the nucleic acid molecules encoding the variable region of light and heavy chain are operatively linked to a promoter.

The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The vector system of this invention may be performed by various methods known to those skilled in the art and its practical method is described in Sambrook et al., Molecular Cloning, A Laboratory Manual, Cold Spring Harbor Laboratory Press (2001), which is herein incorporated by reference.

Typically, the vector of this invention may be constructed as cloning or expression vector. In addition, the vector of this invention may be constructed using a prokaryotic or eukaryotic cell as a host cell.

For instance, in each a vector of this invention and an eukaryotic cell used as an expression vector and the host cell, the promoter derived from genome of animal cell (example: methallothionein promoter, β-actin promoter, human hemoglobin promoter and human muscle creatine promoter) or mammalian virus (example: adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of moloney virus, Epstein barr virus (EBV) and Rous sarcoma virus (RSV)) might be used, and polyadenylated sequence might be commonly used as the transcription termination sequence.

The vector of this invention could be fused with other sequences to purify an antibody expressed from it. For example, a fused sequence includes glutathione-S-transferase (Pharmacia, USA), maltose-binding protein (NEB, USA), FLAG (IBI, USA) and 6×His (hexahistidine; Quiagen, USA) and so on. Since the protein expressed in the vector of the present invention is antibody, expressed antibody could be also purified throughout protein A column in an easy manner without additive sequences for purification.

On the other hand, the expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

In still another aspect of this invention, there is provided a host cell transformed with the above-described recombinant vector.

The host cells in which the present vector is stably and successively cloned and expressed, also utilize any one known to those skilled in the art, for example the suitable eukaryotic host cell of the above vector includes COS7 cell (monkey kidney cell), NSO cell, SP2/0, CHO (Chinese hamster ovary) cell, W138, BHK (baby hamster kidney) cell, MDCK, myeloma cell line, HuT 78 cell and 293 cell, but not limited to.

In another aspect of this invention, there is provided a pharmaceutical composition for preventing or treating cancer, comprising: (a) a therapeutically effective amount of an antibody or its binding fragment against a human c-Met; and (b) a pharmaceutically acceptable carrier.

A pharmaceutical composition of the present invention uses, as an active ingredient, the antibody to human c-Met or its antigen-binding fragment of the present invention. Therefore, the overlapping descriptions therebetween are omitted to avoid excessive complication of the specification due to repetitive descriptions thereof.

As can be verified by the following examples, the antibody to human c-Met of the present invention inhibits the growth of cancer cells derived from various cancers by a considerable binding affinity to c-Met and the suppression of c-Met function therefrom, inhibits the phosphorylation of c-Met and downstream signaling molecules to suppress c-Met signaling, and inhibits neovascularization. Therefore, the antibody of the present invention is very useful in the prevention and treatment of cancers.

The cancers that can be prevented or treated by the composition of the invention may include various cancers known in the art, and examples thereof may include breast cancer, colon cancer, lung cancer, stomach cancer, liver cancer, blood cancer, bone cancer, pancreatic cancer, skin cancer, brain cancer, cervical cancer, nasopharyngeal cancer, laryngeal cancer, colon cancer, ovarian cancer, rectal cancer, colorectal cancer, vaginal cancer, small intestine cancer, endocrine cancer, thyroid cancer, parathyroid cancer, ureter cancer, urinary tract cancer, prostate cancer, bronchial cancer, bladder cancer, kidney cancer, and marrow cancer.

Specifically, the cancers that can be prevented or treated by the composition of the invention are c-Met expressing cancers.

In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered via the parenteral. When the pharmaceutical composition of the present invention is administered parenterally, it can be done by intravenous, subcutaneous, intramuscular or intraperitoneal.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.001-100 mg/kg (body weight). The term "pharmaceutically effective amount" refers to an amount suitable to prevent or treat cancer According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

Features and advantages of one or more embodiments of the present invention are summarized as follows:

(a) The antibody of the present invention has high specificity to human c-Met and is cross-reactive also to mouse c-Met.

(b) Since the antibody or its antigen-binding fragment of the present invention is capable of specifically binding to human c-Met as well as mouse c-Met, more accurate preclinical results can be confirmed in the efficacy evaluation using mouse tumor models.

(c) The antibody of the present invention inhibits the growth of cancer cells derived from various cancers by a considerable binding affinity to c-Met and the suppression of c-Met function therefrom, inhibits the phosphorylation of c-Met and downstream signaling molecules to suppress c-Met signaling, and inhibits neovascularization, thereby being very efficient in the prevention and treatment of cancers.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Phage Display Screening for Identification of Anti-c-Met scFv Antibody Fragment

The scFv antibody fragments cross-reactive to human/mouse c-Met were identified through phage display screening by using the existing constructed synthetic scFv phage library (Yang et al., Mol. Cells. 27:225-235, 2009). The phage display screening procedure was as shown in FIG. 1.

Specifically, for the collection of phagemid vectors in a phage type, which were introduced into E. coli host ER2537, four lower sub-library samples were respectively added to 400 ml of media (SB/ampicillin/2% glucose), and then cultured for about 2 hours. The host cells cultured until $OD_{600}=0.5$ were centrifuged at 5,000 g for 20 minutes to remove the supernatant, and then suspended in 400 ml of secondary media (SB/ampicillin). Then, $10^{12}$ pfu (plaque forming unit) of helper phage (VCSM13) was added, again followed by culturing for 1 hour. After that, the antibiotic Kanamycin (antibiotic gene introduced into helper phage) was added at a concentration of 70 μg/ml, followed by culturing overnight at 30° C., so that the phage library was extracellulary produced. Then, the centrifuged culture was treated with the polyethylene glycol (PEG) solution to precipitate only phage particles, thereby collecting the phage library. For the count of the phages collected from each sub-library, each sample was diluted and used for infection of host cells (ER2537). The phages were counted in the LB/ampicillin media.

Phage display screening was performed through repeated rounds of panning. The counted sub-libraries were collected to $2.0 \times 10^{12}$ pfu, and then treated with the immunotube coated with c-Met-Fc protein diluted to 10 μg/ml in TBS. The immunotube and the phage particles before the treatment were treated with a blocking solution containing 3% skim milk for 1 hour, thereby preventing non-specific binding thereof except for c-Met. The phage libraries were treated with c-Met for 1 hour, and then the immunotube was washed with 0.1% Tween 20 in PBS (TBST). Then, 1 ml of 100 mM triethyl amine was added thereto and kept to stand for 10 minutes, so that phage particles bound to c-Met were removed and collected. For the confirmation of the number of collected phages (output), the collected solution was diluted and used for infection of the host cells, and then phage counting was performed in the medium. The remaining collected solution was plated on the 15 cm-media and then cultured, and then 5 ml of SB medium (50% glycerol) was added, followed by collection and storage (−80° C.) of colonies.

For the continuous rounds of panning, 50 μl of aliquot was taken from the stored phage solution from the previous round of panning, and subjected to phage particle amplification. The phage particles which were cultured in the host cells, added with helper phages, and collected, were prepared by PEG precipitation, and the next round of panning progressed using the phage particles by the same method as the previous round of panning. A total of four rounds of panning with mouse c-Met were progressed. After the phages collected in the fourth round of panning were again amplified, further two rounds of panning with human c-Met were performed. Phage display screening results were shown in FIG. 1.

TABLE 1

| Phage display screening for mouse (M) and human (H) c-Met (cfu/ml) | | | | |
|---|---|---|---|---|
| Round | 1st | 2nd | 3rd | 4th |
| M-Input | $2.1 \times 10^{12}$ | $2.3 \times 10^{12}$ | $2.6 \times 10^{12}$ | $2.8 \times 10^{12}$ |
| M-Output | $7.2 \times 10^{6}$ | $4.7 \times 10^{7}$ | $3.8 \times 10^{7}$ | $1.1 \times 10^{8}$ |
| H-Input | $1.2 \times 10^{11}$ | $6.2 \times 10^{11}$ | — | — |
| H-Output | $1.7 \times 10^{7}$ | $4.9 \times 10^{7}$ | — | — |

Example 2

Sequencing and ELISA Analysis for Anti-c-Met scFv Candidate Selection and ELISA Selection After a total of six rounds of panning with mouse/human c-Met were finished, the phage particles collected from the final round of panning were confirmed as colonies in the medium through infection of host cells. These colonies were taken and inoculated in a 96 well plate containing 200 μl of SB/ampicillin media and then cultured (37° C., within 3 hours). After that, for the induction of scFv-pIII protein expression, 1 mM final concentration IPTG was added to each well, followed by culturing overnight at 30° C. After that, the cultured plate was centrifuged to discard the supernatant. Then, for the collection of periplasmic fractions from the cultured cells in each well, the culture plate was treated with 40 μl of TES solution (20% w/v sucrose, 50 mM Tris, 1 mM EDTA, pH 8.0) maintained at 4° C., and then kept to stand at 4° C. for 30 minutes, so that the cells were lysed. After that, the cells were treated with 60 μl of 0.2×TES solution, and then kept to stand for 30 minutes. Finally, the plate was centrifuged and the supernatant was collected, thereby producing scFv-pIII protein on a small scale.

Figure 2:
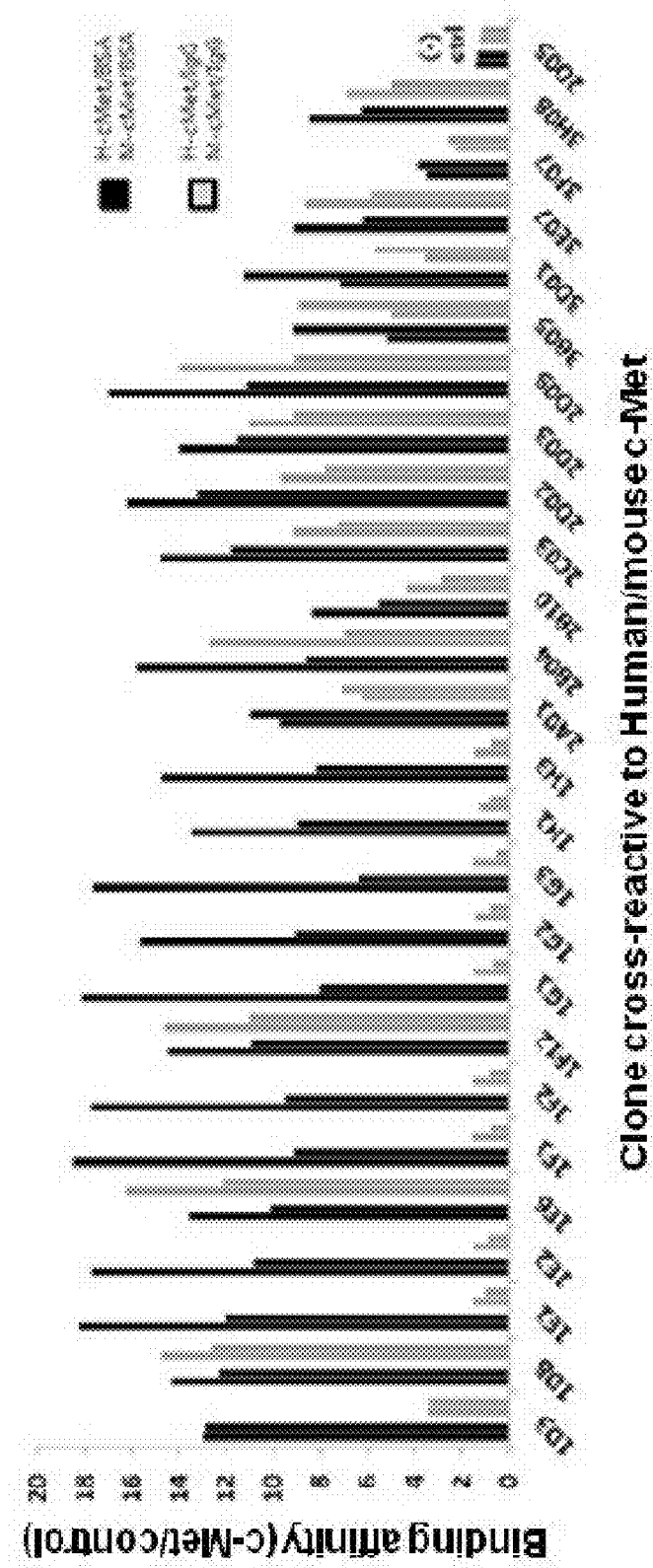
FIG. 2 shows binding affinities of 25 scFv antibody fragments cross-reactive to human/mouse c-Met.

At the same time, a 96 well plate coated with human or mouse c-Met-Fc protein was prepared, and then 25 μl of aliquot was taken from the collected periplasmic fractions and added to each well, followed by binding for 1 hour. Then, after three or four times of washing procedures were performed using TBST, anti-HA-HRP antibody was added, followed by binding for 1 hour. The plate was again washed, followed by induction of a color development reaction (TMB substrate), and then the values of color development were measured at O.D. 450 nm. A total of 282 colons were analyzed, and 25 colons (binding affinity >2-fold) out of them showed a higher binding affinity to human/mouse c-Met (FIG. 2). Since antibody in which c-Met extracellular domain binds to Fc region of IgG was used at the time of the panning, commercialized antibody (Erbitux) or BSA protein was used as a control group in order to exclude the phage particles that bind to Fc region. Resultantly, it was verified that the cross-reactive affinities of respective clones to human/mouse c-Met were on average about 10-fold as compared with that of the control group.

For the scFv sequencing, phagemid DNA was collected from each clone, and DNA sequence analysis thereof was requested. As a result, it was verified that scFv sequences of clones 1D03/1D08/1E06/1F12/2B04/2D02/2DC09/3E07/3H08 were identical, and, also, scFv sequences of clones 2A01/2B10 and 2C03/3B05 were identical to each other. Considering that nine, two, and two clones out of a total of 25 colons were verified to have identical scFv sequences, respectively, the scFv antibody fragments having these sequences have higher binding affinities to specific epitope in the c-Met extracellular domain, and thus largely selected in the screening procedure. Through this, three scFv antibody fragments cross-reactive to human/mouse c-Met were identified. 2D05 clones that had no specific biding affinity to human/mouse c-Met was used as a control for further evaluation of functions of the three scFv antibody fragments.

TABLE 2

Heavy chain FR/CDR sequences of scFv antibody fragments cross-reactive to human/mouse c-Met

| Clone (V-gene family) | 1F12 (IGHV3) | 2A01 (IGHV3) | 2C03 (IGHV3) |
|---|---|---|---|
| FR1 | EVQLLESGGGLVQPGGSLRLSCAAS (SEQ ID NO: 268) | EVQLLESGGGLVQTGGSLRLSCAAS (SEQ ID NO: 275) | EVQLLESGGGLVQPGGSLRLSCAAS (SEQ ID NO: 282) |
| CDR1 | GFTFSNYA (SEQ ID NO: 269) | GFTFSSYD (SEQ ID NO: 276) | GFTFSNYA (SEQ ID NO: 283) |
| FR2 | MSWVRQAPGKGLEWVSG (SEQ ID NO: 270) | MSWVRRAPGKGLEWVSW (SEQ ID NO: 277) | MSWVRQAPGKGLEWVSA (SEQ ID NO: 284) |
| CDR2 | ISYSGGST (SEQ ID NO: 271) | ISHGGSSI (SEQ ID NO: 278) | ISYDSGSI (SEQ ID NO: 285) |
| FR3 | YYADSVKGRFTISRDNSKNTLYLQMNSLRAEDTAVYYC (SEQ ID NO: 272) | SYADSVKGRFTISRDNSKNTLYLQMNSLRAEDTAVYYC (SEQ ID NO: 279) | YYADSVKGRFTISRDNSKNTLYLQMNSLRAEDTAVYYC (SEQ ID NO: 286) |
| CDR3 | AKASRSCQRPACSYANGMDV (SEQ ID NO: 273) | AKDAYPIRQETFDY (SEQ ID NO: 280) | AKAARSCRNWSCSYANGMDV (SEQ ID NO: 287) |
| FR4 | WGQGTLVTVSS (SEQ ID NO: 274) | WGQGTLVTVSS (SEQ ID NO: 281) | WGQGTLVTVSS (SEQ ID NO: 288) |

TABLE 3

Light chain FR/CDR sequences of scFv antibody fragments cross-reactive to human/mouse c-Met

| Clone (V-gene family) | 1F12 (IGLV1) | 2A01 (IGLV1) | 2C03 (IGLV1) |
|---|---|---|---|
| FR1 | QSVLTQPPSASGTPGQRVTISCTGS (SEQ ID NO: 289) | QSVLTQPPSASGTPGQRVTISCSGS (SEQ ID NO: 295) | QSVLTQPPSASGTPGQRVTISCTGS (SEQ ID NO: 301) |
| CDR1 | SSNIGNNY (SEQ ID NO: 290) | SSNIGNND (SEQ ID NO: 296) | SSNIGSNY (SEQ ID NO: 302) |
| FR2 | VTWYQQLPGTAPKLLIY (SEQ ID NO: 291) | VSWYQQLPGTAPKLLIY (SEQ ID NO: 297) | VSWYRQLPGTAPKLLIY (SEQ ID NO: 303) |
| CDR2 | YNN | PDS | SDS |
| FR3 | HRPSGVPDRFSGSKSGTSASLAISGLQSEDEADYYC (SEQ ID NO: 292) | QRPSGVPDRFSGSKSGTSASLAISGLRSEDEADYYC (SEQ ID NO: 298) | NRPSGVPDRFSGSKSGTSASLAISGLRSEDEADYYC (SEQ ID NO: 304) |
| CDR3 | GSWDYSLSAYV (SEQ ID NO: 293) | ASWDSSLSGYV (SEQ ID NO: 299) | GSWDDSLSGYV (SEQ ID NO: 305) |

TABLE 3-continued

Light chain FR/CDR sequences of scFv antibody fragments cross-reactive to human/mouse c-Met

| Clone (V-gene family) | 1F12 (IGLV1) | 2A01 (IGLV1) | 2C03 (IGLV1) |
|---|---|---|---|
| FR4 | FGGGTKLTVL (SEQ ID NO: 294) | FGGGTKLTVL (SEQ ID NO: 300) | FGGGTKLTVL (SEQ ID NO: 306) |

Example 3

Verification on Binding Affinity to c-Met Using Anti-c-Met scFv Labeled Phages

Figure 3A:
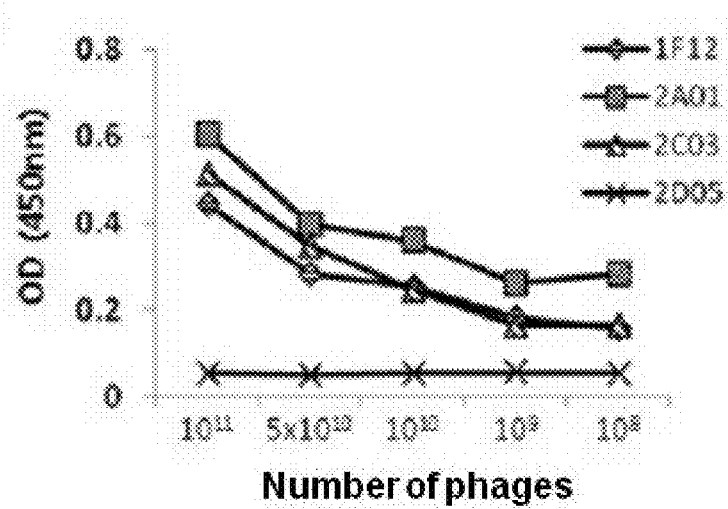
FIGS. 3A and 3B show phage-ELISA results using respective phage particles labeled by three anti-c-Met scFv antibody fragments.
Figure 3B:
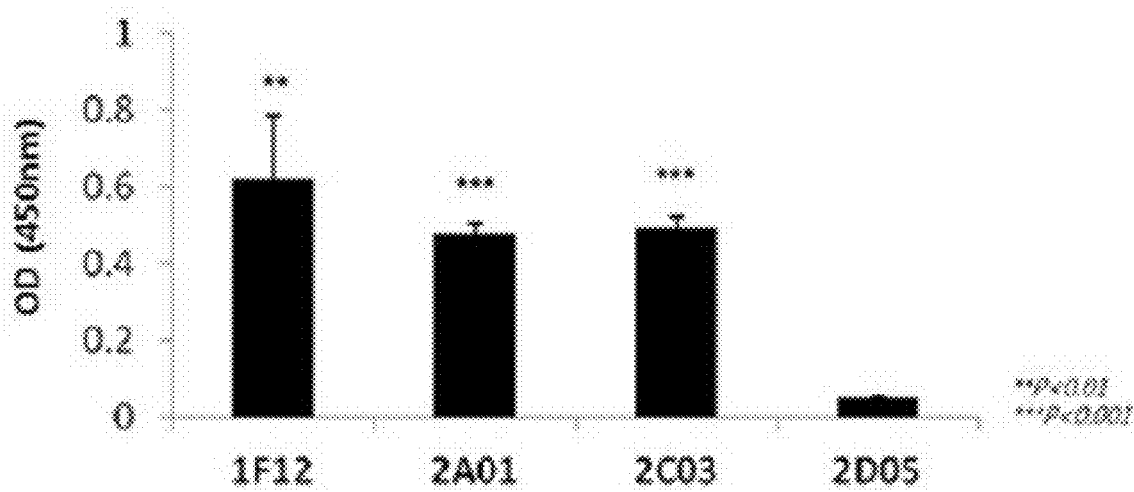

Since the three scFV antibody fragments were selected by phage display screening, their binding affinities to c-Met were first confirmed while they are expressed in the phage structure. Respective phage particles labeling three scFV antibody fragments were individually collected, and counted according to clones (1F12: 2.58×1012 pfu, 2A01: 8.1×1011 pfu, 2C03: 8.5×1011 pfu, 2D05: 1.49×1012 pfu). After that, a 96-well plate coated with human c-Met was treated with dilutions of phage particles according to concentrations, to verify their binding affinities through ELISA analysis using anti-phage antibody. As a result, it was verified that as the number of phage particles decreases, the binding affinity tends to decrease, and thus the specificity to c-Met depending on the number of phage particles can be confirmed (FIG. 3A). Also when the plate was treated with each phage having a predetermined number of phage particles (1×1010 pfu/well), the respective phage clones were verified to show statistically significant high binding affinities as compared with the control phage (2D05) (FIG. 3B). Therefore, it was verified that the respective scFV antibody fragments selected based on the binding affinity to c-Met in the screening procedure showed binding affinities to c-Met even while they are labeled in the phage structure bodies.

Example 4

Figure 4A:
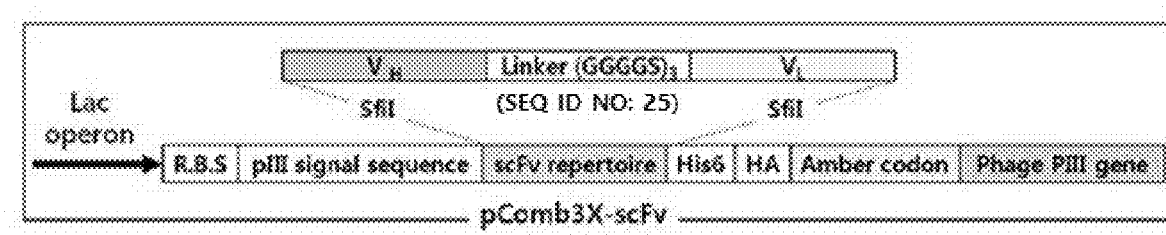
FIGS. 4A and 4B show a map of phagemid vector for production of scFv antibody fragment having the linker (SEQ ID NO: 25) and Coomassie staining results of respective scFv antibody fragments expressed/purified actually.

Production of Anti-c-Met scFv Proteins and Verification on Binding Affinity Thereof to c-Met For the verification of binding affinity and function of scFv alone, expression and purification were conducted by using the protein expression strain (TOP10F'). The basic structure of phagemid can be confirmed in FIG. 4A. The host cells (ER2537) containing screened phagemid suppress the transcription stop codon (amber codon, UAG) between scFv and the pIII protein of the phage. Since expression of scFv alone is not possible therein, the expression strain (TOP10F'), which is the non-suppressor strain, was used.

Figure 4B:
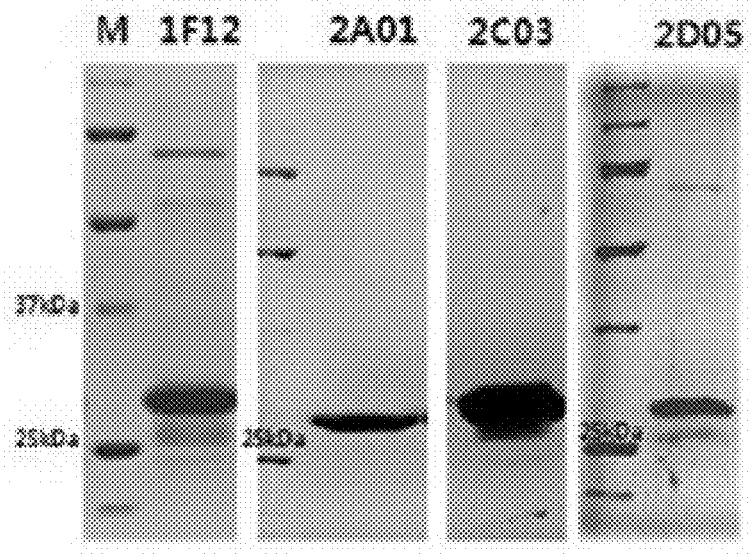

Specifically, phagemid coding each antibody fragment was collected from the host cells, and then introduced into the expression strain. After that, the expression strains into which respective phagemids were successfully introduced were confirmed through DNA sequencing. A single colony was taken from the expression strains to which scFv was introduced, and inoculated in 3 ml of LB/ampicillin media, followed by culturing at 37° C. overnight. After the culturing overnight, the culture solution was transferred to 400 ml of media (SB/ampicillin), and then further cultured until $OD_{600}$=0.5 to 0.5. 1 mM final concentration IPTG was added, again followed by culturing overnight at 30° C. After the culture solution was centrifuged, the expression hosts were lysed in 40 ml of TES solution, and then the periplasmic fractions were collected. The collected culture solution was filtered through 0.45 μm filter. The scFv protein in the filtered lysate was allowed to bind to 1.2 ml of Ni-NTA beads (Qiagen), which were added for His-tag purification, at room temperature for 1 hour, and then packed in the gravity column (Bio-rad), followed by wash and collection using an imidazole solution. SDS-PAGE and Coomassie blue staining results after expression and purification of each clone were shown in FIG. 4B. Each scFv was verified to have a size of about 28 kDa. The concentration of each purified scFv was determined by Bradford protein assay. Then, the purified scFv were stored, and used for later experiments.

Figure 5A:
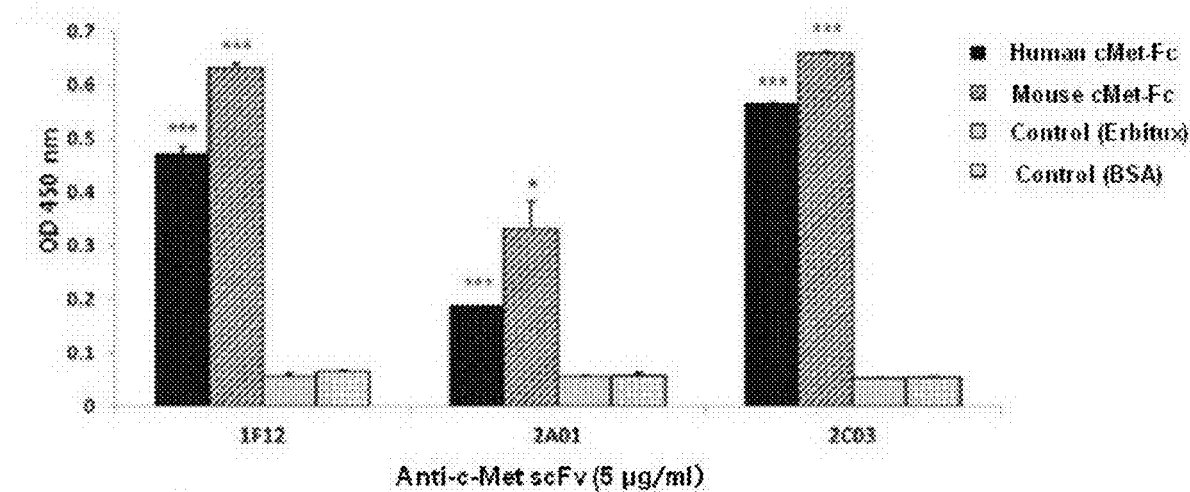
FIGS. 5A and 5B show cross-reactive affinities to human/mouse c-Met and binding affinities to c-Met extracellular domain for scFv antibody fragment proteins.
Figure 5B:
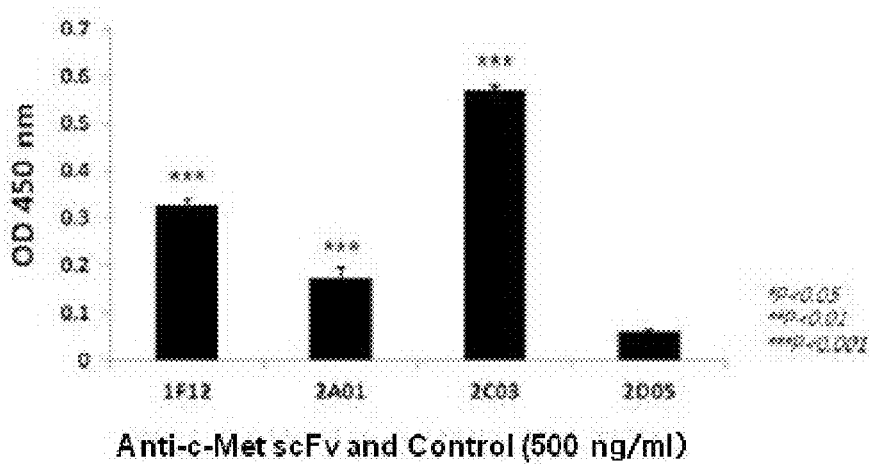

By using the produced scFv protein, the binding affinity to human/mouse c-Met extracellular domain+Fc protein was confirmed through ELISA. Human/mouse c-Met coated on a 96-well plate were treated with 5 μg/ml of scFv proteins (1F12, 2A01, 2C03, and 2D05), followed by binding at room temperature for 1 hour. After that, the plate was washed three times with 0.1% TBST solution, and then treated with anti-HA-HRP antibody for 1 hour, to detect the scFv proteins that bind to c-Met. After that, the plate was washed three times, and then treated with 10 μl of TMB substrate, followed by standing for 5 minutes. The reaction was stopped by using sulfuric acid solution, and then the absorbance was determined by ELISA reader. As a result, it was verified that each scFv protein had significant binding affinity to human and mouse c-Met proteins as compared with the control group (IgG, BSA) (FIG. 5A). In addition, after the cells were treated with 500 ng/ml of each scFv protein using human c-Met protein to which Fc region was not bound, the same ELISA assay was conducted. Similarly, the degrees of binding affinity of the respective scFv proteins were slightly different, but all the scFv proteins successfully showed specificity to c-Met extracellular domain.

Example 5

Figure 6A:
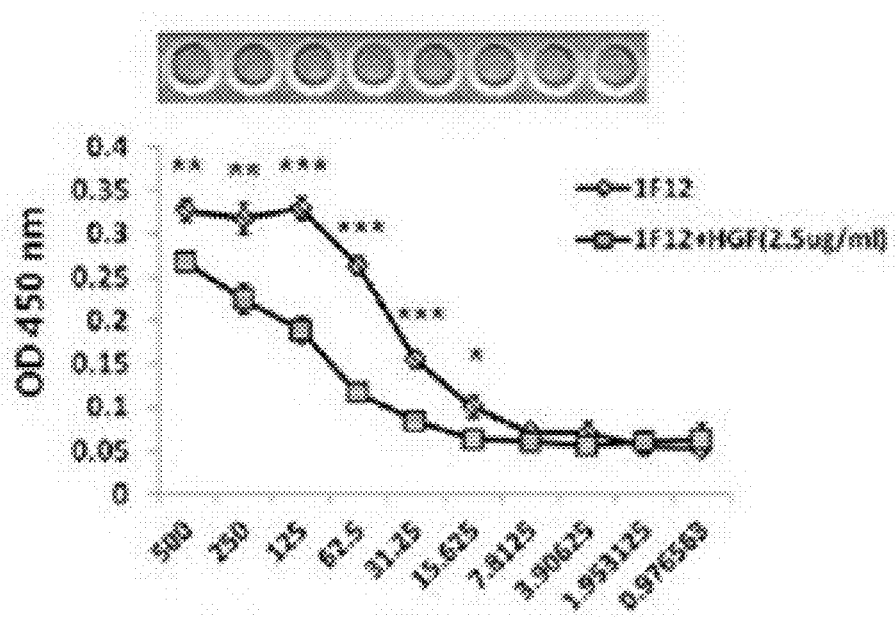
FIGS. 6A through 6C show ELISA results confirming competitive reactions of anti-c-Met scFv antibody fragments with the ligand hepatocyte growth factor (HGF).
Figure 6B:
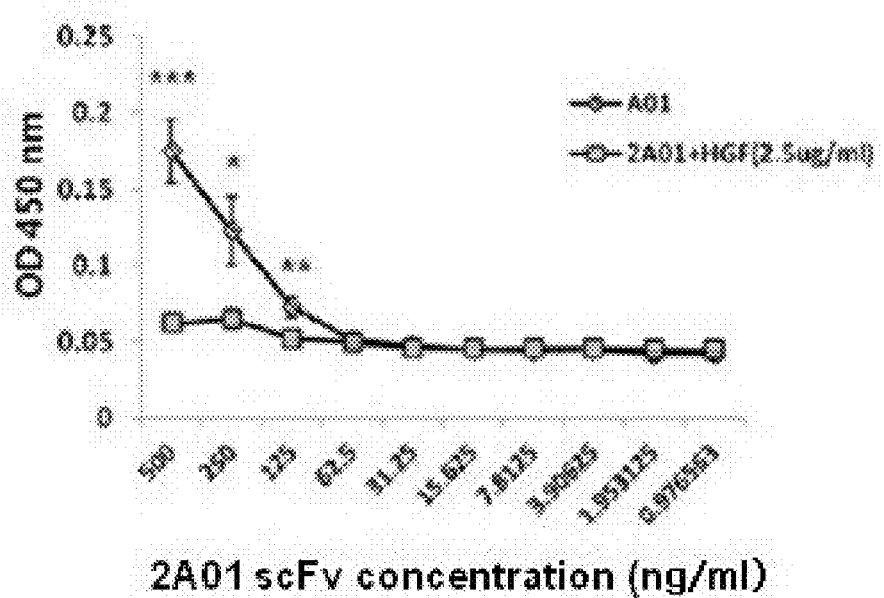
Figure 6C:
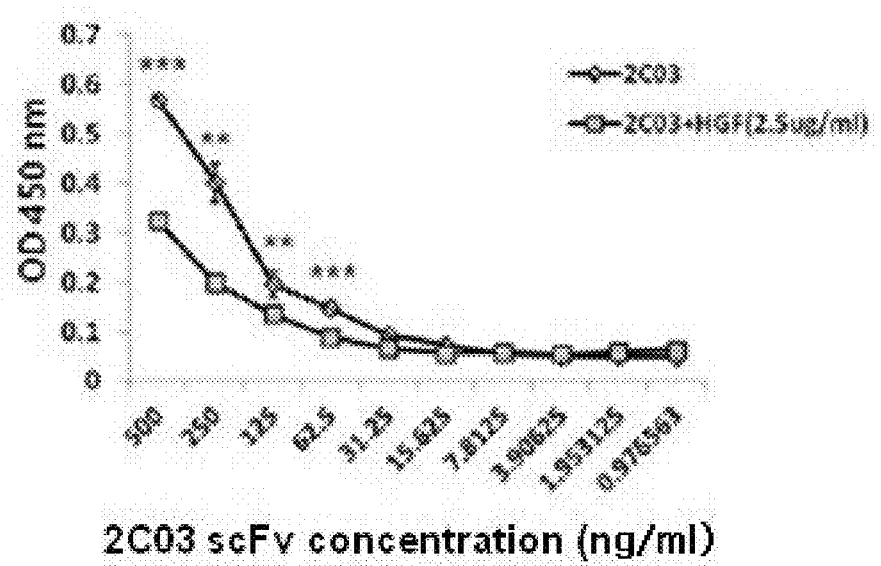
Figure 7A:
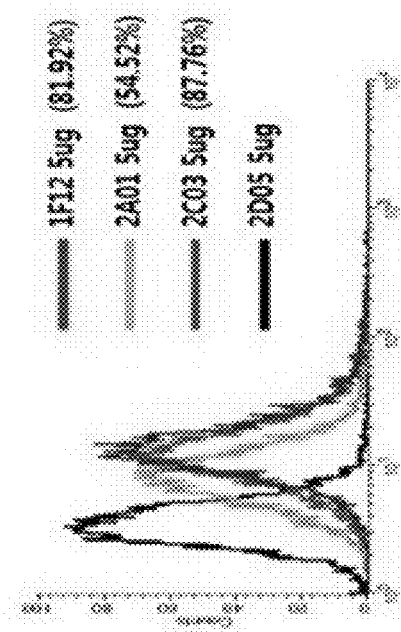
Figure 7C:
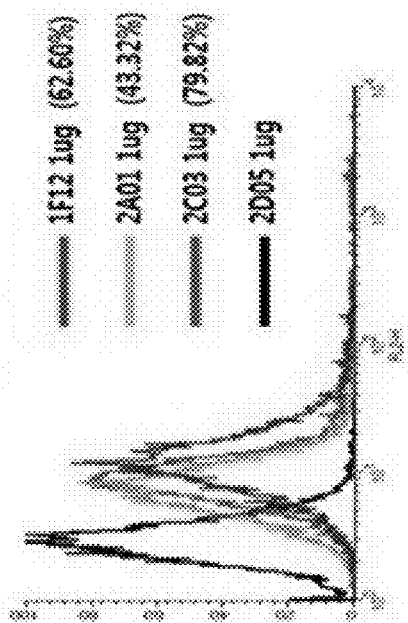
Figure 7B:
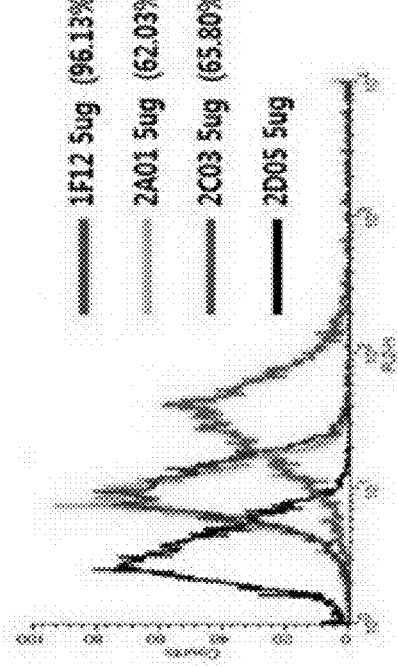
Figure 7D:
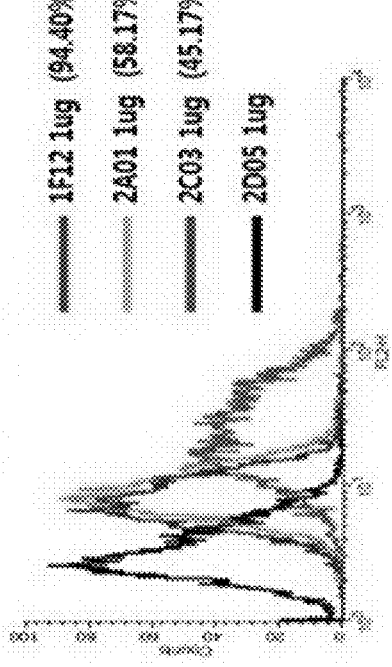
Figure 7I:
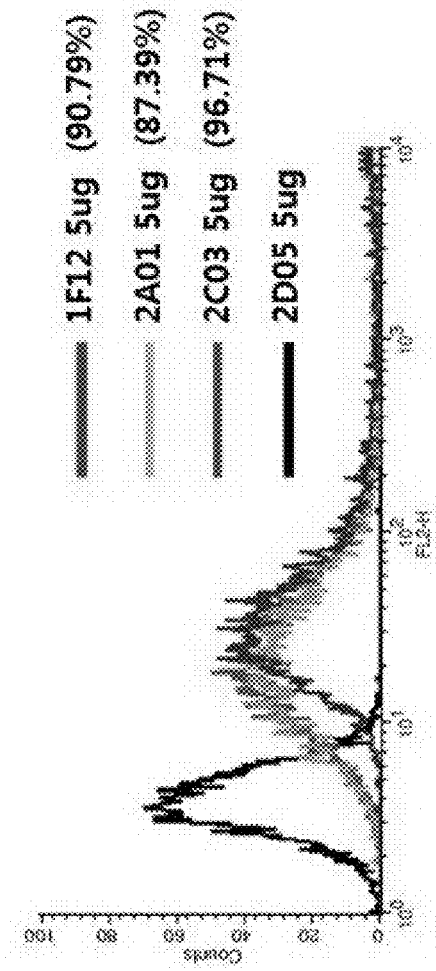
Figure 7J:
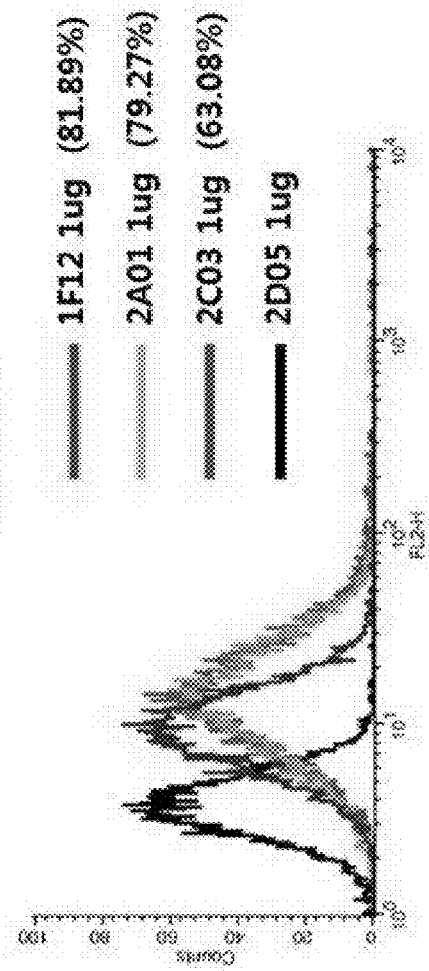

Verification on Inhibition of Antibody Fragments on Binding Between Ligand (Hepatocyte Growth Factor) and c-Met Through Competitive Binding For the verification of whether the selected scFv proteins have competitive binding affinity with the hepatocyte growth factor, which is the ligand of c-Met, the ligand competitive ELISA experiment was conducted. As in examples 2 and 4, the coated human c-Met was prepared, and respective wells were treated with samples in which each scFv protein was diluted at a 2-fold dilution from 500 ng/ml to about 1 ng/ml. After the treatment, the experiment procedure was conducted as in Example 4. Meanwhile, for the verification of the competitive binding affinity with the ligand, an experiment with regard to excessive treatment 2.5 μg/ml of HGF was conducted in the same manner. As a result, the 1F12 scFv and 2C03 scFv treatments showed somewhat dull competition despite a large amount of ligand, and the 2A01 scFv treatment showed sensitive competition in a concentration-dependent manner (FIGS. 6A-6C). These results verified that the 2A01 clone might bind closer to the ligand binding site of c-Met than 1F12 or 2C03 clone, thereby more effectively blocking the interaction between c-Met and the ligand. However, 1F12 and 2C03 scFv antibodies were also used for a functional evaluation using cell lines since there have been reports that antibodies having an excellent binding affinity to a receptor (or ligand) can exhibit effective treatment efficacies even though they poorly compete with the ligand to bind to the receptor.

Example 6

Verification on Binding Affinities of scFv Antibody Fragments to c-Met Overexpressing Cancer Lines It has been so far reported that there are c-Met overexpressing cell line models in various cancers. In consideration of this, the binding degrees of scFv antibodies were compared through FACS analysis using a total of five cancer cell lines. The five cancer cell lines were respectively derived from gastric cancer (MKN45), brain tumor (U87MG), kidney cancer (Caki-1), lung cancer (H441), and liver cancer (HepG2). Each of the cell lines was cultured in media (DMEM, 10% FBS), and $5 \times 10^5$ cells were prepared in each tube. After that, the cells were fixed by 4% Paraformaldehyde, followed by centrifugation, and the tube was washed one time with FACS analysis solution. The prepared cells were treated with 1 μg and 5 μg of each scFv protein, and then the corresponding antibody fragment was allowed to bind to the cells through culturing at 4° C. overnight. After that, non-specifically bound scFv proteins were washed two times with FACS solution, and then fluorescence (phycoerythrin, PE)-bound anti-HA antibody was allowed to bind to the cells for 1 hour. In addition, the cells were again washed with FACS solution, and 500 μl of FACS solution was added to perform a FACS analysis. Resultantly, all of three scFv antibody fragments, 1F12, 2A01, and 2C03, showed specific binding affinities to c-Met overexpressing cell lines as compared with the control group (2D05) (FIGS. 7A-7J). Further, since the binding tendency was verified to decrease with the decrease of scFv concentration, it can be seen that the corresponding scFv antibody fragments have high specificity to the target protein c-Met.

Figure 8A:
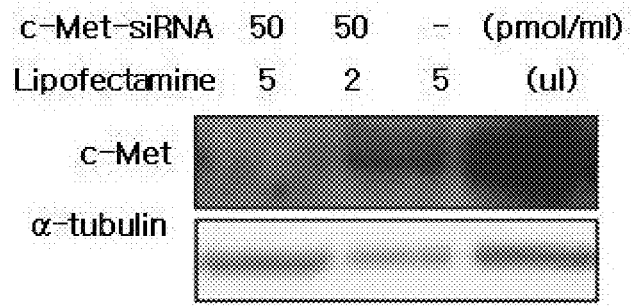
FIG. 8A through 8I show results confirming reductions in binding affinity of scFv antibody fragments due to c-Met expression inhibition in two c-Met overexpressing cell lines.
Figure 8B:
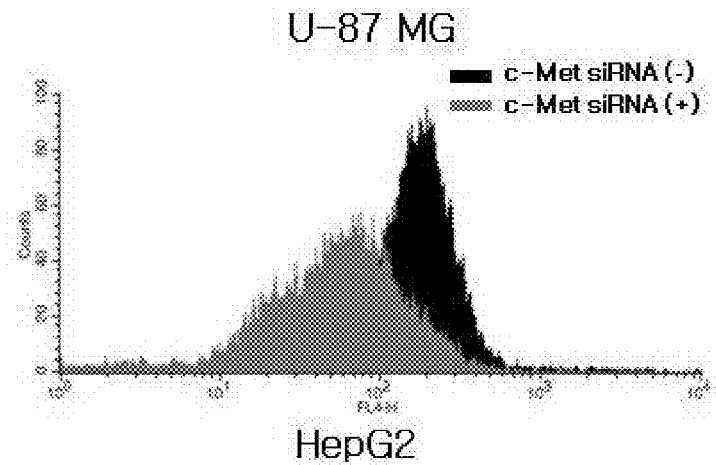
Figure 8C:
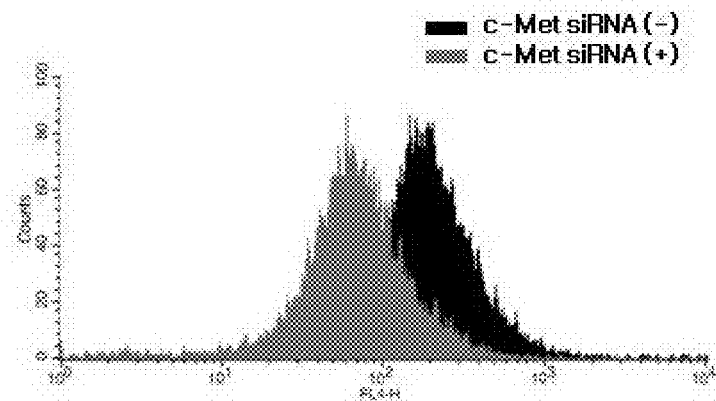
Figure 8D:
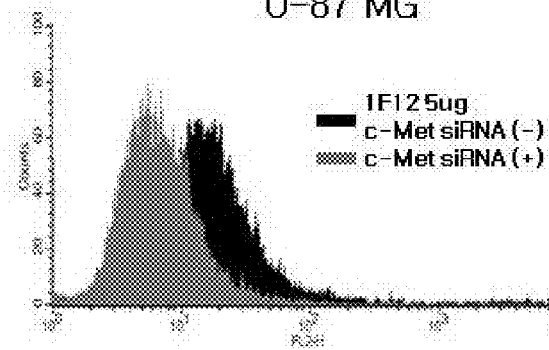
Figure 8G:
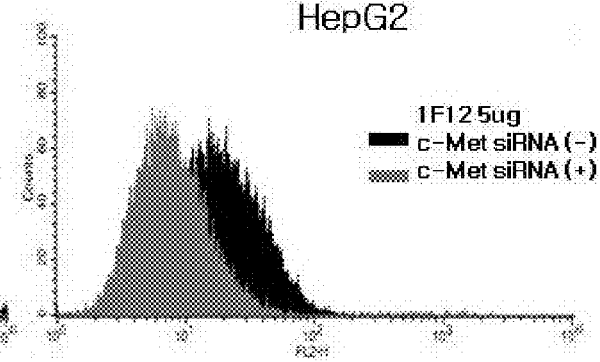
Figure 8E:
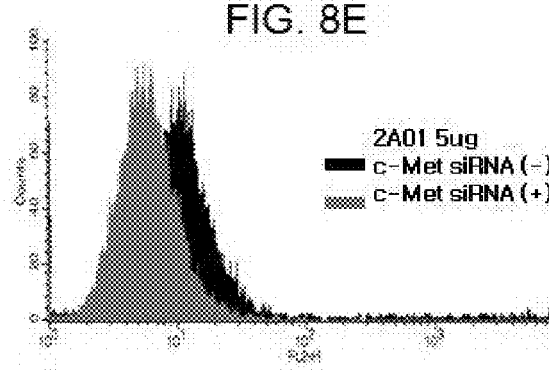
Figure 8H:
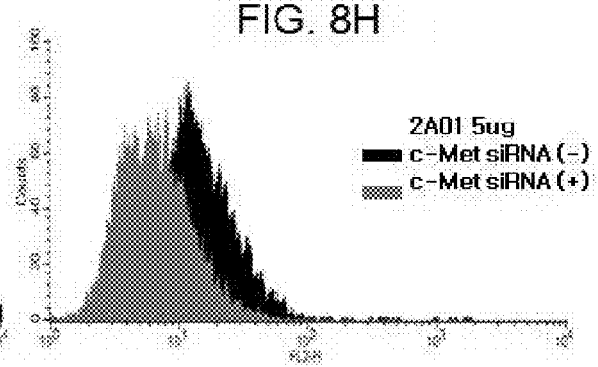
Figure 8F:
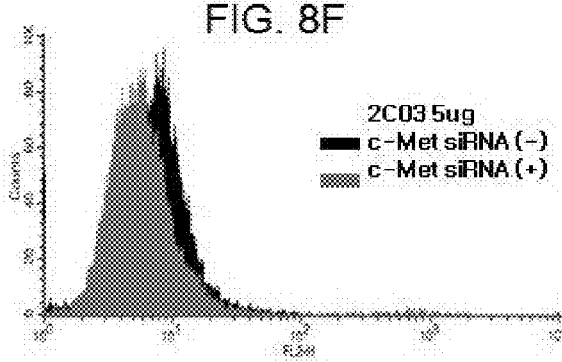
Figure 8I:
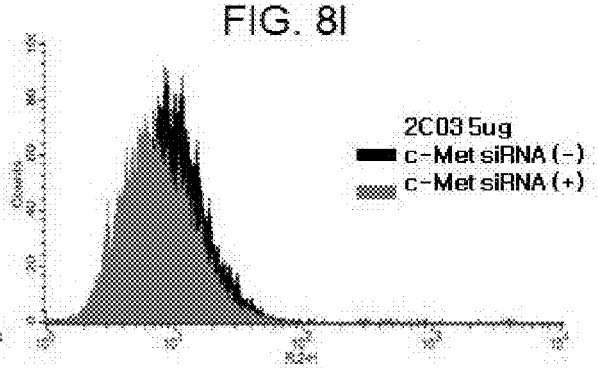
Figure 9A:
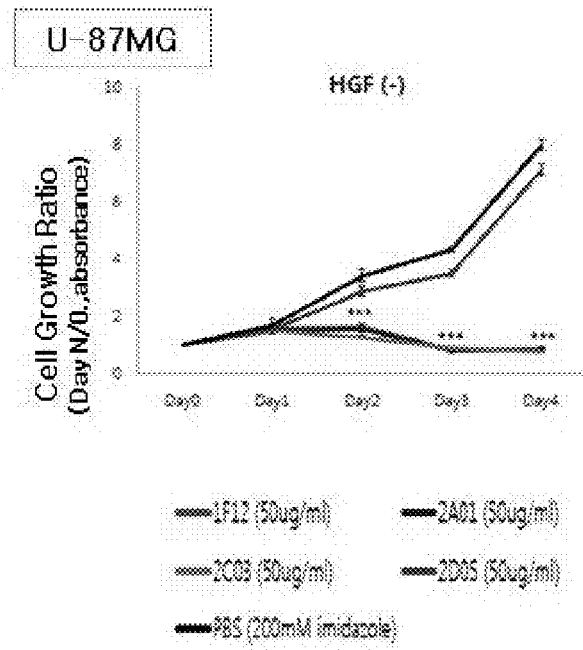
Figure 9B:
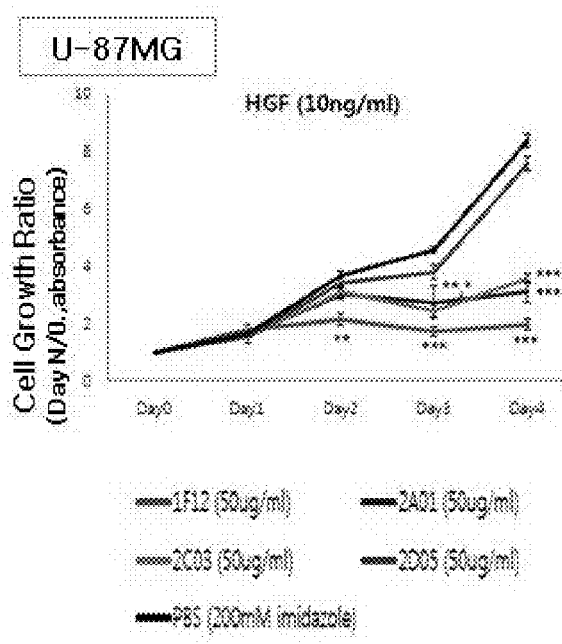
Figure 9C:
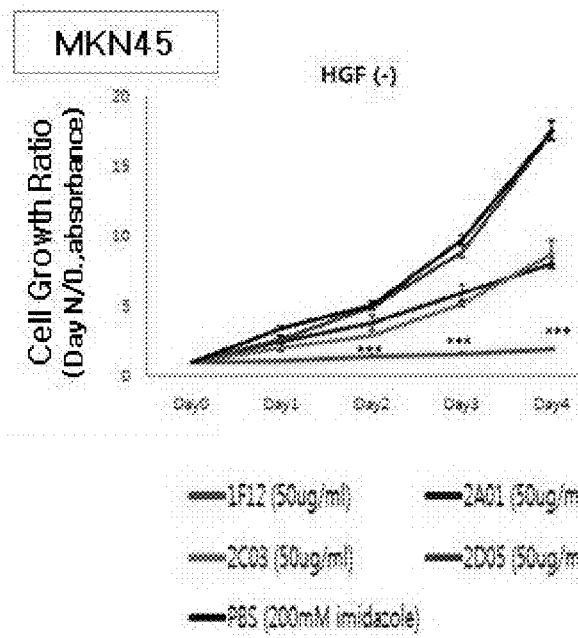
Figure 9D:
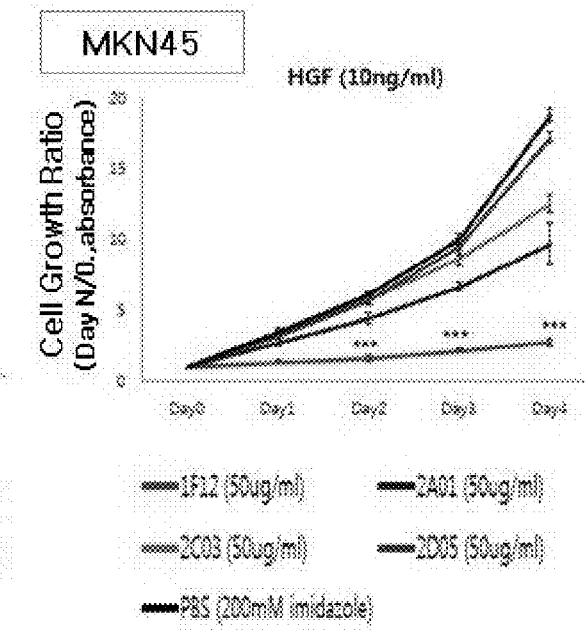

In addition, for the verification of specificities of scFv antibody fragments to c-Met using two representative cell lines (U87MG and HepG2) of the corresponding cell lines, c-Met knockdown was induced using c-Met-siRNA. The c-Met knockdown was conducted by mixing two variants SIHK1284 and SIHK1285 Met siRNA (sigma-aldrich) at the same concentration. As for cell introduction conditions, the cells were treated with 50 pmol/ml of siRNA together with Lipofectamine (Invitrogen) of 5 μl or 2 μl per reaction, and the proteins were collected from the cells. The optimum expression reduction conditions were confirmed through western blotting (FIG. 8A). After the introduction of siRNA, FACS analysis was conducted using c-Met monoclonal antibody. As shown in FIGS. 8B and 8C, the c-Met expression was verified to be reduced in both of U87MG and HepG2 cells. In addition, as expected, it was verified that the binding affinities of the respective scFv antibody fragments of 5 μg/ml to c-Met expression-reduced cells significantly decreased (FIGS. 8C-8I). This verified that the identified scFv antibody fragments had actually specificity to the c-Met extracellular domain present on cell membranes.

Example 7

Verification on Ability of scFv Antibody Fragments to Inhibit Cell Growth in c-Met Overexpressing Cancer Line For the verification of anti-cancer ability of the identified 1F12, 2A01, and 2C03 scFv antibody fragments through inhibition of cancer cell proliferation, cell proliferation assay was conducted. The experiment was conducted by using three cell lines, that is, UG87MG and KP-4 cell lines which act on c-Met overexpressed on cell surfaces by autocrine HGF, and MKN45 cells of which the autocrine function is not clear but in which the c-Met overexpressed on cell surfaces was hyperactivated to continuously induce c-Met signaling into the cells. Three cell lines were prepared such that $1 \times 10^3$ cells were present in 100 μl of media in conditions with (10 ng/ml) or without HGF. 50 μg/ml of individual scFv antibody fragment clones were prepared to treat wells containing three species of cells cultured for 24 hours. On day 0, 1, 2, 3, and 4, the degree of cell growth was measured by the EZ-Cytox cell viability assay kit (Daeil Lab. Service).

Resultantly, in the experiment without HGF, the growth inhibitory effects by all the clones were shown from day 2 in all of three cell lines (FIGS. 9A-9G). Meanwhile, in conditions with HGF, the growth inhibitory effect by the 1F12 scFv antibody fragment was the highest, and the 2A01 and 2C03 scFv antibody fragments also showed growth inhibitory effects, which were low but above the significant level. Based on these results, it was verified that the 1F12 scFv antibody fragment inhibited cell growth due to its distinctive high c-Met binding and the suppression of c-Met function therefrom.

Example 8

Verification on Permeability of Antibody Fragments into c-Met Overexpressing Cancer Cells For the intercellular localization of anti-c-Met antibody fragments, cell immunofluorescence staining assay was conducted. A 6-well plate was covered with sterilized slide coverslips. The experimental cell line MKN45 ($10^5$ cells/well) were seeded therein, and then the cells were cultured until the cells proliferated in 60-70% of the area. After that, the culture media were treated with 5 μg/ml of respective antibody fragments, and then allowed to stand 37° C. and 4° C. for 1 hour to induce interactions between the respective antibody fragments and c-Met. After that, the cells were fixed by Paraformaldehyde and treated with 0.1% Triton X-100 to improve cell permeability. After that, the cells were treated with 1% BSA blocking solution at room temperature for 1 hour, and then treated with a red fluorescent material (Alexa-Fluor 647)-labeled mouse anti-HA antibody (Cell Signaling Technology) for intercellular localization of respective candidate antibody fragments, followed by reaction at room temperature for 1 hour. Last, DAPI staining was conducted to stain the nuclei blue, followed by final washing. Then, the coverslips were taken out and fixed on the glass slide, which was then observed by confocal microscopy.

Figure 10:
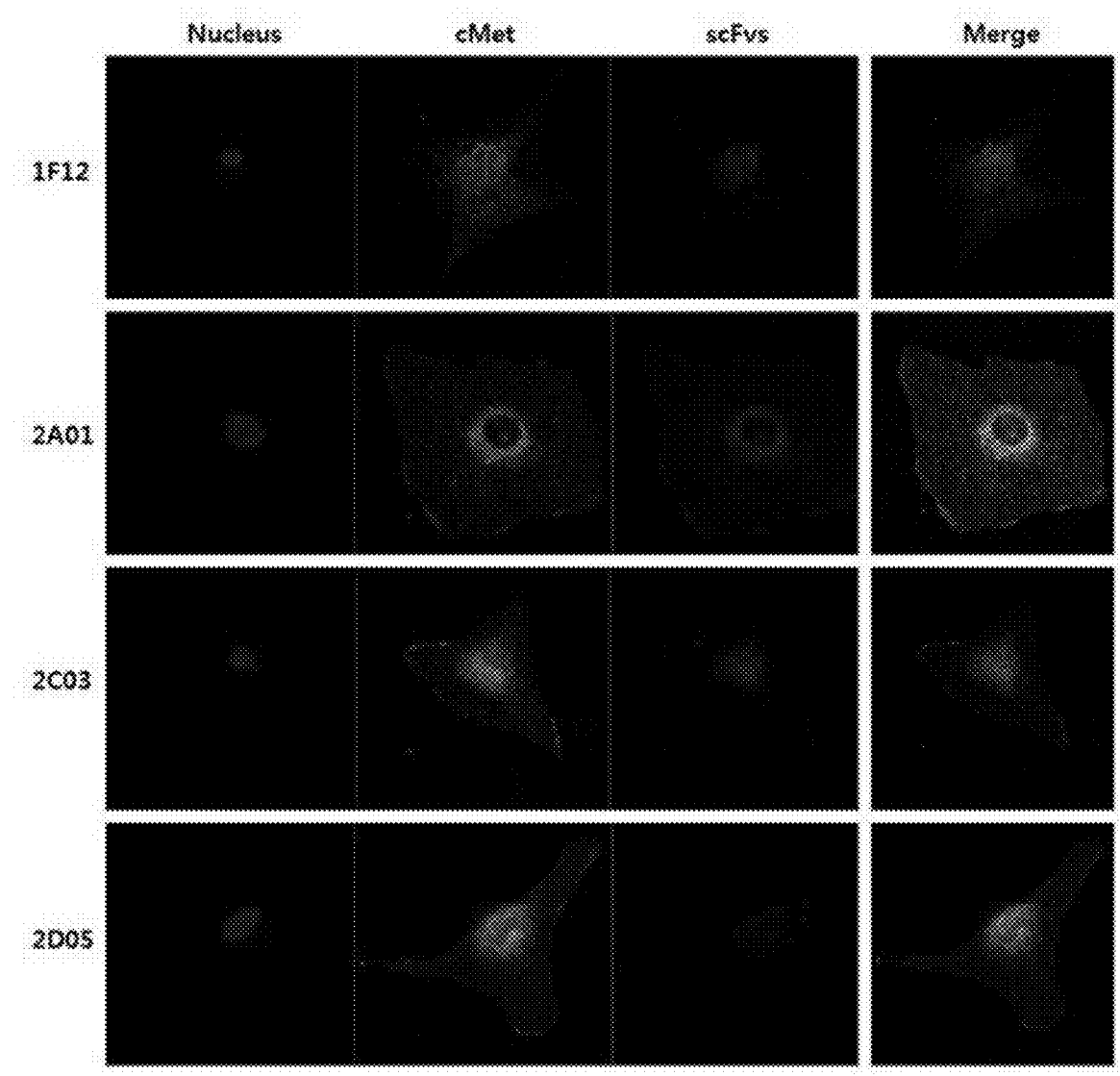
FIG. 10 shows immunofluorescence staining results confirming localization information of scFv antibody fragments treating the U87MG cancer line.
Figure 11A:
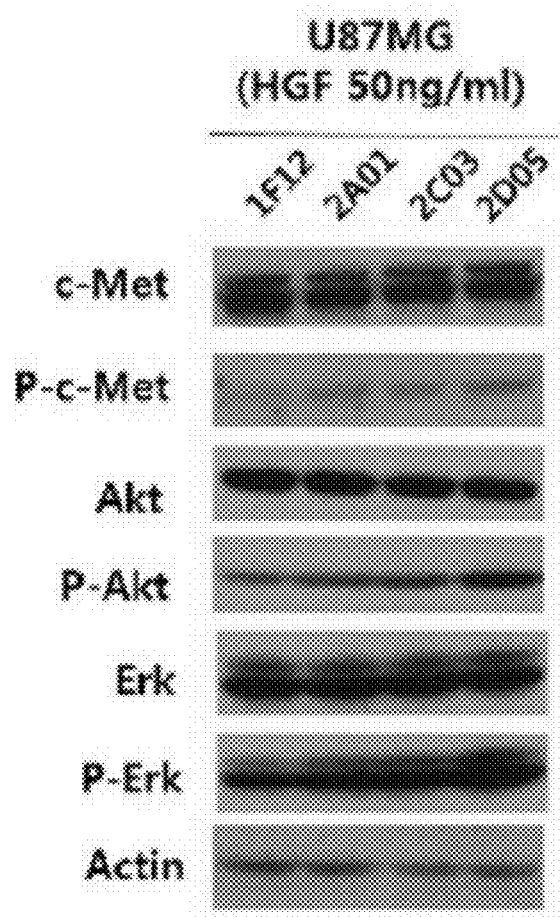
FIGS. 11A and 11B show western blotting results confirming the phosphorylation of downstream signaling molecules of a MET signaling pathway after U87MG and MKN54 cancer lines were treated with scFv antibody fragments.
Figure 11B:
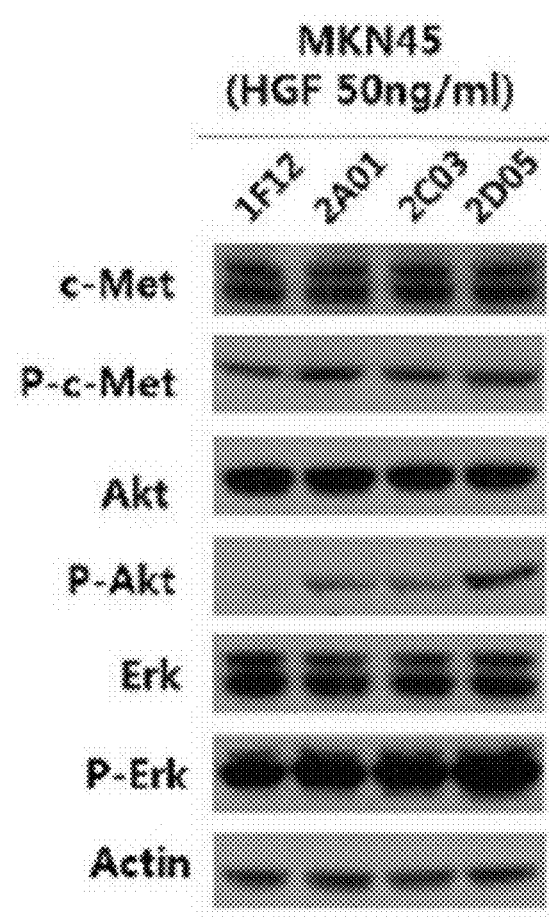

As the result of experiment, when the cells were treated with antibody fragments and allowed to stand at 4° C., the red fluorescence was not detected in the negative control group 2D05 antibody fragment. In the other three candidate antibody fragments, the red fluorescence was detected on only cell membranes. Antibody fragments were not detected in the cytoplasm (FIG. 10). Similarly, when the cells were treated with antibody fragments and then kept to stand at 37° C., red fluorescence was not detected in the negative control group 2D05 antibody fragment. However, in 37° C. conditions, unlike 4° C. conditions, the three candidate antibody fragments were verified to be located on cell membranes as well as in the cytoplasm. Considering the degree of red fluorescence, the 1F12 antibody fragment was showed to be more permeable into the cells than the other antibody fragments (FIG. 10).

Example 9

Verification on Inhibition of Antibody Fragments on Met Signaling Pathway

For the evaluation whether each scFv clone can inhibit the phosphorylation in downstream signaling molecules of the c-Met signaling pathways, western blotting was conducted. The experimental cell lines U87MG and MKN45 were cultured in a 6-well plate and treated with 50 ng/ml of HGF together with the respective antibody fragments. After that, the respective proteins were prepared using the RIPA buffer, and then SDS-PAGE electrophoresis was conducted on 10% gel. The proteins on the electrophoresis gel were transferred to the nitrocellulose membrane, and then proteins such as AKT and ERK associated with c-MET signaling pathway were detected by respective antibodies. As a result, it was verified that all of the three antibody fragments inhibited the phosphorylation of c-Met downstream signaling molecules, such as p-AKT and p-ERT, as compared with the negative control group 2D05 antibody fragment, and it was verified that 1F12 antibody fragment among the candidate antibodies can more effectively inhibit the phosphorylation of c-Met downstream signaling molecules.

Example 10

Verification on Neovascularization Inhibition

HGF/c-Met signaling pathway has been largely linked to VEGF, and induces proliferation and migration in endothelial cells to accelerate tumor angiogenesis (Rosen E M et al. Ciba Found Symp 212:215-226, 1997). Therefore, the human umbilical vein endothelial cell (HUVEC) model cell line was treated with respective clones with or without HGF, and then the tendency of neovascularization was observed. Matrigel (BD science) was slowly melted at a low temperature. Then, 50 μl of Matrigel was used to treat a 96-well plate, and then solidified at 37° C. The EBM-2 (basal medium) was treated with 20 ng/ml of HGF. Cells were dispensed into wells at 4,000/well, and then treated with 50 μg/ml of each antibody fragment. Neovascularization was induced in a $CO_2$ incubator at 37° C. for 6 hours, and then the formed blood vessels were photographed by optical microscopy.

Figure 12A:
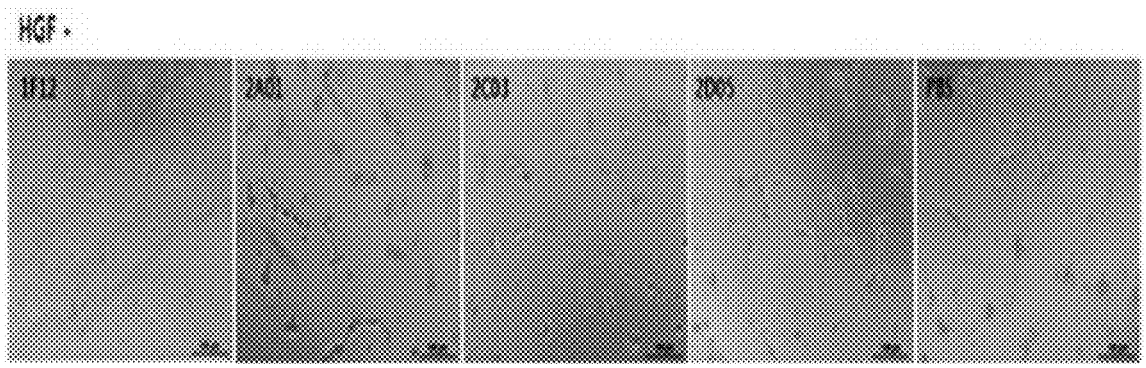
FIGS. 12A through 12D show results confirming the neovascularization inhibition observed when human umbilical vein endothelial cells (HUVECs) in conditions with hepatocyte growth factor (9HGF) were treated with respective scFv antibody fragments. Graphs below show measurement results of blood vessel length and number of branches stretching from the blood vessel.
Figure 12B:
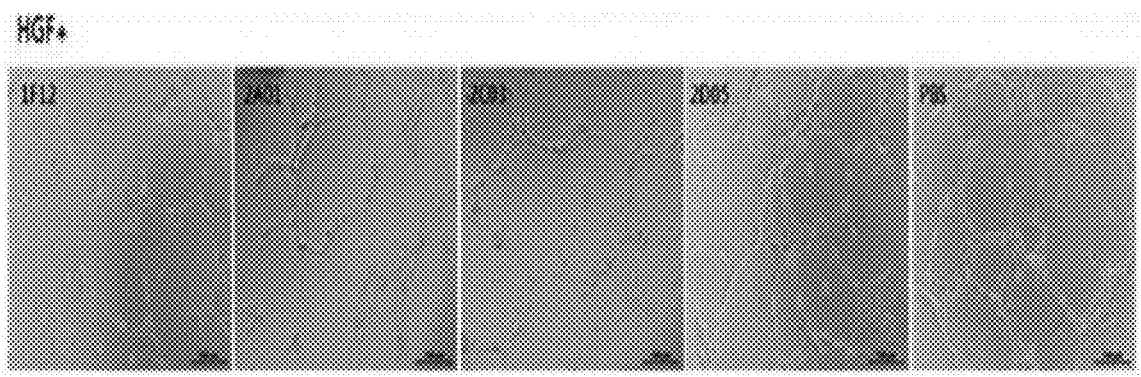
Figure 12C:
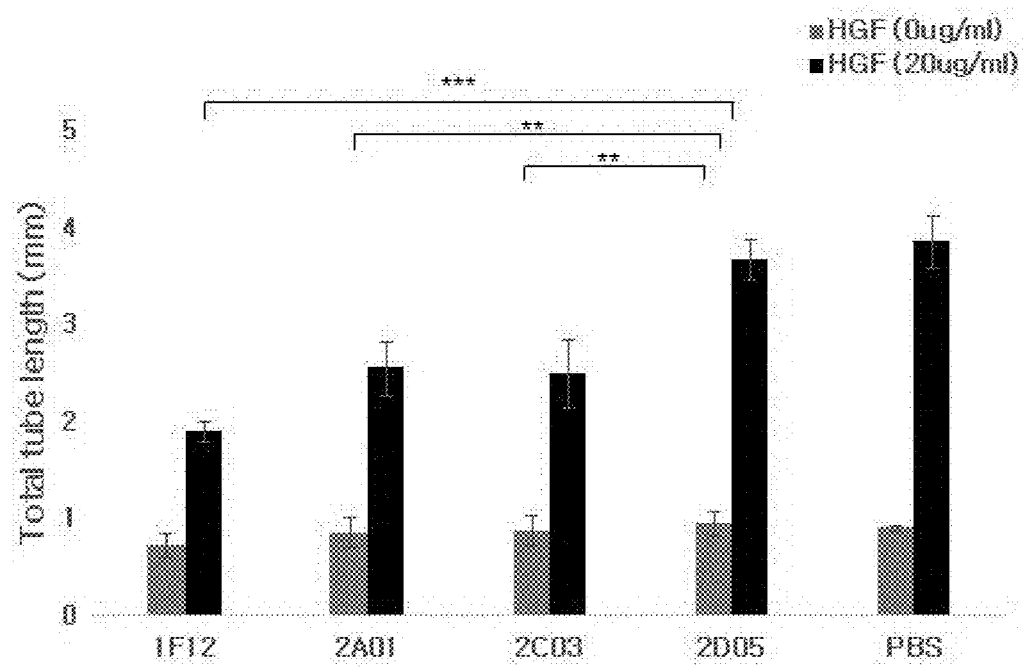
Figure 12D:
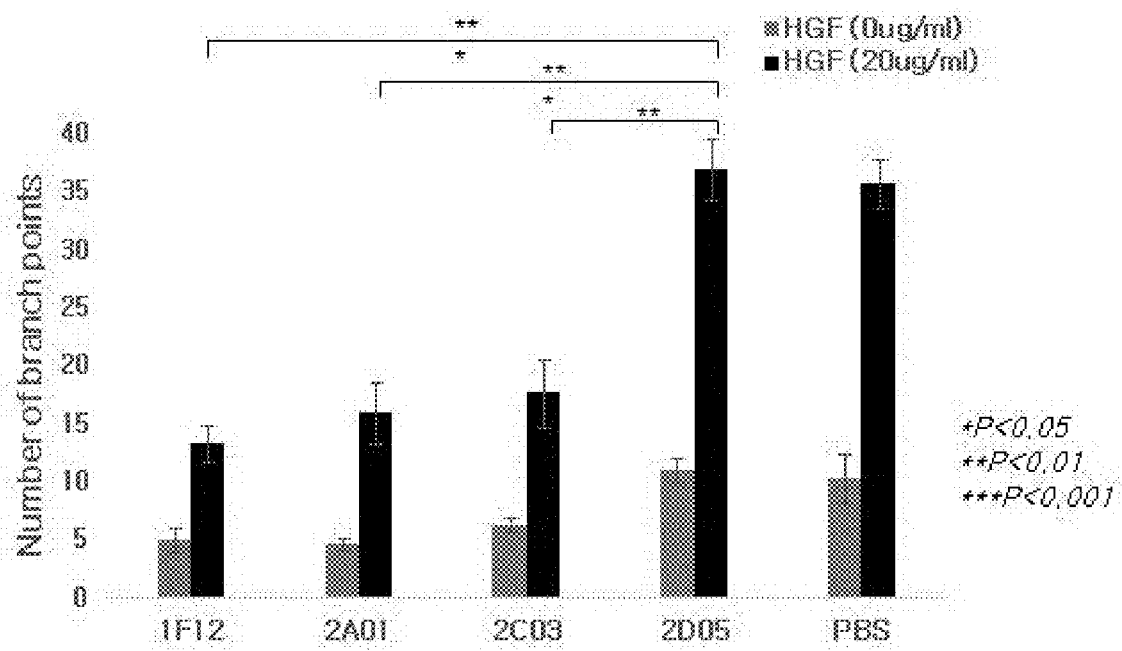

As the result of experiment, the neovascularization of HUVEC cell line was verified to be accelerated by HGF treatment in the negative control group (PBS, 2D05), and it was visually verified that this acceleration of neovascularization was effectively inhibited by treatment with the candidate antibodies having a binding affinity to c-Met (FIGS. 12A and 12B). In addition, this inhibitory effect was verified to be significant as compared with the negative control group by expressing the length or number of the formed blood vessels as numerical values (FIGS. 12C and 12D).

Example 11

Verification on Identification of Binding Sites of Respective Clones Through Epitope Mapping The epitope mapping of respective anti-c-Met antibody fragments was performed using peptide array technology. Based on the amino acid sequence expressing the extracellular domain of c-Met, a cellulose membrane on which 224 different 15-mer peptides were synthesized was prepared (JPT Peptide Technologies, FIGS. 13A to 13C). First, the prepared membrane was immersed in methanol for 1 minute to avoid the precipitation of hydrophobic peptides during the TBS washing procedure. The membrane was then washed three times with TBS for 10 minutes, and blocked at room temperature for 3 hours (5% skim milk). After that, the membrane was treated with respective antibody fragments diluted to a concentration of 1 μg/ml in the blocking buffer, and then allowed to stand at 4° C. overnight. The next day, the membrane was washed with TBST three times for 1 minute for each time, and an electric field of 1.0 $mA/cm^2$ was applied to the membrane for 1 hour to transfer the antibody fragments, which were non-covalently bound to the peptide membrane, and to the PVDF membrane. This procedure was repeated three times. The PVDF membrane from the third time was used since the PVDF membrane from the first time and second time emits non-specific spots. The PVDF membrane from the third time was washed with TBST three times for 10 minutes for each time. The PVDF membrane to which the bound antibody fragment was transferred was again blocked (5% skim milk) for 3 hours, and then treated with anti-HA-HRP antibody at room temperature for 2 hours to label the strongly bound antibody fragments. The membrane was washed three times with TBST for 5 minutes for each time. After that, the membrane was treated with a substrate (Amersham ECL Prime Detection Reagent, GE healthcare), and then subjected to film exposure and sensitization to identify epitope.

Figure 14A:
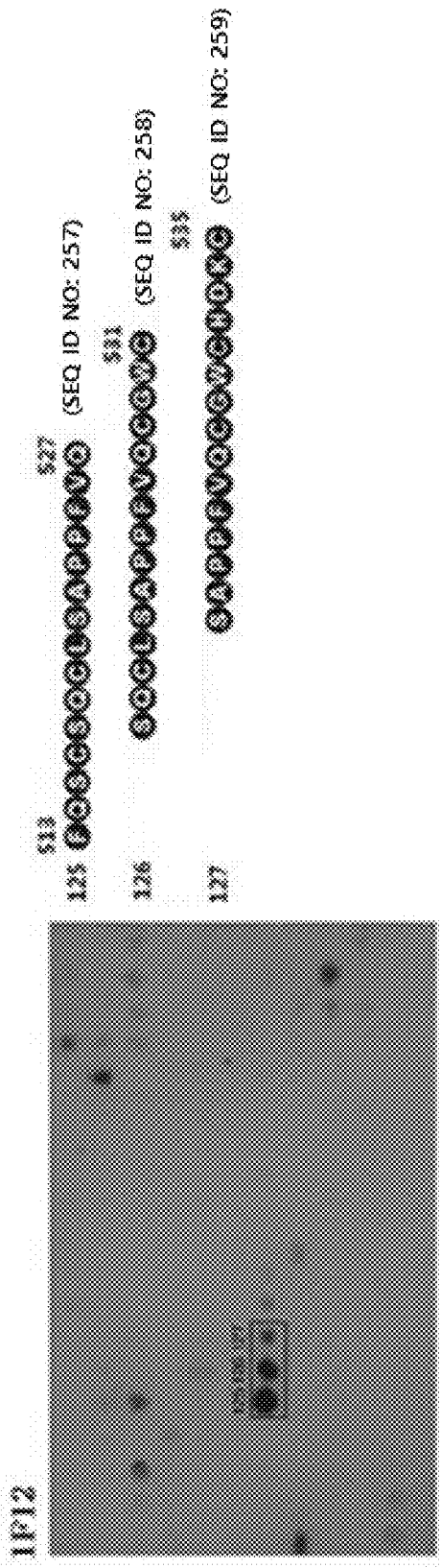
Figure 14B:
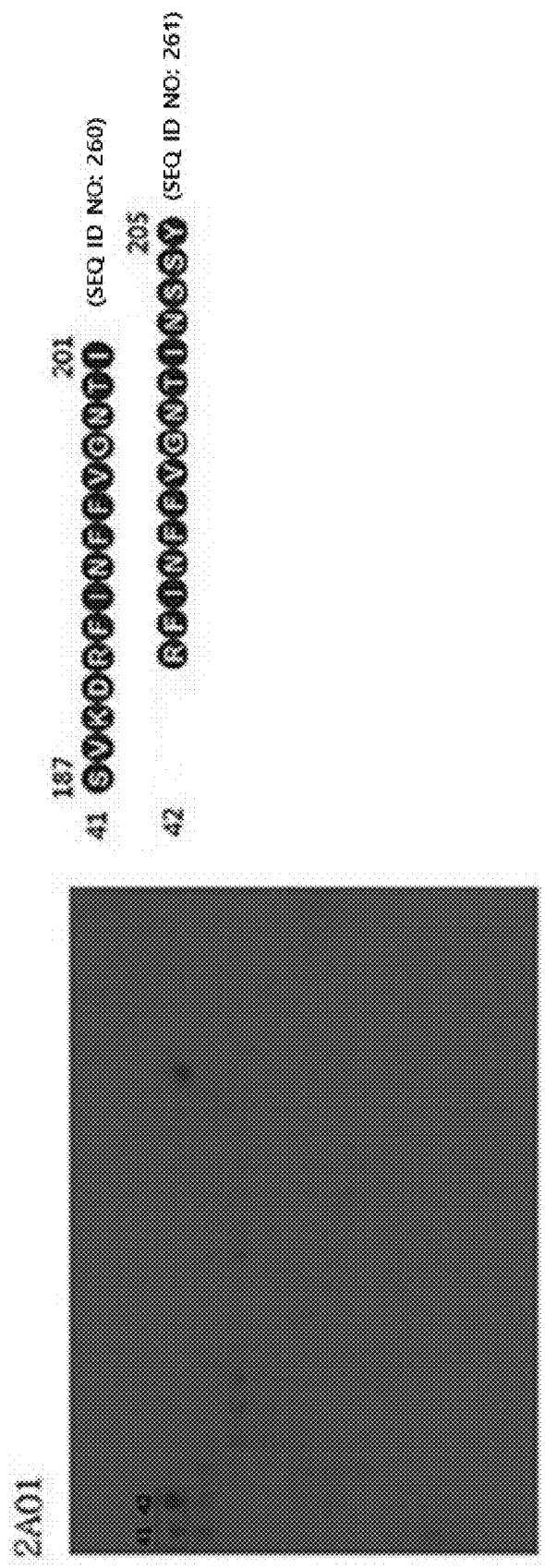

As the result of experiment, the 1F12 antibody fragment was verified to bind to the peptide fragment coding the PSI domain of c-Met, and the 2A01 and 2C03 antibody fragments were verified to bind to the peptide fragment coding the Sema domain of c-Met (FIGS. 14A to 14C). Through these results, it can be inferred that 2A01 and 2C03 would bind to the epitope (Sema domain) of antibodies, which was previously reported, thereby inducing the inhibition of cell growth through competition with HGF. Further, it was interestingly concluded that the 1F12 antibody fragment would bind to new epitope (PSI domain), which was not previously reported, thereby exhibiting higher effects in binding affinity, cell growth inhibition, intracellular signaling inhibition, and the like.

Example 12

Figure 15A:
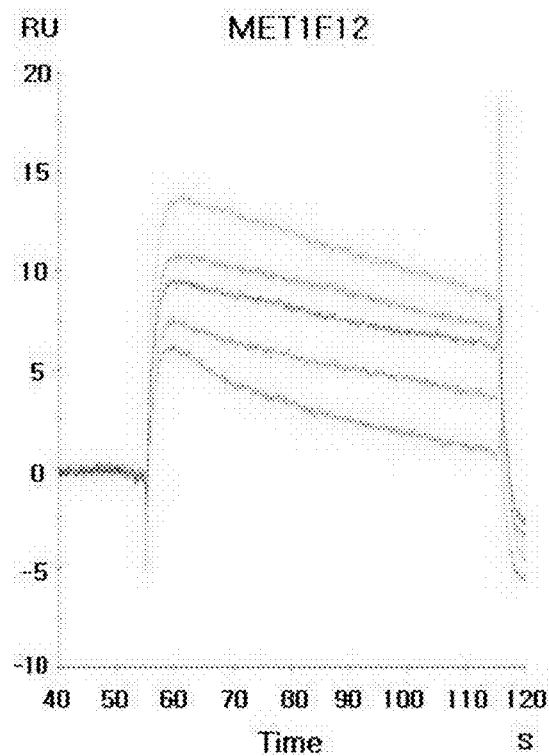
FIGS. 15A through 15C show shows sensorgram results of respective scFv clones according to concentrations with regard to c-Met through surface plasmon resonance.
Figure 15B:
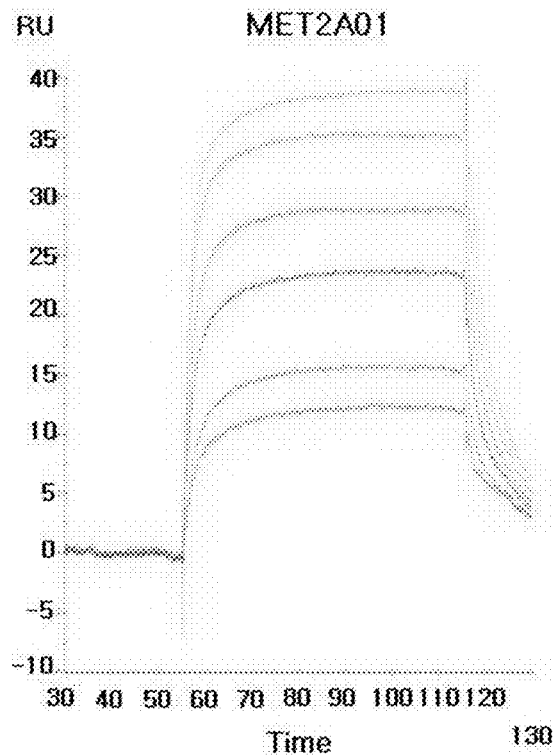
Figure 15C:
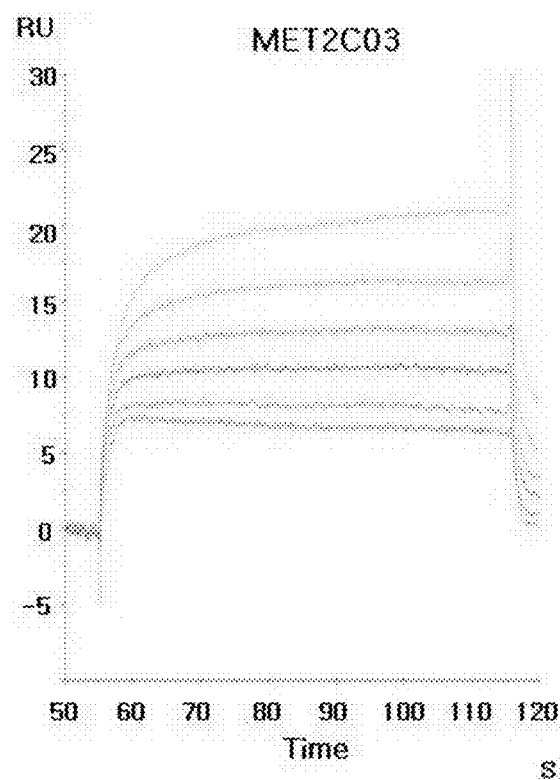

Determination of Coupling Constants of Respective Clones Using Surface Plasmon Resonance For the confirmation of more accurate binding affinity (coupling constant), the binding affinity of respective clones to c-Met was verified through surface plasmon resonance analysis. Respective antibody fragments were expressed in the host *E. coli*, followed by purification, and then dialyzed with PBS solution. Biacore T100 (GE healthcare) was used for the analysis. The c-Met protein was fixed to a dextran medium through an amine coupling reaction in the CM5 sensor chip. The respective antibody fragments were diluted with the HBS-EP solution, and the binding affinity values (resonance unit, RU) thereof were analyzed according to concentrations (FIGS. 15A to 15C). Based on these values, kinetic analysis was conducted through the BIA-evaluation program. As a result, the KD values of the 1F12 and 2A01 clones were measured to be $6^{-9} \times 10^{-8}$ M and the Kd value of 2C03 was verified to be $10^{-7}$ M (Table 4). Considering that the antibody type is a single chain antibody fragment, it can be seen that the corresponding binding affinities of the 1F12 and 2A01 clones have significantly high levels, and it was ascertained that these binding affinities of the respective clones also played critical roles in inhibiting functions of c-Met, such as inhibiting cell growth and signal transduction.

TABLE 4

| Coupling constant (Kd) based on Ka and Kb measured by surface plasmon resonance | | | |
|---|---|---|---|
| — | $K_D(M)$ | $K_a(M^{-1}S^{-1})$ | $K_d(S^{-1})$ |
| 1F12 | $9.33 \times 10^{-8}$ | $5.12 \times 10^4$ | $4.78 \times 10^{-4}$ |
| 2A01 | $6.60 \times 10^{-8}$ | $2.32 \times 10^6$ | $1.53 \times 10^{-1}$ |
| 2C03 | $2.39 \times 10^{-7}$ | $7.76 \times 10^5$ | $1.86 \times 10^{-1}$ |

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An antibody to human c-Met or its antigen-binding fragment, comprising:
   (a) a heavy chain variable region having the following heavy chain complementarity determining region (CDR) amino acid sequences: CDRH1 including the amino acid sequence of SEQ ID NO: 1, CDRH2 including the amino acid sequence of SEQ ID NO: 2, and CDRH3 including the amino acid sequence of SEQ ID NO: 3; and
   (b) a light chain variable region having the following light chain CDR amino acid sequences: CDRL1 including the amino acid sequence of SEQ ID NO: 4, CDRL2 including the amino acid sequence of SEQ ID NO: 5, and CDRL3 including the amino acid sequence of SEQ ID NO: 6.

2. The antibody to human c-Met or its antigen-binding fragment of claim 1, wherein the heavy chain variable region includes the amino acid sequence of SEQ ID NO: 19.

3. The antibody to human c-Met or its antigen-binding fragment of claim 1, wherein the light chain variable region includes the amino acid sequence of SEQ ID NO: 20.

4. A composition comprising: (a) the antibody to human c-Met or its antigen-binding fragment of claim 1; and (b) a pharmaceutically acceptable carrier.

* * * * *

SEQUENCE LISTING

```
<160> NUMBER OF SEQ ID NOS: 306

<210> SEQ ID NO 1
<211> LENGTH: 8
<212> TYPE: PRT
<213> ORGANISM: Artificial Sequence
<220> FEATURE:
<223> OTHER INFORMATION: 1F12 heavy chain CDR1

<400> SEQUENCE: 1

Gly Phe Thr Phe Ser Asn Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: 1F12 heavy chain CDR2

<400> SEQUENCE: 2

Ile Ser Tyr Ser Gly Gly Ser Thr
1               5

<210> SEQ ID NO 3
<211> LENGTH: 20
<212> TYPE: PRT
<213> ORGANISM: Artificial Sequence
<220> FEATURE:
<223> OTHER INFORMATION: 1F12 heavy chain CDR3

<400> SEQUENCE: 3

Ala Lys Ala Ser Arg Ser Cys Gln Arg Pro Ala Cys Ser Tyr Ala Asn
1               5                   10                  15

Gly Met Asp Val
            20

<210> SEQ ID NO 4
<211> LENGTH: 8
<212> TYPE: PRT
<213> ORGANISM: Artificial Sequence
<220> FEATURE:
<223> OTHER INFORMATION: 1F12 light chain CDR1

<400> SEQUENCE: 4

Ser Ser Asn Ile Gly Asn Asn Tyr
1               5
```

```
<210> SEQ ID NO 5
<211> LENGTH: 3
<212> TYPE: PRT
<213> ORGANISM: Artificial Sequence
<220> FEATURE:
<223> OTHER INFORMATION: 1F12 light chain CDR2

<400> SEQUENCE: 5

Tyr Asn Asn
1

<210> SEQ ID NO 6
<211> LENGTH: 11
<212> TYPE: PRT
<213> ORGANISM: Artificial Sequence
<220> FEATURE:
<223> OTHER INFORMATION: 1F12 light chain CDR3

<400> SEQUENCE: 6

Gly Ser Trp Asp Tyr Ser Leu Ser Ala Tyr Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: 2A01 heavy chain CDR1

<400> SEQUENCE: 7

Gly Phe Thr Phe Ser Ser Tyr Asp
1               5

<210> SEQ ID NO 8
<211> LENGTH: 8
<212> TYPE: PRT
<213> ORGANISM: Artificial Sequence
<220> FEATURE:
<223> OTHER INFORMATION: 2A01 heavy chain CDR2

<400> SEQUENCE: 8

Ile Ser His Gly Gly Ser Ser Ile
1               5

<210> SEQ ID NO 9
<211> LENGTH: 14
<212> TYPE: PRT
<213> ORGANISM: Artificial Sequence
<220> FEATURE:
<223> OTHER INFORMATION: 2A01 heavy chain CDR3

<400> SEQUENCE: 9

Ala Lys Asp Ala Tyr Pro Ile Arg Gln Glu Thr Phe Asp Tyr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: 2A01 light chain CDR1

<400> SEQUENCE: 10

Ser Ser Asn Ile Gly Asn Asn Asp
1               5
```

```
<210> SEQ ID NO 11
<211> LENGTH: 3
<212> TYPE: PRT
<213> ORGANISM: Artificial Sequence
<220> FEATURE:
<223> OTHER INFORMATION: 2A01 light chain CDR2

<400> SEQUENCE: 11

Pro Asp Ser
1

<210> SEQ ID NO 12
<211> LENGTH: 11
<212> TYPE: PRT
<213> ORGANISM: Artificial Sequence
<220> FEATURE:
<223> OTHER INFORMATION: 2A01 light chain CDR3

<400> SEQUENCE: 12

Ala Ser Trp Asp Ser Ser Leu Ser Gly Tyr Val
1               5                   10

<210> SEQ ID NO 13
<211> LENGTH: 8
<212> TYPE: PRT
<213> ORGANISM: Artificial Sequence
<220> FEATURE:
<223> OTHER INFORMATION: 2C03 heavy chain CDR1

<400> SEQUENCE: 13

Gly Phe Thr Phe Ser Asn Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: 2C03 heavy chain CDR2

<400> SEQUENCE: 14

Ile Ser Tyr Asp Ser Gly Ser Ile
1               5

<210> SEQ ID NO 15
<211> LENGTH: 20
<212> TYPE: PRT
<213> ORGANISM: Artificial Sequence
<220> FEATURE:
<223> OTHER INFORMATION: 2C03 heavy chain CDR3

<400> SEQUENCE: 15

Ala Lys Ala Ala Arg Ser Cys Arg Asn Trp Ser Cys Ser Tyr Ala Asn
1               5                   10                  15

Gly Met Asp Val
            20

<210> SEQ ID NO 16
<211> LENGTH: 8
<212> TYPE: PRT
<213> ORGANISM: Artificial Sequence
<220> FEATURE:
<223> OTHER INFORMATION: 2C03 light chain CDR1

<400> SEQUENCE: 16

Ser Ser Asn Ile Gly Ser Asn Tyr
1               5
```

```
<210> SEQ ID NO 17
<211> LENGTH: 3
<212> TYPE: PRT
<213> ORGANISM: Artificial Sequence
<220> FEATURE:
<223> OTHER INFORMATION: 2CO3 light chain CDR2

<400> SEQUENCE: 17

Ser Asp Ser
1

<210> SEQ ID NO 18
<211> LENGTH: 11
<212> TYPE: PRT
<213> ORGANISM: Artificial Sequence
<220> FEATURE:
<223> OTHER INFORMATION: 2CO3 light chain CDR3

<400> SEQUENCE: 18

Gly Ser Trp Asp Asp Ser Leu Ser Gly Tyr Val
1               5                   10

<210> SEQ ID NO 19
<211> LENGTH: 127
<212> TYPE: PRT
<213> ORGANISM: Artificial Sequence
<220> FEATURE:
<223> OTHER INFORMATION: Heavy chain variable region of synthetic 1F12
      scFv A/a sequence

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ser Arg Ser Cys Gln Arg Pro Ala Cys Ser Tyr Ala Asn
            100                 105                 110

Gly Met Asp Val Trp Gly Gln Gly Thr Leu Val Thr Val Ser Ser
        115                 120                 125

<210> SEQ ID NO 20
<211> LENGTH: 110
<212> TYPE: PRT
<213> ORGANISM: Artificial Sequence
<220> FEATURE:
<223> OTHER INFORMATION: Light chain variable region of synthetic 1F12
      scFv A/a sequence

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30
```

```
Tyr Val Thr Trp Tyr Gln Gln Leu Pro Gly Thr Ala Pro Lys Leu Leu
            35                  40                  45

Ile Tyr Tyr Asn Asn His Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Gly Ser Trp Asp Tyr Ser Leu
                 85                  90                  95

Ser Ala Tyr Val Phe Gly Gly Gly Thr Lys Leu Thr Val Leu
                100                 105                 110

<210> SEQ ID NO 21
<211> LENGTH: 121
<212> TYPE: PRT
<213> ORGANISM: Artificial Sequence
<220> FEATURE:
<223> OTHER INFORMATION: Heavy chain variable region of synthetic 2A01
      scFv A/a sequence

<400> SEQUENCE: 21

Glu Val Gln Leu Leu Glu Ser Gly Gly Gly Leu Val Gln Thr Gly Gly
 1               5                  10                  15

Ser Leu Arg Leu Ser Cys Ala Ala Ser Gly Phe Thr Phe Ser Ser Tyr
                20                  25                  30

Asp Met Ser Trp Val Arg Arg Ala Pro Gly Lys Gly Leu Glu Trp Val
            35                  40                  45

Ser Trp Ile Ser His Gly Gly Ser Ser Ile Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Tyr Pro Ile Arg Gln Glu Thr Phe Asp Tyr Trp Gly
                100                 105                 110

Gln Gly Thr Leu Val Thr Val Ser Ser
        115                 120

<210> SEQ ID NO 22
<211> LENGTH: 110
<212> TYPE: PRT
<213> ORGANISM: Artificial Sequence
<220> FEATURE:
<223> OTHER INFORMATION: Light chain variable region of synthetic 2A01
      scFv A/a sequence

<400> SEQUENCE: 22

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
                20                  25                  30

Asp Val Ser Trp Tyr Gln Gln Leu Pro Gly Thr Ala Pro Lys Leu Leu
            35                  40                  45

Ile Tyr Pro Asp Ser Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ser Trp Asp Ser Ser Leu
                 85                  90                  95
```

```
Ser Gly Tyr Val Phe Gly Gly Gly Thr Lys Leu Thr Val Leu
            100                 105                 110
```

<210> SEQ ID NO 23
<211> LENGTH: 127
<212> TYPE: PRT
<213> ORGANISM: Artificial Sequence
<220> FEATURE:
<223> OTHER INFORMATION: Heavy chain variable region of synthetic 2C03
      scFv A/a sequence

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Tyr Asp Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Arg Ser Cys Arg Asn Trp Ser Cys Ser Tyr Ala Asn
            100                 105                 110

Gly Met Asp Val Trp Gly Gln Gly Thr Leu Val Thr Val Ser Ser
        115                 120                 125
```

<210> SEQ ID NO 24
<211> LENGTH: 110
<212> TYPE: PRT
<213> ORGANISM: Artificial Sequence
<220> FEATURE:
<223> OTHER INFORMATION: Light chain variable region of synthetic 2C03
      scFv A/a sequence

<400> SEQUENCE: 24

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Ser Trp Tyr Arg Gln Leu Pro Gly Thr Ala Pro Lys Leu Leu
        35                  40                  45

Ile Tyr Ser Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ser Ser Leu
                85                  90                  95

Ser Gly Tyr Val Phe Gly Gly Gly Thr Lys Leu Thr Val Leu
            100                 105                 110
```

<210> SEQ ID NO 25
<211> LENGTH: 15
<212> TYPE: PRT
<213> ORGANISM: Artificial Sequence
<220> FEATURE:
<223> OTHER INFORMATION: Linker sequence(G4S)3 in all of the scFv clones
      A/a sequence

<400> SEQUENCE: 25

Gly Gly Gly Gly Ser Gly Gly Gly Gly Ser Gly Gly Gly Gly Ser
1               5                   10                  15

<210> SEQ ID NO 26
<211> LENGTH: 381
<212> TYPE: DNA
<213> ORGANISM: Artificial Sequence
<220> FEATURE:
<223> OTHER INFORMATION: Heavy chain variable region of synthetic 1F12
      scFv

<400> SEQUENCE: 26
gaggtgcagc tgttggagtc tgggggaggc ttggtacagc ctggggggtc cctgagactc     60
tcctgtgcag cctctggatt cacctttagc aattatgcta tgagctgggt ccgccaggct    120
ccagggaagg ggctggagtg ggtctcaggg atctcttata gtggtggtag tacatattac    180
gctgattctg taaaaggtcg gttcaccatc tccagagaca attccaagaa cacgctgtat    240
ctgcaaatga acagcctgag agccgaggac acggccgtgt attactgtgc gaaagctagt    300
cgttcttgtc agcggcctgc ttgttcttat gctaatggta tggacgtctg gggccagggt    360
acactggtca ccgtgagctc a                                              381

<210> SEQ ID NO 27
<211> LENGTH: 330
<212> TYPE: DNA
<213> ORGANISM: Artificial Sequence
<220> FEATURE:
<223> OTHER INFORMATION: Light chain variable region of synthetic 1F12
      scFv

<400> SEQUENCE: 27
cagtctgtgc tgactcagcc accctcagcg tctgggaccc ccgggcagag ggtcaccatc     60
tcttgtactg gctcttcatc taatattggc aataattatg tcacctggta ccagcagctc    120
ccaggaacgg cccccaaact cctcatctat tataataatc atcggccaag cggggtccct    180
gaccgattct ctggctccaa gtctggcacc tcagcctccc tggccatcag tgggctccag    240
tccgaggatg aggctgatta ttactgtggt tcttgggatt atagcctgag tgcttatgtc    300
ttcggcggag gcaccaagct gacggtccta                                     330

<210> SEQ ID NO 28
<211> LENGTH: 363
<212> TYPE: DNA
<213> ORGANISM: Artificial Sequence
<220> FEATURE:
<223> OTHER INFORMATION: Heavy chain variable region of synthetic 2A01
      scFv

<400> SEQUENCE: 28
gaggtgcagc tgttggagtc tgggggaggc ttggtacaga ctggggggtc cctgagactc     60
tcctgtgcag cctctggatt cacctttagc agttatgata tgagctgggt ccgccgggct    120
ccagggaagg ggctggagtg ggtctcatgg atctctcatg gtggtagtag tatatcttac    180
gctgattctg taaaaggtcg gttcaccatc tccagagaca attccaagaa cacgctgtat    240
ctgcaaatga acagcctgag agccgaggac acggccgtgt attactgtgc gaaagatgct    300
tatcctattc ggcaggagac tttcgactac tggggccagg gtacactggt caccgtgagc    360
tca                                                                  363

<210> SEQ ID NO 29
<211> LENGTH: 330
<212> TYPE: DNA
<213> ORGANISM: Artificial Sequence
<220> FEATURE:
<223> OTHER INFORMATION: Light chain variable region of synthetic 2A01 scFv

<400> SEQUENCE: 29

| | | | | | |
|---|---|---|---|---|---|
| cagtctgtgc | tgactcagcc | accctcagcg | tctgggaccc | ccgggcagag | ggtcaccatc | 60 |
| tcttgtagtg | gctcttcatc | taatattggc | aataatgatg | tctcctggta | ccagcagctc | 120 |
| ccaggaacgg | cccccaaact | cctcatctat | cctgatagtc | agcggccaag | cggggtccct | 180 |
| gaccgattct | ctggctccaa | gtctggcacc | tcagcctccc | tggccatcag | tgggctccgg | 240 |
| tccgaggatg | aggctgatta | ttactgtgct | tcttgggatt | ctagcctgag | tggctatgtc | 300 |
| ttcggcggag | gcaccaagct | gacggtccta | | | | 330 |

<210> SEQ ID NO 30
<211> LENGTH: 381
<212> TYPE: DNA
<213> ORGANISM: Artificial Sequence
<220> FEATURE:
<223> OTHER INFORMATION: Heavy chain variable region of synthetic 2C03 scFv

<400> SEQUENCE: 30

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | aattatgcta | tgagctgggt | ccgccaggct | 120 |
| ccagggaagg | ggctggagtg | ggtctcagcg | atctcttatg | atagtggtag | tatatattac | 180 |
| gctgattctg | taaaaggtcg | gttcaccatc | tccagagaca | attccaagaa | cacgctgtat | 240 |
| ctgcaaatga | acagcctgag | agccgaggac | acggccgtgt | attactgtgc | gaaagctgct | 300 |
| cgtagttgtc | ggaattggtc | gtgttcttat | gctaatggta | tggacgtctg | gggccagggt | 360 |
| acactggtca | ccgtgagctc | a | | | | 381 |

<210> SEQ ID NO 31
<211> LENGTH: 330
<212> TYPE: DNA
<213> ORGANISM: Artificial Sequence
<220> FEATURE:
<223> OTHER INFORMATION: Light chain variable region of synthetic 2C03 scFv

<400> SEQUENCE: 31

| | | | | | |
|---|---|---|---|---|---|
| cagtctgtgc | tgactcagcc | accctcagcg | tctgggaccc | ccgggcagag | ggtcaccatc | 60 |
| tcttgtactg | gctcttcatc | taatattggc | agtaattatg | tctcctggta | ccggcagctc | 120 |
| ccaggaacgg | cccccaaact | cctcatctat | tctgatagta | atcggccaag | cggggtccct | 180 |
| gaccgattct | ctggctccaa | gtctggcacc | tcagcctccc | tggccatcag | tgggctccgg | 240 |
| tccgaggatg | aggctgatta | ttactgtggt | tctgggatg | atagcctgag | cggttatgtc | 300 |
| ttcggcggag | gcaccaagct | gacggtccta | | | | 330 |

<210> SEQ ID NO 32
<211> LENGTH: 45
<212> TYPE: DNA
<213> ORGANISM: Artificial Sequence
<220> FEATURE:
<223> OTHER INFORMATION: Linker sequence(G4S)3 in all of the scFv clones

<400> SEQUENCE: 32

```
ggtggaggcg gttcaggcgg aggtggatcc ggcggtggcg gatcg                      45
```

<210> SEQ ID NO 33
<211> LENGTH: 15
<212> TYPE: PRT
<213> ORGANISM: Artificial Sequence
<220> FEATURE:
<223> OTHER INFORMATION: 15-mer peptide

<400> SEQUENCE: 33

```
Lys Glu Ala Leu Ala Lys Ser Glu Met Asn Val Asn Met Lys Tyr
 1               5                  10                  15
```

<210> SEQ ID NO 34
<211> LENGTH: 15
<212> TYPE: PRT
<213> ORGANISM: Artificial Sequence
<220> FEATURE:
<223> OTHER INFORMATION: 15-mer peptide

<400> SEQUENCE: 34

```
Ala Lys Ser Glu Met Asn Val Asn Met Lys Tyr Gln Leu Pro Asn
 1               5                  10                  15
```

<210> SEQ ID NO 35
<211> LENGTH: 15
<212> TYPE: PRT
<213> ORGANISM: Artificial Sequence
<220> FEATURE:
<223> OTHER INFORMATION: 15-mer peptide

<400> SEQUENCE: 35

```
Met Asn Val Asn Met Lys Tyr Gln Leu Pro Asn Phe Thr Ala Glu
 1               5                  10                  15
```

<210> SEQ ID NO 36
<211> LENGTH: 15
<212> TYPE: PRT
<213> ORGANISM: Artificial Sequence
<220> FEATURE:
<223> OTHER INFORMATION: 15-mer peptide

<400> SEQUENCE: 36

```
Met Lys Tyr Gln Leu Pro Asn Phe Thr Ala Glu Thr Pro Ile Gln
 1               5                  10                  15
```

<210> SEQ ID NO 37
<211> LENGTH: 15
<212> TYPE: PRT
<213> ORGANISM: Artificial Sequence
<220> FEATURE:
<223> OTHER INFORMATION: 15-mer peptide

<400> SEQUENCE: 37

```
Leu Pro Asn Phe Thr Ala Glu Thr Pro Ile Gln Asn Val Ile Leu
 1               5                  10                  15
```

<210> SEQ ID NO 38
<211> LENGTH: 15
<212> TYPE: PRT
<213> ORGANISM: Artificial Sequence
<220> FEATURE:
<223> OTHER INFORMATION: 15-mer peptide

<400> SEQUENCE: 38

```
Thr Ala Glu Thr Pro Ile Gln Asn Val Ile Leu His Glu His His
```

<210> SEQ ID NO 39
<211> LENGTH: 15
<212> TYPE: PRT
<213> ORGANISM: Artificial Sequence
<220> FEATURE:
<223> OTHER INFORMATION: 15-mer peptide

<400> SEQUENCE: 39

Pro Ile Gln Asn Val Ile Leu His Glu His His Ile Phe Leu Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: 15-mer peptide

<400> SEQUENCE: 40

Val Ile Leu His Glu His His Ile Phe Leu Gly Ala Thr Asn Tyr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: 15-mer peptide

<400> SEQUENCE: 41

Glu His His Ile Phe Leu Gly Ala Thr Asn Tyr Ile Tyr Val Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: 15-mer peptide

<400> SEQUENCE: 42

Phe Leu Gly Ala Thr Asn Tyr Ile Tyr Val Leu Asn Glu Glu Asp
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: 15-mer peptide

<400> SEQUENCE: 43

Thr Asn Tyr Ile Tyr Val Leu Asn Glu Glu Asp Leu Gln Lys Val
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: 15-mer peptide

<400> SEQUENCE: 44

Tyr Val Leu Asn Glu Glu Asp Leu Gln Lys Val Ala Glu Tyr Lys
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: 15-mer peptide

<400> SEQUENCE: 45

Glu Glu Asp Leu Gln Lys Val Ala Glu Tyr Lys Thr Gly Pro Val
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: 15-mer peptide

<400> SEQUENCE: 46

Gln Lys Val Ala Glu Tyr Lys Thr Gly Pro Val Leu Glu His Pro
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: 15-mer peptide

<400> SEQUENCE: 47

Glu Tyr Lys Thr Gly Pro Val Leu Glu His Pro Asp Cys Phe Pro
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: 15-mer peptide

<400> SEQUENCE: 48

Gly Pro Val Leu Glu His Pro Asp Cys Phe Pro Cys Gln Asp Cys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: 15-mer peptide

<400> SEQUENCE: 49

Glu His Pro Asp Cys Phe Pro Cys Gln Asp Cys Ser Ser Lys Ala
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: 15-mer peptide

<400> SEQUENCE: 50

Cys Phe Pro Cys Gln Asp Cys Ser Ser Lys Ala Asn Leu Ser Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: 15-mer peptide

<400> SEQUENCE: 51

Gln Asp Cys Ser Ser Lys Ala Asn Leu Ser Gly Gly Val Trp Lys
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: 15-mer peptide

<400> SEQUENCE: 52

Ser Lys Ala Asn Leu Ser Gly Gly Val Trp Lys Asp Asn Ile Asn
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: 15-mer peptide

<400> SEQUENCE: 53

Leu Ser Gly Gly Val Trp Lys Asp Asn Ile Asn Met Ala Leu Val
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: 15-mer peptide

<400> SEQUENCE: 54

Val Trp Lys Asp Asn Ile Asn Met Ala Leu Val Val Asp Thr Tyr
1               5                   10                  15

<210> SEQ ID NO 55
<211> LENGTH: 14
<212> TYPE: PRT
<213> ORGANISM: Artificial Sequence
<220> FEATURE:
<223> OTHER INFORMATION: 15-mer peptide

<400> SEQUENCE: 55

Asn Asn Met Ala Leu Val Val Asp Thr Tyr Tyr Asp Asp Gln
1               5                   10

<210> SEQ ID NO 56
<211> LENGTH: 15
<212> TYPE: PRT
<213> ORGANISM: Artificial Sequence
<220> FEATURE:
<223> OTHER INFORMATION: 15-mer peptide

<400> SEQUENCE: 56

Ala Leu Val Val Asp Thr Tyr Tyr Asp Asp Gln Leu Ile Ser Cys
1               5                   10                  15

```
<210> SEQ ID NO 57
<211> LENGTH: 15
<212> TYPE: PRT
<213> ORGANISM: Artificial Sequence
<220> FEATURE:
<223> OTHER INFORMATION: 15-mer peptide

<400> SEQUENCE: 57

Asp Thr Tyr Tyr Asp Asp Gln Leu Ile Ser Cys Gly Ser Val Asn
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: 15-mer peptide

<400> SEQUENCE: 58

Asp Asp Gln Leu Ile Ser Cys Gly Ser Val Asn Arg Gly Thr Cys
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: 15-mer peptide

<400> SEQUENCE: 59

Ile Ser Cys Gly Ser Val Asn Arg Gly Thr Cys Gln Arg His Val
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: 15-mer peptide

<400> SEQUENCE: 60

Ser Val Asn Arg Gly Thr Cys Gln Arg His Val Phe Pro His Asn
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: 15-mer peptide

<400> SEQUENCE: 61

Gly Thr Cys Gln Arg His Val Phe Pro His Asn His Thr Ala Asp
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: 15-mer peptide

<400> SEQUENCE: 62

Arg His Val Phe Pro His Asn His Thr Ala Asp Ile Gln Ser Glu
1               5                   10                  15

<210> SEQ ID NO 63
```

<211> LENGTH: 15
<212> TYPE: PRT
<213> ORGANISM: Artificial Sequence
<220> FEATURE:
<223> OTHER INFORMATION: 15-mer peptide

<400> SEQUENCE: 63

Pro His Asn His Thr Ala Asp Ile Gln Ser Glu Val His Cys Ile
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: 15-mer peptide

<400> SEQUENCE: 64

Thr Ala Asp Ile Gln Ser Glu Val His Cys Ile Phe Ser Pro Gln
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: 15-mer peptide

<400> SEQUENCE: 65

Gln Ser Glu Val His Cys Ile Phe Ser Pro Gln Ile Glu Glu Pro
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: 15-mer peptide

<400> SEQUENCE: 66

His Cys Ile Phe Ser Pro Gln Ile Glu Glu Pro Ser Gln Cys Pro
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: 15-mer peptide

<400> SEQUENCE: 67

Ser Pro Gln Ile Glu Glu Pro Ser Gln Cys Pro Asp Cys Val Val
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: 15-mer peptide

<400> SEQUENCE: 68

Glu Glu Pro Ser Gln Cys Pro Asp Cys Val Val Ser Ala Leu Gly
1               5                   10                  15

<210> SEQ ID NO 69
<211> LENGTH: 15

```
<212> TYPE: PRT
<213> ORGANISM: Artificial Sequence
<220> FEATURE:
<223> OTHER INFORMATION: 15-mer peptide

<400> SEQUENCE: 69

Gln Cys Pro Asp Cys Val Val Ser Ala Leu Gly Ala Lys Val Leu
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: 15-mer peptide

<400> SEQUENCE: 70

Cys Val Val Ser Ala Leu Gly Ala Lys Val Leu Ser Ser Val Lys
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: 15-mer peptide

<400> SEQUENCE: 71

Ala Leu Gly Ala Lys Val Leu Ser Ser Val Lys Asp Arg Phe Ile
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: 15-mer peptide

<400> SEQUENCE: 72

Lys Val Leu Ser Ser Val Lys Asp Arg Phe Ile Asn Phe Phe Val
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: 15-mer peptide

<400> SEQUENCE: 73

Ser Val Lys Asp Arg Phe Ile Asn Phe Phe Val Gly Asn Thr Ile
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: 15-mer peptide

<400> SEQUENCE: 74

Arg Phe Ile Asn Phe Phe Val Gly Asn Thr Ile Asn Ser Ser Tyr
1               5                   10                  15

<210> SEQ ID NO 75
<211> LENGTH: 14
<212> TYPE: PRT
```

```
<213> ORGANISM: Artificial Sequence
<220> FEATURE:
<223> OTHER INFORMATION: 15-mer peptide

<400> SEQUENCE: 75

Phe Phe Val Gly Asn Thr Ile Asn Ser Tyr Phe Pro Asp His
1               5                   10

<210> SEQ ID NO 76
<211> LENGTH: 15
<212> TYPE: PRT
<213> ORGANISM: Artificial Sequence
<220> FEATURE:
<223> OTHER INFORMATION: 15-mer peptide

<400> SEQUENCE: 76

Asn Thr Ile Asn Ser Ser Tyr Phe Pro Asp His Pro Leu His Ser
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: 15-mer peptide

<400> SEQUENCE: 77

Ser Ser Tyr Phe Pro Asp His Pro Leu His Ser Ile Ser Val Arg
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: 15-mer peptide

<400> SEQUENCE: 78

Pro Asp His Pro Leu His Ser Ile Ser Val Arg Arg Leu Lys Glu
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: 15-mer peptide

<400> SEQUENCE: 79

Leu His Ser Ile Ser Val Arg Arg Leu Lys Glu Thr Lys Asp Gly
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: 15-mer peptide

<400> SEQUENCE: 80

Ser Val Arg Arg Leu Lys Glu Thr Lys Asp Gly Phe Met Phe Leu
1               5                   10                  15

<210> SEQ ID NO 81
<211> LENGTH: 15
<212> TYPE: PRT
<213> ORGANISM: Artificial Sequence
```

```
<220> FEATURE:
<223> OTHER INFORMATION: 15-mer peptide

<400> SEQUENCE: 81

Leu Lys Glu Thr Lys Asp Gly Phe Met Phe Leu Thr Asp Gln Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: 15-mer peptide

<400> SEQUENCE: 82

Lys Asp Gly Phe Met Phe Leu Thr Asp Gln Ser Tyr Thr Asp Val
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: 15-mer peptide

<400> SEQUENCE: 83

Met Phe Leu Thr Asp Gln Ser Tyr Ile Asp Val Leu Pro Glu Phe
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: 15-mer peptide

<400> SEQUENCE: 84

Asp Gln Ser Tyr Ile Asp Val Leu Pro Glu Phe Arg Asp Ser Tyr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: 15-mer peptide

<400> SEQUENCE: 85

Ile Asp Val Leu Pro Glu Phe Arg Asp Ser Tyr Pro Ile Lys Tyr
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: 15-mer peptide

<400> SEQUENCE: 86

Pro Glu Phe Arg Asp Ser Tyr Pro Ile Lys Tyr Val His Ala Phe
1               5                   10                  15

<210> SEQ ID NO 87
<211> LENGTH: 15
<212> TYPE: PRT
<213> ORGANISM: Artificial Sequence
<220> FEATURE:
```

```
<223> OTHER INFORMATION: 15-mer peptide

<400> SEQUENCE: 87

Asp Ser Tyr Pro Ile Lys Tyr Val His Ala Phe Glu Ser Asn Asn
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: 15-mer peptide

<400> SEQUENCE: 88

Ile Lys Tyr Val His Ala Phe Glu Ser Asn Asn Phe Ile Tyr Phe
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: 15-mer peptide

<400> SEQUENCE: 89

His Ala Phe Glu Ser Asn Asn Phe Ile Tyr Phe Leu Thr Val Gln
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: 15-mer peptide

<400> SEQUENCE: 90

Ser Asn Asn Phe Ile Tyr Phe Leu Thr Val Gln Arg Glu Thr Leu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: 15-mer peptide

<400> SEQUENCE: 91

Ile Tyr Phe Leu Thr Val Gln Arg Glu Thr Leu Asp Ala Gln Thr
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: 15-mer peptide

<400> SEQUENCE: 92

Thr Val Gln Arg Glu Thr Leu Asp Ala Gln Thr Phe His Thr Arg
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: 15-mer peptide
```

<400> SEQUENCE: 93

Glu Thr Leu Asp Ala Gln Thr Phe His Thr Arg Ile Ile Arg Phe
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: 15-mer peptide

<400> SEQUENCE: 94

Ala Gln Thr Phe His Thr Arg Ile Ile Arg Phe Cys Ser Ile Asn
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: 15-mer peptide

<400> SEQUENCE: 95

His Thr Arg Ile Ile Arg Phe Cys Ser Ile Asn Ser Gly Leu His
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: 15-mer peptide

<400> SEQUENCE: 96

Ile Arg Phe Cys Ser Ile Asn Ser Gly Leu His Ser Tyr Met Glu
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: 15-mer peptide

<400> SEQUENCE: 97

Ser Ile Asn Ser Gly Leu His Ser Tyr Met Glu Met Pro Leu Glu
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: 15-mer peptide

<400> SEQUENCE: 98

Gly Leu His Ser Tyr Met Glu Met Pro Leu Glu Cys Ile Leu Thr
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: 15-mer peptide

```
<400> SEQUENCE: 99

Tyr Met Glu Met Pro Leu Glu Cys Ile Leu Thr Glu Lys Arg Lys
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: 15-mer peptide

<400> SEQUENCE: 100

Pro Leu Glu Cys Ile Leu Thr Glu Lys Arg Lys Lys Arg Ser Thr
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: 15-mer peptide

<400> SEQUENCE: 101

Ile Leu Thr Glu Lys Arg Lys Lys Arg Ser Thr Lys Lys Glu Val
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: 15-mer peptide

<400> SEQUENCE: 102

Lys Arg Lys Lys Arg Ser Thr Lys Lys Glu Val Phe Asn Ile Leu
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: 15-mer peptide

<400> SEQUENCE: 103

Arg Ser Thr Lys Lys Glu Val Phe Asn Ile Leu Gln Ala Ala Tyr
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: 15-mer peptide

<400> SEQUENCE: 104

Lys Glu Val Phe Asn Ile Leu Gln Ala Ala Tyr Val Ser Lys Pro
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: 15-mer peptide

<400> SEQUENCE: 105
```

```
Asn Ile Leu Gln Ala Ala Tyr Val Ser Lys Pro Gly Ala Gln Leu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: 15-mer peptide

<400> SEQUENCE: 106

Ala Ala Tyr Val Ser Lys Pro Gly Ala Gln Leu Ala Ala Gln Ile
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: 15-mer peptide

<400> SEQUENCE: 107

Ser Lys Pro Gly Ala Gln Leu Ala Arg Gln Ile Gly Ala Ser Leu
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: 15-mer peptide

<400> SEQUENCE: 108

Ala Gln Leu Ala Arg Gln Ile Gly Ala Ser Leu Asn Asp Asp Ile
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: 15-mer peptide

<400> SEQUENCE: 109

Arg Gln Ile Gly Ala Ser Leu Asn Asp Asp Ile Leu Phe Gly Val
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: 15-mer peptide

<400> SEQUENCE: 110

Ala Ser Leu Asn Asp Asp Ile Leu Phe Gly Val Phe Ala Gln Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: 15-mer peptide

<400> SEQUENCE: 111
```

```
Asp Asp Ile Leu Phe Gly Val Phe Ala Gln Ser Lys Pro Asp Ser
1               5                   10                  15
```

<210> SEQ ID NO 112
<211> LENGTH: 15
<212> TYPE: PRT
<213> ORGANISM: Artificial Sequence
<220> FEATURE:
<223> OTHER INFORMATION: 15-mer peptide

<400> SEQUENCE: 112

```
Phe Gly Val Phe Ala Gln Ser Lys Pro Asp Ser Ala Glu Pro Met
1               5                   10                  15
```

<210> SEQ ID NO 113
<211> LENGTH: 15
<212> TYPE: PRT
<213> ORGANISM: Artificial Sequence
<220> FEATURE:
<223> OTHER INFORMATION: 15-mer peptide

<400> SEQUENCE: 113

```
Ala Gln Ser Lys Pro Asp Ser Ala Glu Pro Met Asp Arg Ser Ala
1               5                   10                  15
```

<210> SEQ ID NO 114
<211> LENGTH: 15
<212> TYPE: PRT
<213> ORGANISM: Artificial Sequence
<220> FEATURE:
<223> OTHER INFORMATION: 15-mer peptide

<400> SEQUENCE: 114

```
Pro Asp Ser Ala Glu Pro Met Asp Arg Ser Ala Met Cys Ala Phe
1               5                   10                  15
```

<210> SEQ ID NO 115
<211> LENGTH: 15
<212> TYPE: PRT
<213> ORGANISM: Artificial Sequence
<220> FEATURE:
<223> OTHER INFORMATION: 15-mer peptide

<400> SEQUENCE: 115

```
Glu Pro Met Asp Arg Ser Ala Met Cys Ala Phe Pro Ile Lys Tyr
1               5                   10                  15
```

<210> SEQ ID NO 116
<211> LENGTH: 15
<212> TYPE: PRT
<213> ORGANISM: Artificial Sequence
<220> FEATURE:
<223> OTHER INFORMATION: 15-mer peptide

<400> SEQUENCE: 116

```
Arg Ser Ala Met Cys Ala Phe Pro Ile Lys Tyr Val Asn Asp Phe
1               5                   10                  15
```

<210> SEQ ID NO 117
<211> LENGTH: 15
<212> TYPE: PRT
<213> ORGANISM: Artificial Sequence
<220> FEATURE:
<223> OTHER INFORMATION: 15-mer peptide

<400> SEQUENCE: 117

Cys Ala Phe Pro Ile Lys Tyr Val Asn Asp Phe Phe Asn Lys Ile

<210> SEQ ID NO 118
<211> LENGTH: 15
<212> TYPE: PRT
<213> ORGANISM: Artificial Sequence
<220> FEATURE:
<223> OTHER INFORMATION: 15-mer peptide

<400> SEQUENCE: 118

Ile Lys Tyr Val Asn Asp Phe Phe Asn Lys Ile Val Asn Lys Asn
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: 15-mer peptide

<400> SEQUENCE: 119

Asn Asp Phe Phe Asn Lys Ile Val Asn Lys Asn Asn Val Arg Cys
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: 15-mer peptide

<400> SEQUENCE: 120

Glu His Cys Phe Asn Arg Thr Leu Leu Arg Asn Ser Ser Gly Cys
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: 15-mer peptide

<400> SEQUENCE: 121

Asn Lys Ile Val Asn Lys Asn Asn Val Arg Cys Leu Gln His Phe
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: 15-mer peptide

<400> SEQUENCE: 122

Asn Lys Asn Asn Val Arg Cys Leu Gln His Phe Tyr Gly Pro Asn
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: 15-mer peptide

<400> SEQUENCE: 123

Val Arg Cys Leu Gln His Phe Tyr Gly Pro Asn His Glu His Cys
1               5                   10                  15

```
<210> SEQ ID NO 124
<211> LENGTH: 15
<212> TYPE: PRT
<213> ORGANISM: Artificial Sequence
<220> FEATURE:
<223> OTHER INFORMATION: 15-mer peptide

<400> SEQUENCE: 124

Gln His Phe Tyr Gly Pro Asn His Glu His Cys Phe Asn Arg Thr
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: 15-mer peptide

<400> SEQUENCE: 125

Gly Pro Asn His Glu His Cys Phe Asn Arg Thr Leu Leu Arg Asn
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: 15-mer peptide

<400> SEQUENCE: 126

Asn Arg Thr Leu Leu Arg Asn Ser Ser Gly Cys Glu Ala Arg Arg
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: 15-mer peptide

<400> SEQUENCE: 127

Leu Arg Asn Ser Ser Gly Cys Glu Ala Arg Arg Asp Glu Tyr Arg
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: 15-mer peptide

<400> SEQUENCE: 128

Ser Gly Cys Glu Ala Arg Arg Asp Glu Tyr Arg Thr Glu Phe Thr
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: 15-mer peptide

<400> SEQUENCE: 129

Ala Arg Arg Asp Glu Tyr Arg Thr Glu Phe Thr Thr Ala Leu Gln
1               5                   10                  15
```

```
<210> SEQ ID NO 130
<211> LENGTH: 15
<212> TYPE: PRT
<213> ORGANISM: Artificial Sequence
<220> FEATURE:
<223> OTHER INFORMATION: 15-mer peptide

<400> SEQUENCE: 130

Glu Tyr Arg Thr Glu Phe Thr Thr Ala Leu Gln Arg Val Asp Leu
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: 15-mer peptide

<400> SEQUENCE: 131

Glu Phe Thr Thr Ala Leu Gln Arg Val Asp Leu Phe Met Gly Gln
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: 15-mer peptide

<400> SEQUENCE: 132

Ala Leu Gln Arg Val Asp Leu Phe Met Gly Gln Phe Ser Glu Val
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: 15-mer peptide

<400> SEQUENCE: 133

Val Asp Leu Phe Met Gly Gln Phe Ser Glu Val Leu Leu Thr Ser
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: 15-mer peptide

<400> SEQUENCE: 134

Met Gly Gln Phe Ser Glu Val Leu Leu Thr Ser Ile Ser Thr Phe
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: 15-mer peptide

<400> SEQUENCE: 135

Ser Glu Val Leu Leu Thr Ser Ile Ser Thr Phe Ile Lys Gly Asp
1               5                   10                  15
```

```
<210> SEQ ID NO 136
<211> LENGTH: 15
<212> TYPE: PRT
<213> ORGANISM: Artificial Sequence
<220> FEATURE:
<223> OTHER INFORMATION: 15-mer peptide

<400> SEQUENCE: 136

Leu Thr Ser Ile Ser Thr Phe Ile Lys Gly Asp Leu Thr Ile Ala
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: 15-mer peptide

<400> SEQUENCE: 137

Ser Thr Phe Ile Lys Gly Asp Leu Thr Ile Ala Asn Leu Gly Thr
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: 15-mer peptide

<400> SEQUENCE: 138

Lys Gly Asp Leu Thr Ile Ala Asn Leu Gly Thr Ser Glu Gly Arg
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: 15-mer peptide

<400> SEQUENCE: 139

Thr Ile Ala Asn Leu Gly Thr Ser Glu Gly Arg Phe Met Gln Val
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: 15-mer peptide

<400> SEQUENCE: 140

Leu Gly Thr Ser Glu Gly Arg Phe Met Gln Val Val Val Ser Arg
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: 15-mer peptide

<400> SEQUENCE: 141

Glu Gly Arg Phe Met Gln Val Val Val Ser Arg Ser Gly Pro Ser
1               5                   10                  15

<210> SEQ ID NO 142
```

<211> LENGTH: 15
<212> TYPE: PRT
<213> ORGANISM: Artificial Sequence
<220> FEATURE:
<223> OTHER INFORMATION: 15-mer peptide

<400> SEQUENCE: 142

Met Gln Val Val Val Ser Arg Ser Gly Pro Ser Thr Pro His Val
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: 15-mer peptide

<400> SEQUENCE: 143

Val Ser Arg Ser Gly Pro Ser Thr Pro His Val Asn Phe Leu Leu
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: 15-mer peptide

<400> SEQUENCE: 144

Gly Pro Ser Thr Pro His Val Asn Phe Leu Leu Asp Ser His Pro
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: 15-mer peptide

<400> SEQUENCE: 145

Pro His Val Asn Phe Leu Leu Asp Ser His Pro Val Ser Pro Glu
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: 15-mer peptide

<400> SEQUENCE: 146

Phe Leu Leu Asp Ser His Pro Val Ser Pro Glu Val Ile Val Glu
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: 15-mer peptide

<400> SEQUENCE: 147

Ser His Pro Val Ser Pro Glu Val Ile Val Glu His Thr Leu Asn
1               5                   10                  15

<210> SEQ ID NO 148
<211> LENGTH: 15

-continued

```
<212> TYPE: PRT
<213> ORGANISM: Artificial Sequence
<220> FEATURE:
<223> OTHER INFORMATION: 15-mer peptide

<400> SEQUENCE: 148

Ser Pro Glu Val Ile Val Glu His Thr Leu Asn Gln Asn Gly Tyr
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: 15-mer peptide

<400> SEQUENCE: 149

Ile Val Glu His Thr Leu Asn Gln Asn Gly Tyr Thr Leu Val Ile
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: 15-mer peptide

<400> SEQUENCE: 150

Thr Leu Asn Gln Asn Gly Tyr Thr Leu Val Ile Thr Gly Lys Lys
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: 15-mer peptide

<400> SEQUENCE: 151

Asn Gly Tyr Thr Leu Val Ile Thr Gly Lys Lys Ile Thr Lys Ile
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: 15-mer peptide

<400> SEQUENCE: 152

Leu Val Ile Thr Gly Lys Lys Ile Thr Lys Ile Pro Leu Asn Gly
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: 15-mer peptide

<400> SEQUENCE: 153

Gly Lys Lys Ile Thr Lys Ile Pro Leu Asn Gly Leu Gly Cys Arg
1               5                   10                  15

<210> SEQ ID NO 154
<211> LENGTH: 15
<212> TYPE: PRT
```

```
<213> ORGANISM: Artificial Sequence
<220> FEATURE:
<223> OTHER INFORMATION: 15-mer peptide

<400> SEQUENCE: 154

Thr Lys Ile Pro Leu Asn Gly Leu Gly Cys Arg His Phe Gln Ser
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: 15-mer peptide

<400> SEQUENCE: 155

Leu Asn Gly Leu Gly Cys Arg His Phe Gln Ser Cys Ser Gln Cys
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: 15-mer peptide

<400> SEQUENCE: 156

Gly Cys Arg His Phe Gln Ser Cys Ser Gln Cys Leu Ser Ala Pro
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: 15-mer peptide

<400> SEQUENCE: 157

Phe Gln Ser Cys Ser Gln Cys Leu Ser Ala Pro Pro Phe Val Gln
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: 15-mer peptide

<400> SEQUENCE: 158

Ser Gln Cys Leu Ser Ala Pro Pro Phe Val Gln Cys Gly Trp Cys
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: 15-mer peptide

<400> SEQUENCE: 159

Ser Ala Pro Pro Phe Val Gln Cys Gly Trp Cys His Asp Lys Cys
1               5                   10                  15

<210> SEQ ID NO 160
<211> LENGTH: 15
<212> TYPE: PRT
<213> ORGANISM: Artificial Sequence
```

```
<220> FEATURE:
<223> OTHER INFORMATION: 15-mer peptide

<400> SEQUENCE: 160

Phe Val Gln Cys Gly Trp Cys His Asp Lys Cys Val Arg Ser Glu
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: 15-mer peptide

<400> SEQUENCE: 161

Gly Trp Cys His Asp Lys Cys Val Arg Ser Glu Glu Cys Leu Ser
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: 15-mer peptide

<400> SEQUENCE: 162

Asp Lys Cys Val Arg Ser Glu Glu Cys Leu Ser Gly Thr Trp Thr
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: 15-mer peptide

<400> SEQUENCE: 163

Arg Ser Glu Glu Cys Leu Ser Gly Thr Trp Thr Gln Gln Ile Cys
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: 15-mer peptide

<400> SEQUENCE: 164

Cys Leu Ser Gly Thr Trp Thr Gln Gln Ile Cys Leu Pro Ala Ile
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: 15-mer peptide

<400> SEQUENCE: 165

Thr Trp Thr Gln Gln Ile Cys Leu Pro Ala Ile Tyr Lys Val Phe
1               5                   10                  15

<210> SEQ ID NO 166
<211> LENGTH: 15
<212> TYPE: PRT
<213> ORGANISM: Artificial Sequence
<220> FEATURE:
```

<223> OTHER INFORMATION: 15-mer peptide

<400> SEQUENCE: 166

Gln Ile Cys Leu Pro Ala Ile Tyr Lys Val Phe Pro Asn Ser Ala
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: 15-mer peptide

<400> SEQUENCE: 167

Pro Ala Ile Tyr Lys Val Phe Pro Asn Ser Ala Pro Leu Glu Gly
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: 15-mer peptide

<400> SEQUENCE: 168

Lys Val Phe Pro Asn Ser Ala Pro Leu Glu Gly Gly Thr Arg Leu
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: 15-mer peptide

<400> SEQUENCE: 169

Asn Ser Ala Pro Leu Glu Gly Gly Thr Arg Leu Thr Ile Cys Gly
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: 15-mer peptide

<400> SEQUENCE: 170

Leu Glu Gly Gly Thr Arg Leu Thr Ile Cys Gly Trp Asp Phe Gly
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: 15-mer peptide

<400> SEQUENCE: 171

Thr Arg Leu Thr Ile Cys Gly Trp Asp Phe Gly Phe Arg Arg Asn
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: 15-mer peptide

```
<400> SEQUENCE: 172

Ile Cys Gly Trp Asp Phe Gly Phe Arg Arg Asn Asn Lys Phe Asp
1               5                  10                  15

<210> SEQ ID NO 173
<211> LENGTH: 15
<212> TYPE: PRT
<213> ORGANISM: Artificial Sequence
<220> FEATURE:
<223> OTHER INFORMATION: 15-mer peptide

<400> SEQUENCE: 173

Asp Phe Gly Phe Arg Arg Asn Asn Lys Phe Asp Leu Lys Lys Thr
1               5                  10                  15

<210> SEQ ID NO 174
<211> LENGTH: 15
<212> TYPE: PRT
<213> ORGANISM: Artificial Sequence
<220> FEATURE:
<223> OTHER INFORMATION: 15-mer peptide

<400> SEQUENCE: 174

Arg Arg Asn Asn Lys Phe Asp Leu Lys Lys Thr Arg Val Leu Leu
1               5                  10                  15

<210> SEQ ID NO 175
<211> LENGTH: 15
<212> TYPE: PRT
<213> ORGANISM: Artificial Sequence
<220> FEATURE:
<223> OTHER INFORMATION: 15-mer peptide

<400> SEQUENCE: 175

Lys Phe Asp Leu Lys Lys Thr Arg Val Leu Leu Gly Asn Glu Ser
1               5                  10                  15

<210> SEQ ID NO 176
<211> LENGTH: 15
<212> TYPE: PRT
<213> ORGANISM: Artificial Sequence
<220> FEATURE:
<223> OTHER INFORMATION: 15-mer peptide

<400> SEQUENCE: 176

Lys Lys Thr Arg Val Leu Leu Gly Asn Glu Ser Cys Thr Leu Thr
1               5                  10                  15

<210> SEQ ID NO 177
<211> LENGTH: 14
<212> TYPE: PRT
<213> ORGANISM: Artificial Sequence
<220> FEATURE:
<223> OTHER INFORMATION: 15-mer peptide

<400> SEQUENCE: 177

Val Leu Leu Gly Asn Glu Ser Cys Thr Thr Leu Ser Glu Ser
1               5                  10

<210> SEQ ID NO 178
<211> LENGTH: 15
<212> TYPE: PRT
<213> ORGANISM: Artificial Sequence
<220> FEATURE:
<223> OTHER INFORMATION: 15-mer peptide
```

-continued

<400> SEQUENCE: 178

Asn Glu Ser Cys Thr Leu Thr Leu Ser Glu Ser Thr Met Asn Thr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: 15-mer peptide

<400> SEQUENCE: 179

Thr Leu Thr Leu Ser Glu Ser Thr Met Asn Thr Leu Lys Cys Thr
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: 15-mer peptide

<400> SEQUENCE: 180

Ser Glu Ser Thr Met Asn Thr Leu Lys Cys Thr Val Gly Pro Ala
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: 15-mer peptide

<400> SEQUENCE: 181

Met Asn Thr Leu Lys Cys Thr Val Gly Pro Ala Met Asn Lys His
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: 15-mer peptide

<400> SEQUENCE: 182

Lys Cys Thr Val Gly Pro Ala Met Asn Lys His Phe Asn Met Ser
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: 15-mer peptide

<400> SEQUENCE: 183

Gly Pro Ala Met Asn Lys His Phe Asn Met Ser Ile Ile Ile Ser
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: 15-mer peptide

<400> SEQUENCE: 184

Asn Lys His Phe Asn Met Ser Ile Ile Ile Ser Asn Gly His Gly
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: 15-mer peptide

<400> SEQUENCE: 185

Asn Met Ser Ile Ile Ile Ser Asn Gly His Gly Thr Thr Gln Tyr
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: 15-mer peptide

<400> SEQUENCE: 186

Ile Ile Ser Asn Gly His Gly Thr Thr Gln Tyr Ser Thr Phe Ser
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: 15-mer peptide

<400> SEQUENCE: 187

Gly His Gly Thr Thr Gln Tyr Ser Thr Phe Ser Tyr Val Asp Pro
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: 15-mer peptide

<400> SEQUENCE: 188

Thr Gln Tyr Ser Thr Phe Ser Tyr Val Asp Pro Val Ile Thr Ser
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: 15-mer peptide

<400> SEQUENCE: 189

Thr Phe Ser Tyr Val Asp Pro Val Ile Thr Ser Ile Ser Pro Lys
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: 15-mer peptide

<400> SEQUENCE: 190

```
Val Asp Pro Val Ile Thr Ser Ile Ser Pro Lys Tyr Gly Pro Met
1               5                   10                  15
```

<210> SEQ ID NO 191
<211> LENGTH: 15
<212> TYPE: PRT
<213> ORGANISM: Artificial Sequence
<220> FEATURE:
<223> OTHER INFORMATION: 15-mer peptide

<400> SEQUENCE: 191

```
Ile Thr Ser Ile Ser Pro Lys Tyr Gly Pro Met Ala Gly Gly Thr
1               5                   10                  15
```

<210> SEQ ID NO 192
<211> LENGTH: 15
<212> TYPE: PRT
<213> ORGANISM: Artificial Sequence
<220> FEATURE:
<223> OTHER INFORMATION: 15-mer peptide

<400> SEQUENCE: 192

```
Leu Lys Ser Val Ser Asn Ser Ile Leu Glu Cys Tyr Thr Pro Ala
1               5                   10                  15
```

<210> SEQ ID NO 193
<211> LENGTH: 15
<212> TYPE: PRT
<213> ORGANISM: Artificial Sequence
<220> FEATURE:
<223> OTHER INFORMATION: 15-mer peptide

<400> SEQUENCE: 193

```
Ser Pro Lys Tyr Gly Pro Met Ala Gly Gly Thr Leu Leu Thr Leu
1               5                   10                  15
```

<210> SEQ ID NO 194
<211> LENGTH: 15
<212> TYPE: PRT
<213> ORGANISM: Artificial Sequence
<220> FEATURE:
<223> OTHER INFORMATION: 15-mer peptide

<400> SEQUENCE: 194

```
Gly Pro Met Ala Gly Gly Thr Leu Leu Thr Leu Thr Gly Asn Tyr
1               5                   10                  15
```

<210> SEQ ID NO 195
<211> LENGTH: 15
<212> TYPE: PRT
<213> ORGANISM: Artificial Sequence
<220> FEATURE:
<223> OTHER INFORMATION: 15-mer peptide

<400> SEQUENCE: 195

```
Gly Gly Thr Leu Leu Thr Leu Thr Gly Asn Tyr Leu Asn Ser Gly
1               5                   10                  15
```

<210> SEQ ID NO 196
<211> LENGTH: 15
<212> TYPE: PRT
<213> ORGANISM: Artificial Sequence
<220> FEATURE:
<223> OTHER INFORMATION: 15-mer peptide

<400> SEQUENCE: 196

```
Leu Thr Leu Thr Gly Asn Tyr Leu Asn Ser Gly Asn Ser Arg His
```

```
1               5                   10                  15
```

<210> SEQ ID NO 197
<211> LENGTH: 15
<212> TYPE: PRT
<213> ORGANISM: Artificial Sequence
<220> FEATURE:
<223> OTHER INFORMATION: 15-mer peptide

<400> SEQUENCE: 197

```
Gly Asn Tyr Leu Asn Ser Gly Asn Ser Arg His Ile Ser Ile Gly
1               5                   10                  15
```

<210> SEQ ID NO 198
<211> LENGTH: 15
<212> TYPE: PRT
<213> ORGANISM: Artificial Sequence
<220> FEATURE:
<223> OTHER INFORMATION: 15-mer peptide

<400> SEQUENCE: 198

```
Asn Ser Gly Asn Ser Arg His Ile Ser Ile Gly Gly Lys Thr Cys
1               5                   10                  15
```

<210> SEQ ID NO 199
<211> LENGTH: 15
<212> TYPE: PRT
<213> ORGANISM: Artificial Sequence
<220> FEATURE:
<223> OTHER INFORMATION: 15-mer peptide

<400> SEQUENCE: 199

```
Ser Arg His Ile Ser Ile Gly Gly Lys Thr Cys Thr Leu Lys Ser
1               5                   10                  15
```

<210> SEQ ID NO 200
<211> LENGTH: 15
<212> TYPE: PRT
<213> ORGANISM: Artificial Sequence
<220> FEATURE:
<223> OTHER INFORMATION: 15-mer peptide

<400> SEQUENCE: 200

```
Ser Ile Gly Gly Lys Thr Cys Thr Leu Lys Ser Val Ser Asn Ser
1               5                   10                  15
```

<210> SEQ ID NO 201
<211> LENGTH: 15
<212> TYPE: PRT
<213> ORGANISM: Artificial Sequence
<220> FEATURE:
<223> OTHER INFORMATION: 15-mer peptide

<400> SEQUENCE: 201

```
Lys Thr Cys Thr Leu Lys Ser Val Ser Asn Ser Ile Leu Glu Cys
1               5                   10                  15
```

<210> SEQ ID NO 202
<211> LENGTH: 15
<212> TYPE: PRT
<213> ORGANISM: Artificial Sequence
<220> FEATURE:
<223> OTHER INFORMATION: 15-mer peptide

<400> SEQUENCE: 202

```
Ser Asn Ser Ile Leu Glu Cys Tyr Thr Pro Ala Gln Thr Ile Ser
1               5                   10                  15
```

```
<210> SEQ ID NO 203
<211> LENGTH: 15
<212> TYPE: PRT
<213> ORGANISM: Artificial Sequence
<220> FEATURE:
<223> OTHER INFORMATION: 15-mer peptide

<400> SEQUENCE: 203

Leu Glu Cys Tyr Thr Pro Ala Gln Thr Ile Ser Thr Glu Phe Ala
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: 15-mer peptide

<400> SEQUENCE: 204

Thr Pro Ala Gln Thr Ile Ser Thr Glu Phe Ala Val Lys Leu Lys
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: 15-mer peptide

<400> SEQUENCE: 205

Thr Ile Ser Thr Glu Phe Ala Val Lys Leu Lys Ile Asp Leu Ala
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: 15-mer peptide

<400> SEQUENCE: 206

Glu Phe Ala Val Lys Leu Lys Ile Asp Leu Ala Asn Arg Glu Thr
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: 15-mer peptide

<400> SEQUENCE: 207

Lys Leu Lys Ile Asp Leu Ala Asn Arg Glu Thr Ser Ile Phe Ser
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: 15-mer peptide

<400> SEQUENCE: 208

Asp Leu Ala Asn Arg Glu Thr Ser Ile Phe Ser Tyr Arg Glu Asp
1               5                   10                  15
```

<210> SEQ ID NO 209
<211> LENGTH: 15
<212> TYPE: PRT
<213> ORGANISM: Artificial Sequence
<220> FEATURE:
<223> OTHER INFORMATION: 15-mer peptide

<400> SEQUENCE: 209

Arg Glu Thr Ser Ile Phe Ser Tyr Arg Glu Asp Pro Ile Val Tyr
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: 15-mer peptide

<400> SEQUENCE: 210

Ile Phe Ser Tyr Arg Glu Asp Pro Ile Val Tyr Glu Ile His Pro
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: 15-mer peptide

<400> SEQUENCE: 211

Arg Glu Asp Pro Ile Val Tyr Glu Ile His Pro Thr Lys Ser Phe
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: 15-mer peptide

<400> SEQUENCE: 212

Ile Val Tyr Glu Ile His Pro Thr Lys Ser Phe Ile Ser Gly Gly
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: 15-mer peptide

<400> SEQUENCE: 213

Ile His Pro Thr Lys Ser Phe Ile Ser Gly Gly Ser Thr Ile Thr
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: 15-mer peptide

<400> SEQUENCE: 214

Lys Ser Phe Ile Ser Gly Gly Ser Thr Ile Thr Gly Val Gly Lys
1               5                   10                  15

-continued

```
<210> SEQ ID NO 215
<211> LENGTH: 15
<212> TYPE: PRT
<213> ORGANISM: Artificial Sequence
<220> FEATURE:
<223> OTHER INFORMATION: 15-mer peptide

<400> SEQUENCE: 215

Ser Gly Gly Ser Thr Ile Thr Gly Val Gly Lys Asn Leu Asn Ser
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: 15-mer peptide

<400> SEQUENCE: 216

Thr Ile Thr Gly Val Gly Lys Asn Leu Asn Ser Val Ser Val Pro
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: 15-mer peptide

<400> SEQUENCE: 217

Val Gly Lys Asn Leu Asn Ser Val Ser Val Pro Arg Met Val Ile
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: 15-mer peptide

<400> SEQUENCE: 218

Leu Asn Ser Val Ser Val Pro Arg Met Val Ile Asn Val His Glu
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: 15-mer peptide

<400> SEQUENCE: 219

Ser Val Pro Arg Met Val Ile Asn Val His Glu Ala Gly Arg Asn
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: 15-mer peptide

<400> SEQUENCE: 220

Met Val Ile Asn Val His Glu Ala Gly Arg Asn Phe Thr Val Ala
1               5                   10                  15

<210> SEQ ID NO 221
```

<210> SEQ ID NO 221
<211> LENGTH: 15
<212> TYPE: PRT
<213> ORGANISM: Artificial Sequence
<220> FEATURE:
<223> OTHER INFORMATION: 15-mer peptide

<400> SEQUENCE: 221

```
Val His Glu Ala Gly Arg Asn Phe Thr Val Ala Cys Gln His Arg
1               5                   10                  15
```

<210> SEQ ID NO 222
<211> LENGTH: 15
<212> TYPE: PRT
<213> ORGANISM: Artificial Sequence
<220> FEATURE:
<223> OTHER INFORMATION: 15-mer peptide

<400> SEQUENCE: 222

```
Gly Arg Asn Phe Thr Val Ala Cys Gln His Arg Ser Asn Ser Glu
1               5                   10                  15
```

<210> SEQ ID NO 223
<211> LENGTH: 15
<212> TYPE: PRT
<213> ORGANISM: Artificial Sequence
<220> FEATURE:
<223> OTHER INFORMATION: 15-mer peptide

<400> SEQUENCE: 223

```
Thr Val Ala Cys Gln His Arg Ser Asn Ser Glu Ile Ile Cys Cys
1               5                   10                  15
```

<210> SEQ ID NO 224
<211> LENGTH: 15
<212> TYPE: PRT
<213> ORGANISM: Artificial Sequence
<220> FEATURE:
<223> OTHER INFORMATION: 15-mer peptide

<400> SEQUENCE: 224

```
Gln His Arg Ser Asn Ser Glu Ile Ile Cys Cys Thr Thr Pro Ser
1               5                   10                  15
```

<210> SEQ ID NO 225
<211> LENGTH: 15
<212> TYPE: PRT
<213> ORGANISM: Artificial Sequence
<220> FEATURE:
<223> OTHER INFORMATION: 15-mer peptide

<400> SEQUENCE: 225

```
Asn Ser Glu Ile Ile Cys Cys Thr Thr Pro Ser Leu Gln Gln Leu
1               5                   10                  15
```

<210> SEQ ID NO 226
<211> LENGTH: 15
<212> TYPE: PRT
<213> ORGANISM: Artificial Sequence
<220> FEATURE:
<223> OTHER INFORMATION: 15-mer peptide

<400> SEQUENCE: 226

```
Ile Cys Cys Thr Thr Pro Ser Leu Gln Gln Leu Asn Leu Gln Leu
1               5                   10                  15
```

<210> SEQ ID NO 227
<211> LENGTH: 15

```
<212> TYPE: PRT
<213> ORGANISM: Artificial Sequence
<220> FEATURE:
<223> OTHER INFORMATION: 15-mer peptide

<400> SEQUENCE: 227

Thr Pro Ser Leu Gln Gln Leu Asn Leu Gln Leu Pro Leu Lys Thr
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: 15-mer peptide

<400> SEQUENCE: 228

Gln Gln Leu Asn Leu Gln Leu Pro Leu Lys Thr Lys Ala Phe Phe
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: 15-mer peptide

<400> SEQUENCE: 229

Leu Gln Leu Pro Leu Lys Thr Lys Ala Phe Phe Met Leu Asp Gly
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: 15-mer peptide

<400> SEQUENCE: 230

Leu Lys Thr Lys Ala Phe Phe Met Leu Asp Gly Ile Leu Ser Lys
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: 15-mer peptide

<400> SEQUENCE: 231

Ala Phe Phe Met Leu Asp Gly Ile Leu Ser Lys Tyr Phe Asp Leu
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: 15-mer peptide

<400> SEQUENCE: 232

Leu Asp Gly Ile Leu Ser Lys Tyr Phe Asp Leu Ile Tyr Val His
1               5                   10                  15

<210> SEQ ID NO 233
<211> LENGTH: 15
<212> TYPE: PRT
```

<213> ORGANISM: Artificial Sequence
<220> FEATURE:
<223> OTHER INFORMATION: 15-mer peptide

<400> SEQUENCE: 233

Leu Ser Lys Tyr Phe Asp Leu Ile Tyr Val His Asn Pro Val Phe
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: 15-mer peptide

<400> SEQUENCE: 234

Phe Asp Leu Ile Tyr Val His Asn Pro Val Phe Lys Pro Phe Glu
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: 15-mer peptide

<400> SEQUENCE: 235

Tyr Val His Asn Pro Val Phe Lys Pro Phe Glu Lys Pro Val Met
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: 15-mer peptide

<400> SEQUENCE: 236

Pro Val Phe Lys Pro Phe Glu Lys Pro Val Met Ile Ser Met Gly
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: 15-mer peptide

<400> SEQUENCE: 237

Pro Phe Glu Lys Pro Val Met Ile Ser Met Gly Asn Glu Asn Val
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: 15-mer peptide

<400> SEQUENCE: 238

Pro Val Met Ile Ser Met Gly Asn Glu Asn Val Leu Glu Ile Lys
1               5                   10                  15

<210> SEQ ID NO 239
<211> LENGTH: 15
<212> TYPE: PRT
<213> ORGANISM: Artificial Sequence

```
<220> FEATURE:
<223> OTHER INFORMATION: 15-mer peptide

<400> SEQUENCE: 239

Ser Met Gly Asn Glu Asn Val Leu Glu Ile Lys Gly Asn Asp Ile
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: 15-mer peptide

<400> SEQUENCE: 240

Glu Asn Val Leu Glu Ile Lys Gly Asn Asp Ile Asp Pro Glu Ala
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: 15-mer peptide

<400> SEQUENCE: 241

Glu Ile Lys Gly Asn Asp Ile Asp Pro Glu Ala Val Lys Gly Glu
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: 15-mer peptide

<400> SEQUENCE: 242

Asn Asp Ile Asp Pro Glu Ala Val Lys Gly Glu Val Leu Lys Val
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: 15-mer peptide

<400> SEQUENCE: 243

Pro Glu Ala Val Lys Gly Glu Val Leu Lys Val Gly Asn Lys Ser
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: 15-mer peptide

<400> SEQUENCE: 244

Lys Gly Glu Val Leu Lys Val Gly Asn Lys Ser Cys Glu Asn Ile
1               5                   10                  15

<210> SEQ ID NO 245
<211> LENGTH: 15
<212> TYPE: PRT
<213> ORGANISM: Artificial Sequence
<220> FEATURE:
```

<223> OTHER INFORMATION: 15-mer peptide

<400> SEQUENCE: 245

Leu Lys Val Gly Asn Lys Ser Cys Glu Asn Ile His Leu His Ser
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: 15-mer peptide

<400> SEQUENCE: 246

Asn Lys Ser Cys Glu Asn Ile His Leu His Ser Glu Ala Val Leu
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: 15-mer peptide

<400> SEQUENCE: 247

Glu Asn Ile His Leu His Ser Glu Ala Val Leu Cys Thr Val Pro
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: 15-mer peptide

<400> SEQUENCE: 248

Leu His Ser Glu Ala Val Leu Cys Thr Val Pro Asn Asp Leu Leu
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: 15-mer peptide

<400> SEQUENCE: 249

Ala Val Leu Cys Thr Val Pro Asn Asp Leu Leu Lys Leu Asn Ser
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: 15-mer peptide

<400> SEQUENCE: 250

Thr Val Pro Asn Asp Leu Leu Lys Leu Asn Ser Glu Leu Asn Ile
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: 15-mer peptide

```
<400> SEQUENCE: 251

Asp Leu Leu Lys Leu Asn Ser Glu Leu Asn Ile Glu Trp Lys Gln
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: 15-mer peptide

<400> SEQUENCE: 252

Leu Asn Ser Glu Leu Asn Ile Glu Trp Lys Gln Ala Ile Ser Ser
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: 15-mer peptide

<400> SEQUENCE: 253

Leu Asn Ile Glu Trp Lys Gln Ala Ile Ser Ser Thr Val Leu Gly
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: 15-mer peptide

<400> SEQUENCE: 254

Trp Lys Gln Ala Ile Ser Ser Thr Val Leu Gly Lys Val Ile Val
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: 15-mer peptide

<400> SEQUENCE: 255

Ile Ser Ser Thr Val Leu Gly Lys Val Ile Val Gln Pro Asp Gln
1               5                   10                  15

<210> SEQ ID NO 256
<211> LENGTH: 14
<212> TYPE: PRT
<213> ORGANISM: Artificial Sequence
<220> FEATURE:
<223> OTHER INFORMATION: 15-mer peptide

<400> SEQUENCE: 256

Val Leu Gly Lys Val Ile Val Gln Pro Asp Gln Asn Phe Thr
1               5                   10

<210> SEQ ID NO 257
<211> LENGTH: 15
<212> TYPE: PRT
<213> ORGANISM: Artificial Sequence
<220> FEATURE:
<223> OTHER INFORMATION: 15-mer peptide
```

<400> SEQUENCE: 257

Phe Gln Ser Cys Ser Gln Cys Leu Ser Ala Pro Pro Phe Val Gln
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: 15-mer peptide

<400> SEQUENCE: 258

Ser Gln Cys Leu Ser Ala Pro Pro Phe Val Gln Cys Gly Trp Cys
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: 15-mer peptide

<400> SEQUENCE: 259

Ser Ala Pro Pro Phe Val Gln Cys Gln Trp Cys His Asp Lys Cys
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: 15-mer peptide

<400> SEQUENCE: 260

Ser Val Lys Asp Arg Phe Ile Asn Phe Val Gly Asn Thr Ile
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: 15-mer peptide

<400> SEQUENCE: 261

Arg Phe Ile Asn Phe Val Gly Asn Thr Ile Asn Ser Ser Tyr
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: 15-mer peptide

<400> SEQUENCE: 262

Phe Leu Gly Ala Thr Asn Tyr Ile Tyr Val Leu Asn Glu Glu Asp
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: 15-mer peptide

<400> SEQUENCE: 263

Thr Asn Tyr Ile Tyr Val Leu Asn Glu Glu Asp Leu Gln Lys Val
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: 15-mer peptide

<400> SEQUENCE: 264

Arg His Val Phe Pro His Asn His Thr Ala Asp Ile Gln Ser Glu
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: 15-mer peptide

<400> SEQUENCE: 265

Pro His Asn His Thr Ala Asp Ile Gln Ser Glu Val His Cys Ile
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: 15-mer peptide

<400> SEQUENCE: 266

Lys Asp Gly Phe Met Phe Leu Thr Asp Gln Ser Tyr Ile Asp Val
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: 15-mer peptide

<400> SEQUENCE: 267

Met Phe Leu Thr Asp Gln Ser Tyr Ile Asp Val Leu Pro Glu Phe
1               5                   10                  15

<210> SEQ ID NO 268
<211> LENGTH: 25
<212> TYPE: PRT
<213> ORGANISM: Artificial Sequence
<220> FEATURE:
<223> OTHER INFORMATION: Heavy chain FR/CDR sequence

<400> SEQUENCE: 268

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 269
<211> LENGTH: 8
<212> TYPE: PRT
<213> ORGANISM: Artificial Sequence
<220> FEATURE:
<223> OTHER INFORMATION: Heavy chain FR/CDR sequence

<400> SEQUENCE: 269

Gly Phe Thr Phe Ser Asn Tyr Ala
1               5

<210> SEQ ID NO 270
<211> LENGTH: 15
<212> TYPE: PRT
<213> ORGANISM: Artificial Sequence
<220> FEATURE:
<223> OTHER INFORMATION: Heavy chain FR/CDR sequence

<400> SEQUENCE: 270

Met Ser Trp Val Arg Gln Ala Pro Gly Lys Gly Leu Glu Trp Val
1               5                   10                  15

<210> SEQ ID NO 271
<211> LENGTH: 8
<212> TYPE: PRT
<213> ORGANISM: Artificial Sequence
<220> FEATURE:
<223> OTHER INFORMATION: Heavy chain FR/CDR sequence

<400> SEQUENCE: 271

Ile Ser Tyr Ser Gly Gly Ser Thr
1               5

<210> SEQ ID NO 272
<211> LENGTH: 38
<212> TYPE: PRT
<213> ORGANISM: Artificial Sequence
<220> FEATURE:
<223> OTHER INFORMATION: Heavy chain FR/CDR sequence

<400> SEQUENCE: 272

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 273
<211> LENGTH: 20
<212> TYPE: PRT
<213> ORGANISM: Artificial Sequence
<220> FEATURE:
<223> OTHER INFORMATION: Heavy chain FR/CDR sequence

<400> SEQUENCE: 273

Ala Lys Ala Ser Arg Ser Cys Gln Arg Pro Cys Ser Tyr Ala Asn
1               5                   10                  15

Gly Met Asp Val
            20

<210> SEQ ID NO 274
<211> LENGTH: 11
<212> TYPE: PRT
<213> ORGANISM: Artificial Sequence
<220> FEATURE:
<223> OTHER INFORMATION: Heavy chain FR/CDR sequence

<400> SEQUENCE: 274

Trp Gly Gln Gly Thr Leu Val Thr Val Ser Ser
1               5                   10

```
<210> SEQ ID NO 275
<211> LENGTH: 25
<212> TYPE: PRT
<213> ORGANISM: Artificial Sequence
<220> FEATURE:
<223> OTHER INFORMATION: Heavy chain FR/CDR sequence

<400> SEQUENCE: 275

Glu Val Gln Leu Leu Glu Ser Gly Gly Gly Leu Val Gln Thr Gly Gly
1               5                   10                  15

Ser Leu Arg Leu Ser Cys Ala Ala Ser
            20                  25

<210> SEQ ID NO 276
<211> LENGTH: 8
<212> TYPE: PRT
<213> ORGANISM: Artificial Sequence
<220> FEATURE:
<223> OTHER INFORMATION: Heavy chain FR/CDR sequence

<400> SEQUENCE: 276

Gly Phe Thr Phe Ser Ser Tyr Asp
1               5

<210> SEQ ID NO 277
<211> LENGTH: 17
<212> TYPE: PRT
<213> ORGANISM: Artificial Sequence
<220> FEATURE:
<223> OTHER INFORMATION: Heavy chain FR/CDR sequence

<400> SEQUENCE: 277

Met Ser Trp Val Arg Arg Ala Pro Gly Lys Gly Leu Glu Trp Val Ser
1               5                   10                  15

Trp

<210> SEQ ID NO 278
<211> LENGTH: 8
<212> TYPE: PRT
<213> ORGANISM: Artificial Sequence
<220> FEATURE:
<223> OTHER INFORMATION: Heavy chain FR/CDR sequence

<400> SEQUENCE: 278

Ile Ser His Gly Gly Ser Ser Ile
1               5

<210> SEQ ID NO 279
<211> LENGTH: 33
<212> TYPE: PRT
<213> ORGANISM: Artificial Sequence
<220> FEATURE:
<223> OTHER INFORMATION: Heavy chain FR/CDR sequence

<400> SEQUENCE: 279

Ser Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr

<210> SEQ ID NO 280
<211> LENGTH: 14
```

```
<212> TYPE: PRT
<213> ORGANISM: Artificial Sequence
<220> FEATURE:
<223> OTHER INFORMATION: Heavy chain FR/CDR sequence

<400> SEQUENCE: 280

Ala Lys Asp Ala Tyr Pro Ile Arg Gln Glu Thr Phe Asp Tyr
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Heavy chain FR/CDR sequence

<400> SEQUENCE: 281

Trp Gly Gln Gly Thr Leu Val Thr Val Ser Ser
1               5                   10

<210> SEQ ID NO 282
<211> LENGTH: 25
<212> TYPE: PRT
<213> ORGANISM: Artificial Sequence
<220> FEATURE:
<223> OTHER INFORMATION: Heavy chain FR/CDR sequence

<400> SEQUENCE: 282

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 283
<211> LENGTH: 8
<212> TYPE: PRT
<213> ORGANISM: Artificial Sequence
<220> FEATURE:
<223> OTHER INFORMATION: Heavy chain FR/CDR sequence

<400> SEQUENCE: 283

Gly Phe Thr Phe Ser Asn Tyr Ala
1               5

<210> SEQ ID NO 284
<211> LENGTH: 17
<212> TYPE: PRT
<213> ORGANISM: Artificial Sequence
<220> FEATURE:
<223> OTHER INFORMATION: Heavy chain FR/CDR sequence

<400> SEQUENCE: 284

Met Ser Trp Val Arg Gln Ala Pro Gly Lys Gly Leu Glu Trp Val Ser
1               5                   10                  15

Ala

<210> SEQ ID NO 285
<211> LENGTH: 8
<212> TYPE: PRT
<213> ORGANISM: Artificial Sequence
<220> FEATURE:
<223> OTHER INFORMATION: Heavy chain FR/CDR sequence

<400> SEQUENCE: 285

Ile Ser Tyr Asp Ser Gly Ser Ile
1               5
```

```
<210> SEQ ID NO 286
<211> LENGTH: 38
<212> TYPE: PRT
<213> ORGANISM: Artificial Sequence
<220> FEATURE:
<223> OTHER INFORMATION: Heavy chain FR/CDR sequence

<400> SEQUENCE: 286

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 287
<211> LENGTH: 20
<212> TYPE: PRT
<213> ORGANISM: Artificial Sequence
<220> FEATURE:
<223> OTHER INFORMATION: Heavy chain FR/CDR sequence

<400> SEQUENCE: 287

Ala Lys Ala Ala Arg Ser Cys Arg Asn Trp Ser Cys Ser Tyr Ala Asn
1               5                   10                  15

Gly Met Asp Val
            20

<210> SEQ ID NO 288
<211> LENGTH: 11
<212> TYPE: PRT
<213> ORGANISM: Artificial Sequence
<220> FEATURE:
<223> OTHER INFORMATION: Heavy chain FR/CDR sequence

<400> SEQUENCE: 288

Trp Gly Gln Gly Thr Leu Val Thr Val Ser Ser
1               5                   10

<210> SEQ ID NO 289
<211> LENGTH: 25
<212> TYPE: PRT
<213> ORGANISM: Artificial Sequence
<220> FEATURE:
<223> OTHER INFORMATION: Light chain FR/CDR sequence

<400> SEQUENCE: 289

Gln Ser Val Leu Thr Gln Pro Pro Ser Ala Ser Gly Thr Pro Gly Gln
1               5                   10                  15

Arg Val Thr Ile Ser Cys Thr Gly Ser
            20                  25

<210> SEQ ID NO 290
<211> LENGTH: 8
<212> TYPE: PRT
<213> ORGANISM: Artificial Sequence
<220> FEATURE:
<223> OTHER INFORMATION: Light chain FR/CDR sequence

<400> SEQUENCE: 290

Ser Ser Asn Ile Gly Asn Asn Tyr
1               5
```

<210> SEQ ID NO 291
<211> LENGTH: 17
<212> TYPE: PRT
<213> ORGANISM: Artificial Sequence
<220> FEATURE:
<223> OTHER INFORMATION: Light chain FR/CDR sequence

<400> SEQUENCE: 291

Val Thr Trp Tyr Gln Gln Leu Pro Gly Thr Ala Pro Lys Leu Leu Ile
1               5                   10                  15

Tyr

<210> SEQ ID NO 292
<211> LENGTH: 36
<212> TYPE: PRT
<213> ORGANISM: Artificial Sequence
<220> FEATURE:
<223> OTHER INFORMATION: Light chain FR/CDR sequence

<400> SEQUENCE: 292

His Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
            35

<210> SEQ ID NO 293
<211> LENGTH: 11
<212> TYPE: PRT
<213> ORGANISM: Artificial Sequence
<220> FEATURE:
<223> OTHER INFORMATION: Light chain FR/CDR sequence

<400> SEQUENCE: 293

Gly Ser Trp Asp Tyr Ser Leu Ser Ala Tyr Val
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Light chain FR/CDR sequence

<400> SEQUENCE: 294

Phe Gly Gly Gly Thr Lys Leu Thr Val Leu
1               5                   10

<210> SEQ ID NO 295
<211> LENGTH: 25
<212> TYPE: PRT
<213> ORGANISM: Artificial Sequence
<220> FEATURE:
<223> OTHER INFORMATION: Light chain FR/CDR sequence

<400> SEQUENCE: 295

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 296
<211> LENGTH: 8
<212> TYPE: PRT

```
<213> ORGANISM: Artificial Sequence
<220> FEATURE:
<223> OTHER INFORMATION: Light chain FR/CDR sequence

<400> SEQUENCE: 296

Ser Ser Asn Ile Gly Asn Asn Asp
1               5

<210> SEQ ID NO 297
<211> LENGTH: 17
<212> TYPE: PRT
<213> ORGANISM: Artificial Sequence
<220> FEATURE:
<223> OTHER INFORMATION: Light chain FR/CDR sequence

<400> SEQUENCE: 297

Val Ser Trp Tyr Gln Gln Leu Pro Gly Thr Ala Pro Lys Leu Leu Ile
1               5                   10                  15

Tyr

<210> SEQ ID NO 298
<211> LENGTH: 36
<212> TYPE: PRT
<213> ORGANISM: Artificial Sequence
<220> FEATURE:
<223> OTHER INFORMATION: Light chain FR/CDR sequence

<400> SEQUENCE: 298

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 299
<211> LENGTH: 11
<212> TYPE: PRT
<213> ORGANISM: Artificial Sequence
<220> FEATURE:
<223> OTHER INFORMATION: Light chain FR/CDR sequence

<400> SEQUENCE: 299

Ala Ser Trp Asp Ser Ser Leu Ser Gly Tyr Val
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Light chain FR/CDR sequence

<400> SEQUENCE: 300

Phe Gly Gly Gly Thr Lys Leu Thr Val Leu
1               5                   10

<210> SEQ ID NO 301
<211> LENGTH: 25
<212> TYPE: PRT
<213> ORGANISM: Artificial Sequence
<220> FEATURE:
<223> OTHER INFORMATION: Light chain FR/CDR sequence

<400> SEQUENCE: 301
```

Gln Ser Val Leu Thr Gln Pro Pro Ser Ala Ser Gly Thr Pro Gly Gln
1               5                   10                  15

Arg Val Thr Ile Ser Cys Thr Gly Ser
            20                  25

<210> SEQ ID NO 302
<211> LENGTH: 8
<212> TYPE: PRT
<213> ORGANISM: Artificial Sequence
<220> FEATURE:
<223> OTHER INFORMATION: Light chain FR/CDR sequence

<400> SEQUENCE: 302

Ser Ser Asn Ile Gly Ser Asn Tyr
1               5

<210> SEQ ID NO 303
<211> LENGTH: 17
<212> TYPE: PRT
<213> ORGANISM: Artificial Sequence
<220> FEATURE:
<223> OTHER INFORMATION: Light chain FR/CDR sequence

<400> SEQUENCE: 303

Val Ser Trp Tyr Arg Gln Leu Pro Gly Thr Ala Pro Lys Leu Leu Ile
1               5                   10                  15

Tyr

<210> SEQ ID NO 304
<211> LENGTH: 36
<212> TYPE: PRT
<213> ORGANISM: Artificial Sequence
<220> FEATURE:
<223> OTHER INFORMATION: Light chain FR/CDR sequence

<400> SEQUENCE: 304

Asn Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 305
<211> LENGTH: 11
<212> TYPE: PRT
<213> ORGANISM: Artificial Sequence
<220> FEATURE:
<223> OTHER INFORMATION: Light chain FR/CDR sequence

<400> SEQUENCE: 305

Gly Ser Trp Asp Asp Ser Leu Ser Gly Tyr Val
1               5                   10

<210> SEQ ID NO 306
<211> LENGTH: 10
<212> TYPE: PRT
<213> ORGANISM: Artificial Sequence
<220> FEATURE:
<223> OTHER INFORMATION: Light chain FR/CDR sequence

<400> SEQUENCE: 306

Phe Gly Gly Gly Thr Lys Leu Thr Val Leu
1               5                   10